US007902166B2

(12) United States Patent
Houchen et al.

(10) Patent No.: US 7,902,166 B2
(45) Date of Patent: Mar. 8, 2011

(54) COMPOSITIONS COMPRISING INHIBITORS OF RNA BINDING PROTEINS AND METHODS OF PRODUCING AND USING SAME

(75) Inventors: Courtney Houchen, Edmond, OK (US); Shrikant Anant, Edmond, OK (US); Sripathi M. Sureban, Oklahoma City, OK (US); Satish Ramalingam, Oklahoma City, OK (US); Dhamalingam Surbramaniam, Oklahoma City, OK (US); Rama P. Ramanujam, Dublin, OH (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 12/386,550

(22) Filed: Apr. 20, 2009

(65) Prior Publication Data
US 2009/0252784 A1    Oct. 8, 2009

Related U.S. Application Data

(63) Continuation-in-part of application No. 12/384,387, filed on Apr. 3, 2009.

(60) Provisional application No. 61/124,654, filed on Apr. 18, 2008, provisional application No. 61/123,045, filed on Apr. 3, 2008.

(51) Int. Cl.
*A01N 43/04* (2006.01)
*A61K 31/70* (2006.01)
*C07H 21/02* (2006.01)
*C07H 21/04* (2006.01)

(52) U.S. Cl. ...... 514/44; 536/23.1; 536/24.3; 536/24.33; 536/24.5

(58) Field of Classification Search ............. 536/23.1, 536/24.3, 24.33, 24.5; 514/44
See application file for complete search history.

(56) References Cited

U.S. PATENT DOCUMENTS

| | | |
|---|---|---|
| 7,345,027 B2 | 3/2008 | Tolentino et al. |
| 7,511,025 B2 | 3/2009 | Wyatt et al. |
| 7,511,132 B2 | 3/2009 | Khvorova et al. |

OTHER PUBLICATIONS

Smart et al. (J. Neurochem., 2007, vol. 101:1367-1379).*
Mukherji et al. (Biochemistry, 2006 vol. 45:15529-15540).*
Xi et al. (Clin Cancer Research, 2006 vol. 12:2014-2024).*
Elbashir et al. (Methods, 2002 vol. 26:199-213).*
May, et al., "DCAMKL-1 and LGR5 Mark Quiescent and Cycling Intestinal Stem Cells Respectively", Stem Cell, pp. 1-38 (2009).
Sureban et al., "Knockdown of RNA Binding Portein Musashi-1 Leads to Tumor Regression In Vivo", Gastroenterology 134:1448-1458, (2008).

* cited by examiner

*Primary Examiner* — Sean McGarry
*Assistant Examiner* — Terra Cotta Gibbs
(74) *Attorney, Agent, or Firm* — Dunlap Codding, P.C.

(57) ABSTRACT

Compositions for inhibiting RNA binding proteins, as well as methods of producing and using the same, are disclosed herein.

Figure 1:
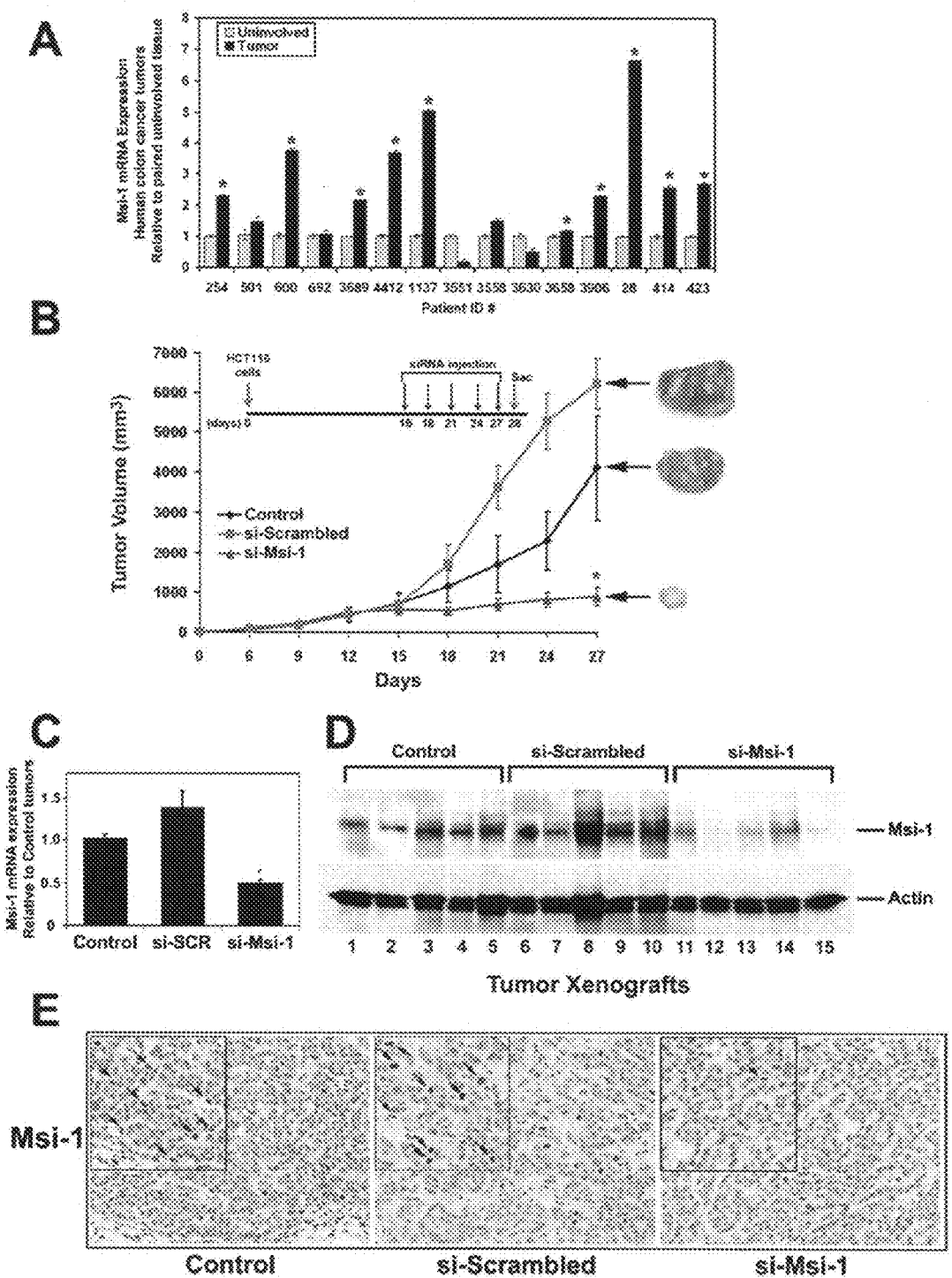

11 Claims, 29 Drawing Sheets
(18 of 29 Drawing Sheet(s) Filed in Color)

Figure 2
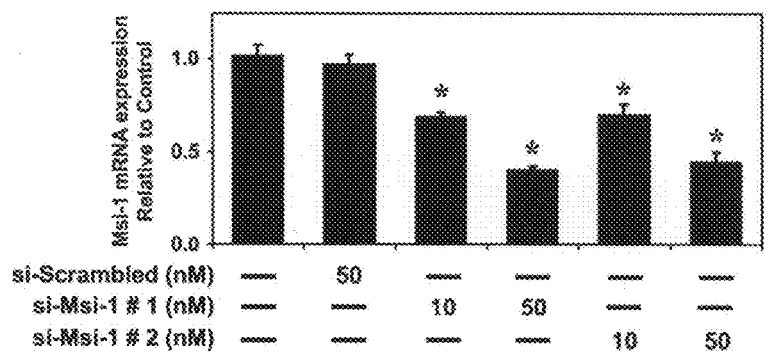
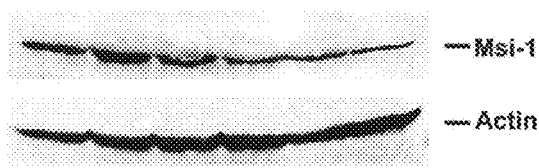
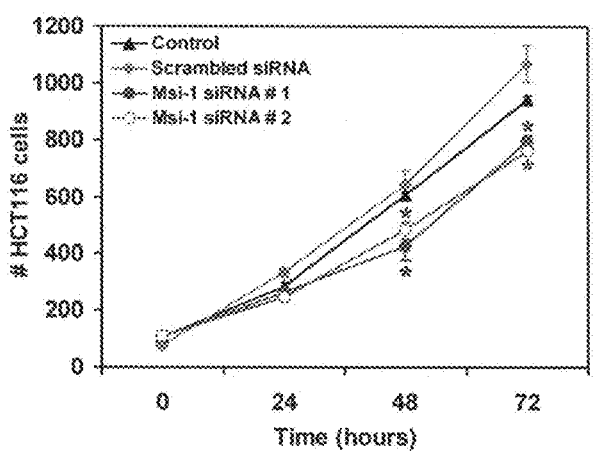
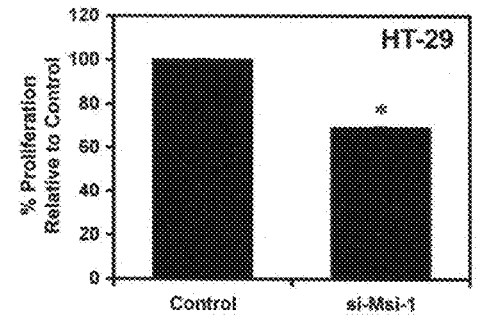

Figure 7
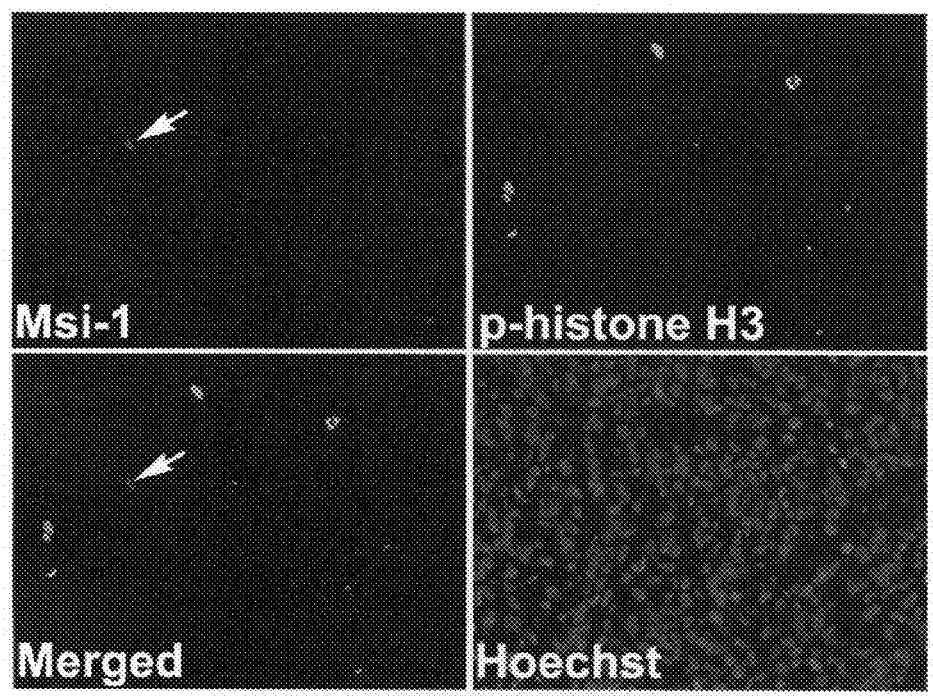
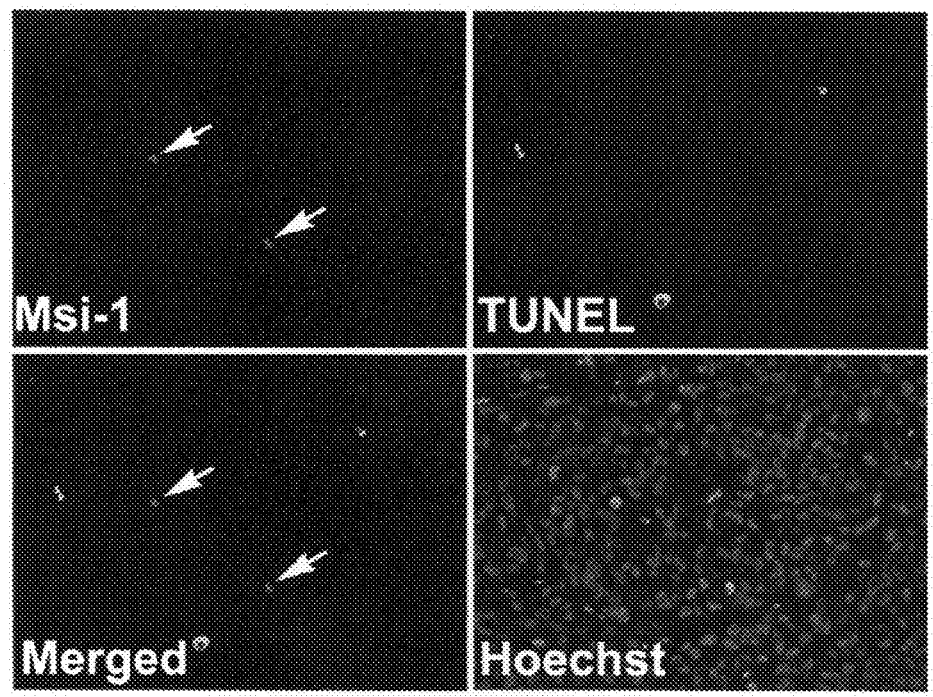

Figure 8
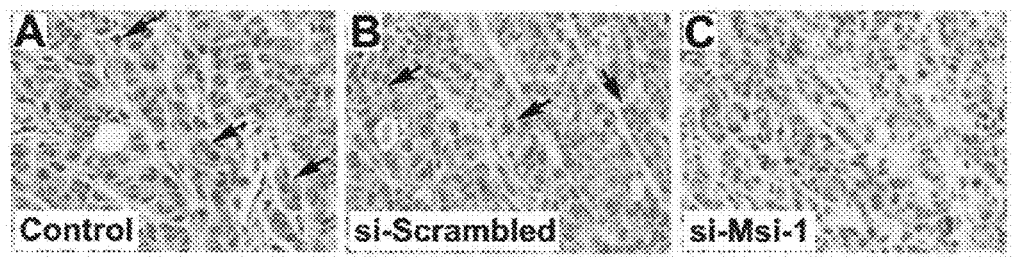
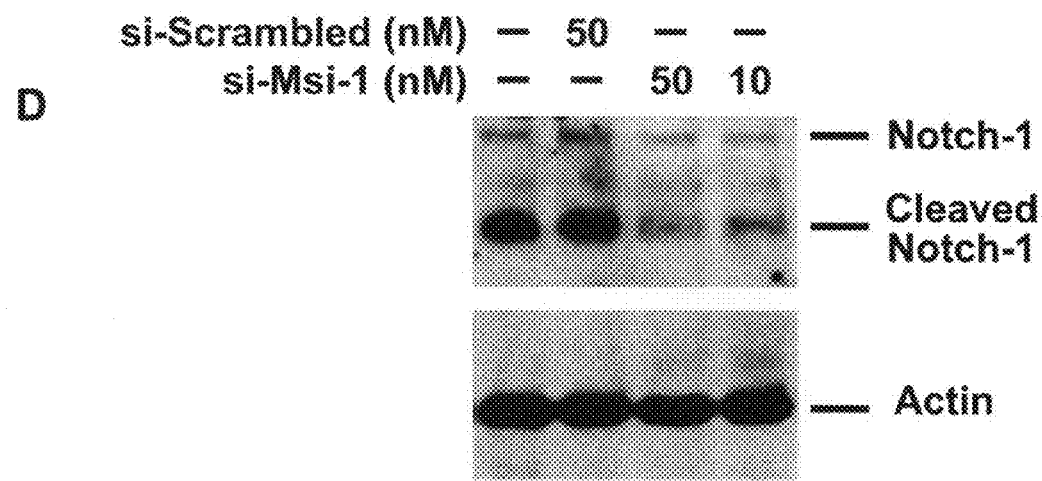
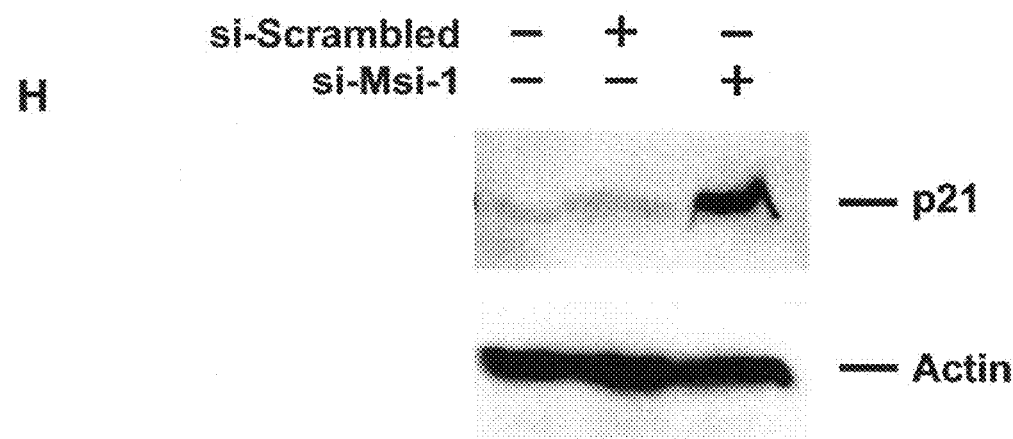

Figure 17. mRNA expression analysis of human colorectal adenocarcinoma samples.

| Sl # | Pt # (a) | Sex | Age | Diagnosis / Site (b) | Stage (c) | Staging code (AJCC) (d) | Metastasis | mRNA expression relative to uninvolved surrounding tissue (e) | | |
|---|---|---|---|---|---|---|---|---|---|---|
| | | | | | | | | RBM3 | COX-2 | HuR |
| 1 | 7251 | M | 57 | Colon – Descending | I | T1; N0; M0 | No | 3.18 | 5.8 | 2.84 |
| 2 | 13191 | M | 58 | Colon – NOS | I | T2; N0; M0 | No | 1.36 | 1.27 | 6.07 |
| 3 | 670 | F | 78 | Colon – Ascending | IIA | T3; N0; M0 | No | 3.17 | 26.67 | 2.83 |
| 4 | 922 | F | 88 | Colon – Descending | II A | T3; N0; M0 | No | 0.58 | 1.49 | 1.03 |
| 5 | 1113 | F | 62 | Rectum | II A | T3; N0; M0 | No | 10.1 | 2.64 | 3.41 |
| 6 | 1328 | F | 53 | Colon – Ascending | II A | T3; N0; M0 | No | 3.19 | 0.727 | 1.36 |
| 7 | 5292 | M | 86 | Colon – Sigmoid | II A | T3; N0; M0 | No | 2.46 | 1.68 | 1.32 |
| 8 | 940 | F | 79 | Colon-Cecum | II A or III B | T3; N ; M0 | No | 7.59 | 5.85 | 1.27 |
| 9 | 920 | F | 87 | Colon – Transverse | II B | T4; N ; M0 | No | 3.05 | 141 | 3.11 |
| 10 | 1008 | F | 44 | Colon – Transverse | III B | T3; N ; M0 | No | 2.2 | 39.65 | 2.82 |
| 11 | 94 | M | 63 | Colon-Hepatic Flexure | IIIB | T3; N1; M0 | No | 4.77 | 3.49 | 1.97 |
| 12 | 261 | M | 67 | Colon – Ascending | IV | T4; N0; M1 | No | 2.21 | 0.025 | 0.93 |
| 13 | 774 | M | 60 | Colon – NOS | IV | T3; N1; M1 | Yes | 1.15 | 1.46 | 1.49 |
| 14 | 10061 | F | 84 | Colon – Cecum | I/IV | T2; N0; M1 | Yes | 3.32 | 0.198 | 2.78 |
| 15 | 10218 | M | 96 | Colon – Cecum | IV | – | Yes | 9.23 | 0.859 | 9.55 |

NIH-3T3 cells injected into nude mice cause the mice to have tumors.

Epidermal growth factor induces RBM3 promoter activity in HCT-116 cells

RBM3 siRNA inhibits angiogenesis because tube formation is inhibited.

In vitro angiogenesis assay

Control     Scrambled siRNA     RBM3 siRNA

US 7,902,166 B2

COMPOSITIONS COMPRISING INHIBITORS OF RNA BINDING PROTEINS AND METHODS OF PRODUCING AND USING SAME

CROSS REFERENCE TO RELATED APPLICATIONS

This application claims benefit under 35 U.S.C. 119(e) of provisional application U.S. Ser. No. 61/124,654, filed Apr. 18, 2008. This application is also a continuation-in-part of pending application U.S. Ser. No. 12/384,387, filed Apr. 3, 2009; which claims benefit under 35 U.S.C. 119(e) of provisional application U.S. Ser. No. 61/123,045, filed Apr. 3, 2008.

The entire contents of each of the above referenced patents and patent applications are hereby expressly incorporated herein by reference.

STATEMENT REGARDING FEDERALLY SPONSORED RESEARCH OR DEVELOPMENT

This invention was made with government support under Contract Numbers CA109269 and DK062265 awarded by the National Institutes of Health. The government has certain rights in the invention.

BACKGROUND OF THE INVENTION

1. Field of the Invention

The presently disclosed and claimed invention relates generally to anti-cancer compositions and methods of producing and using same, and in particular, but not by way of limitation, to compositions comprising inhibitors of RNA binding proteins and methods of producing and using same.

2. Description of the Background Art

Stem cells are ultimately responsible for the entire cell production process in a particular tissue. They have a potential capability of large numbers of cell division and maintenance of cell replacement during the entire life of an animal (Potten et al., 2003). The epithelial cells of intestinal villi of the small intestinal mucosa are replaced within 2-3 days, and this rapid cell turnover, in addition to self-renewal by the intestinal tissue, is governed by epithelial stem cells present in the crypts of the small intestine (Okano et al., 2005). The Musashi-1 (Msi-1) gene encodes an RNA binding protein involved in early asymmetric divisions generating differentiated cells from neural stem cells or progenitor cells. Msi-1 expression was observed in the small intestine at the fourth-sixth cell position from the bottom of the crypts and in the cells in the deepest portion of the large intestine, where the possibility of stem cells is considered to be high (Okano et al., 2005; and Marshman et al., 2002).

Several lines of evidence suggest that some tumor types are maintained by a small population of self-renewing cells or "cancer stem cells". The transformation of a normal mucosal epithelial cell to an invasive colorectal carcinoma occurs via a well-coordinated accumulation of mutations in a series of critical genes (Riehl et al., 2006). In gut, tumorigenesis arises from the stem cell population located near the base of intestine and colonic crypts (Potten et al., 2003). Msi-1 has been shown to be a positive regulator of Notch signaling through its interaction and translational repression of mammalian Numb (mNumb) messenger RNA (mRNA) (an inhibitor of Notch signaling) (Okano et al., 2002). Recently, reports have emerged showing that Msi-1 regulates neuronal development through the translational repression of p21$^{WAF1/Cip1}$ (Battelli et al., 2006; Sakakibara et al., 1996; and Imai et al., 2001). Msi-1 expression in intestinal tumors of APC$^{min/+}$ mice is thought to be caused by activation of Notch signaling. However, the definitive role of Msi-1 in colon cancer and cancer progression is currently unclear.

Dysregulated expression of oncogenes and tumor suppressors is a critical regulator of tumorigenesis. Known targets that lead to a tumorigenic phenotype include cyclooxygenase (COX)-2, interleukin (IL)-8 and vascular endothelial growth factor (VEGF) (Dixon et al., 2001; Dubois et al., 1998; Wang et al., 2005). COX-2 is the rate-limiting enzyme in the production of prostaglandins (PGs), an important mediator of various cellular processes including increased proliferation, apoptosis resistance and enhanced angiogenesis (Krysan et al., 2005; Mukhopadhyay et al., 2003b). COX-2 overexpression occurs in multiple tumors, and can be observed at various stages of tumorigenesis (Eberhart et al., 1994). While transcriptional activation of COX-2 is an early event, it is also regulated at the posttranscriptional levels of mRNA stability and translation (Dixon et al., 2000).

Distinct cis-acting AU-rich elements (ARE) sequence elements located within the 3'untranslated region (3'UTR) have been identified in the COX-2, IL-8 and VEGF mRNA that regulate mRNA stability and translation (Cok & Morrison, 2001; Dixon et al., 2001; Ristimaki et al., 1996). Specifically, the first sixty nucleotides in COX-2 3'UTR encode AREs, which regulate mRNA stability and translation (Cok & Morrison, 2001; Mukhopadhyay et al., 2003a). RNA binding protein HuR interacts with these ARE sequences to regulate the stability and translation of COX-2 mRNA (Cok & Morrison, 2001; Dixon et al., 2000). HuR is also upregulated in various cancers (Denkert et al., 2006a; Denkert et al., 2004; Erkinheimo et al., 2003; Nabors et al., 2001).

RNA binding motif protein 3 (RBM3) is a ubiquitously expressed glycine-rich protein that can bind to both RNA and DNA via an amino-terminal RNA binding domain. RBM3 was identified as a protein expressed following cold shock and was found in the complex of proteins binding to COX-2. However, the correlation of RBM3 to COX-2, IL-8 and VEGF mRNA stability, translation and cancer progression have not been demonstrated.

Therefore, there is a need in the art for new and improved methods of preventing tumor growth, including but not limited to, methods of preventing tumor growth by targeting cancer stem cells. It is to such methods of preventing tumor growth, as well as compositions utilized in said methods, as well as methods of producing the compositions, that the presently disclosed and claimed invention is directed.

BRIEF DESCRIPTIONS OF THE DRAWINGS

This patent or application file contains at least one drawing executed in color. Copies of this patent or patent application publication with color drawing(s) will be provided by the Office upon request and payment of the necessary fee.

FIG. 1 demonstrates that Msi-1 is required for tumorigenesis. (A) Total RNA isolated from human colorectal tumors (black bars) and paired surrounding uninvolved tissue (grey bars) was reverse transcribed and subjected to real-time RT PCR for Msi-1. Error bars represent 95% confidence interval; *p<0.01. Msi-1 expression was increased in the tumors compared to uninvolved tissues. (B) HCT116 cells (6×10$^6$) were injected into nude mice to generate human colon cancer tumor xenograft, at day 15 were injected with siRNA specific for Msi-1 (si-Msi-1) or scrambled siRNA (si-scrambled) (n=5) for every 3 days as depicted in scheme (Inset figure). Length and width of palpable tumors were measured, and tumor volumes calculated at the indicated time points. Tumors excised from the mice at day 28 following 5 injections of siRNA are represented in the figure; error bars indicate SEM; asterisk p<0.05 compared to Control tumors and p<0.01 compared to scrambled siRNA treated tumors, calculated using a two-tailed student's t-test compared to control or si-scrambled treated tumors. (C) The expression of Msi-1 mRNA was demonstrated by real-time RT PCR. Shown are the levels of Msi-1 mRNA in the control, si-scrambled and si-Msi-1 treated tumors. n=5; error bars represent 95% confidence interval; *p<0.01. (D) Western blot analysis was performed on the tumors as indicated for Msi-1. n=5 of the tumors in each group. Actin was used as internal control. (E) Immunohistochemistry was performed for the tumors for Msi-1 indicated by the arrows in the inset of each tumor from each group.

FIG. 2 demonstrates that Msi-1 is essential for cell proliferation. (A) HCT116 cells transfected with 10 and 50 nM of si-Msi-1 #1, si-Msi-1 #2 or 50 nM of si-scrambled and after 48 h, RNA was isolated and subjected to real-time RT PCR for Msi-1. n=3; error bars represent 95% confidence interval; *p<0.01. (B) HCT116 cells transfected similarly for 72 h were subjected to western blot analysis for Msi-1. Shown is the representative figure of one such experiment. Actin was used as internal control. (C) HCT116 cells were transfected with 30 nM of two (#1—used in the tumor xenograft study) si-Msi-1 or si-scrambled and was subjected to hexosaminidase assay for proliferation assessment at time point indicate after 48 h after initial siRNA transfection; error bars indicate SEM; *p<0.01. (D) HT29 cells were transfected with 30 nM of si-Msi-1 #1 and proliferation was assessed at 96 h after initial siRNA transfection; error bars indicate SEM; *p<0.01.

Figure 3:
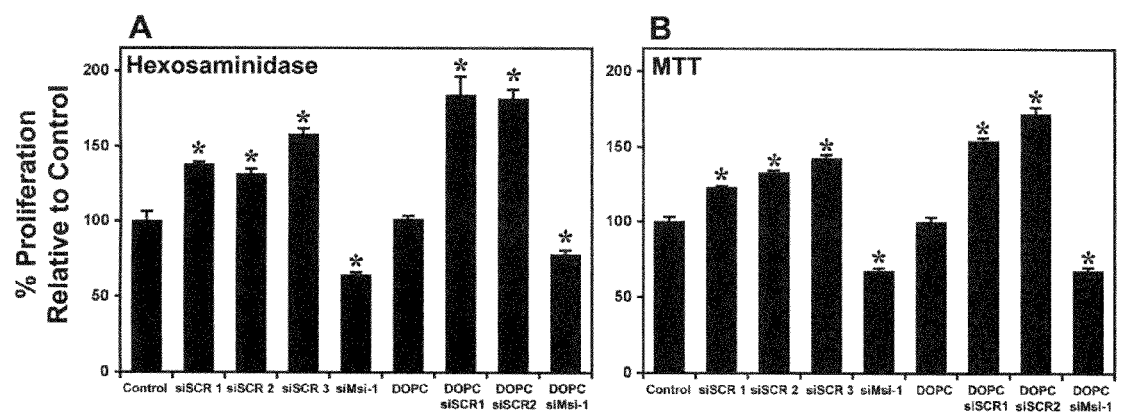

FIG. 3 demonstrates an assessment of proliferation by Hexosaminidase and MTT assays. HCT116 cells were transfected with 30 nM of si-Msi-1 or si-Scrambled as indicated using Transfectol™ transfection reagent. Scrambled and Msi-1 siRNAs were also transfected to HCT116 cells using DOPC (transfection reagent used in tumor xenografts) wherever indicated. The proliferation was assessed using hexosaminidase assay (A) and MTT assay (B). Error bars indicate SEM; *p<0.05.

Figure 4:
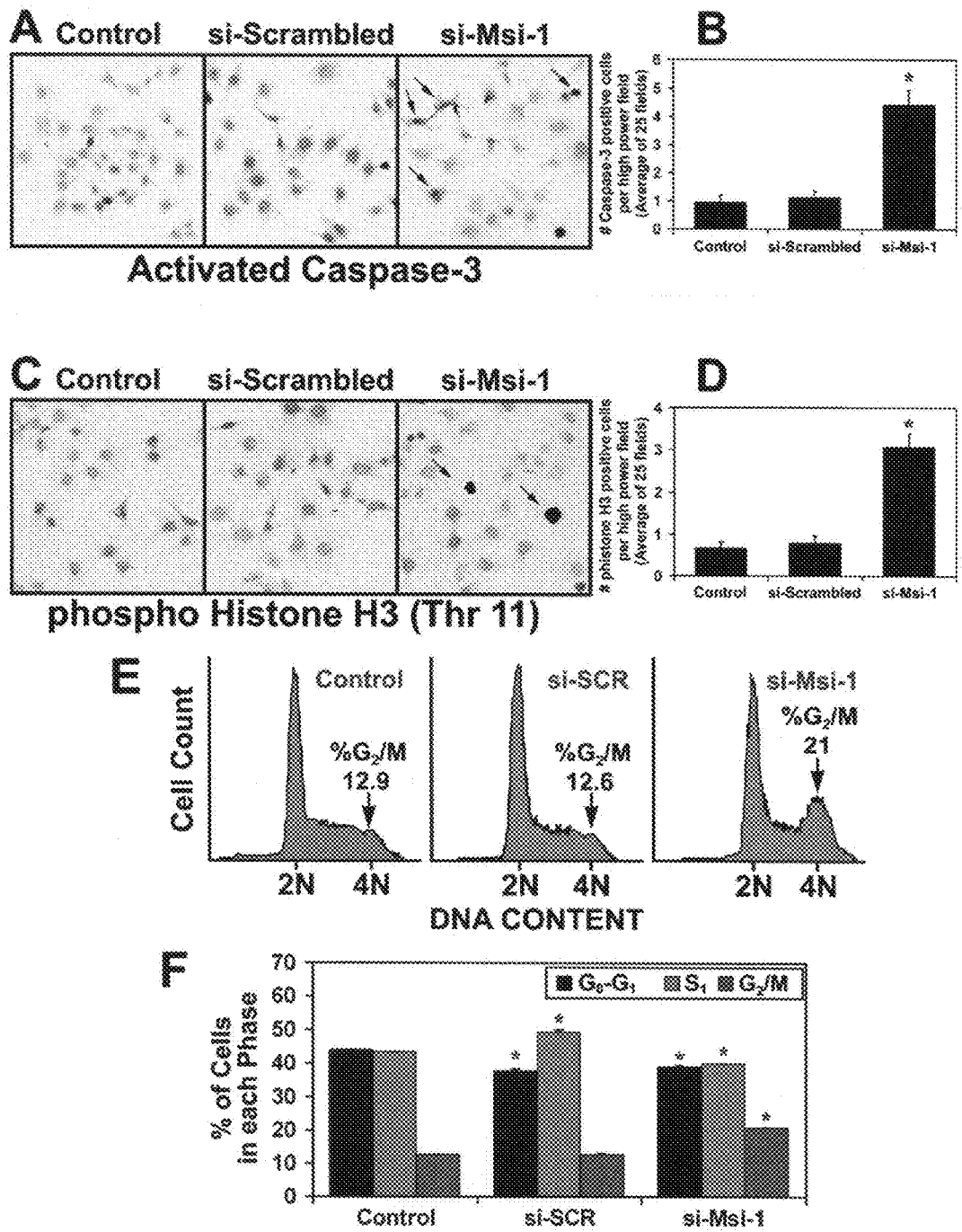

FIG. 4 demonstrates that knockdown of Msi-1 induces apoptosis and $G_2$/M arrest. (A) HCT116 cells transfected with 30 nM si-Msi-1 #1 or si-scrambled for 48 h, fixed and immunohistochemically stained for activated caspase-3. Caspase-3 positive cells are indicated by the arrows. (B) Caspase-3 positive cells counted were plotted as an average of 25 high power fields. Error bars indicate the SEM; *p<0.01. (C) siRNA transfected cells as indicated is stained for phosphorylated histone H3 (Thr 11). Phosphorylated Histone H3 positive cells are indicated by the arrows and cells counted are plotted as a bar graph (D) as an average of 25 high power fields. Error bars indicate the SEM; *p<0.01. (E) HCT116 cells were transfected with 30 nM si-Msi-1 or si-scrambled and was subjected to FACS analysis. Representative cell cycle profile for each treatment as indicated. 2N represents $G_0$-$G_1$ phase and 4N represents $G_2$/M phase. (F) Graphical representation of the fractions of each phase. Error bars indicate the SEM; *p<0.01.

Figure 5:
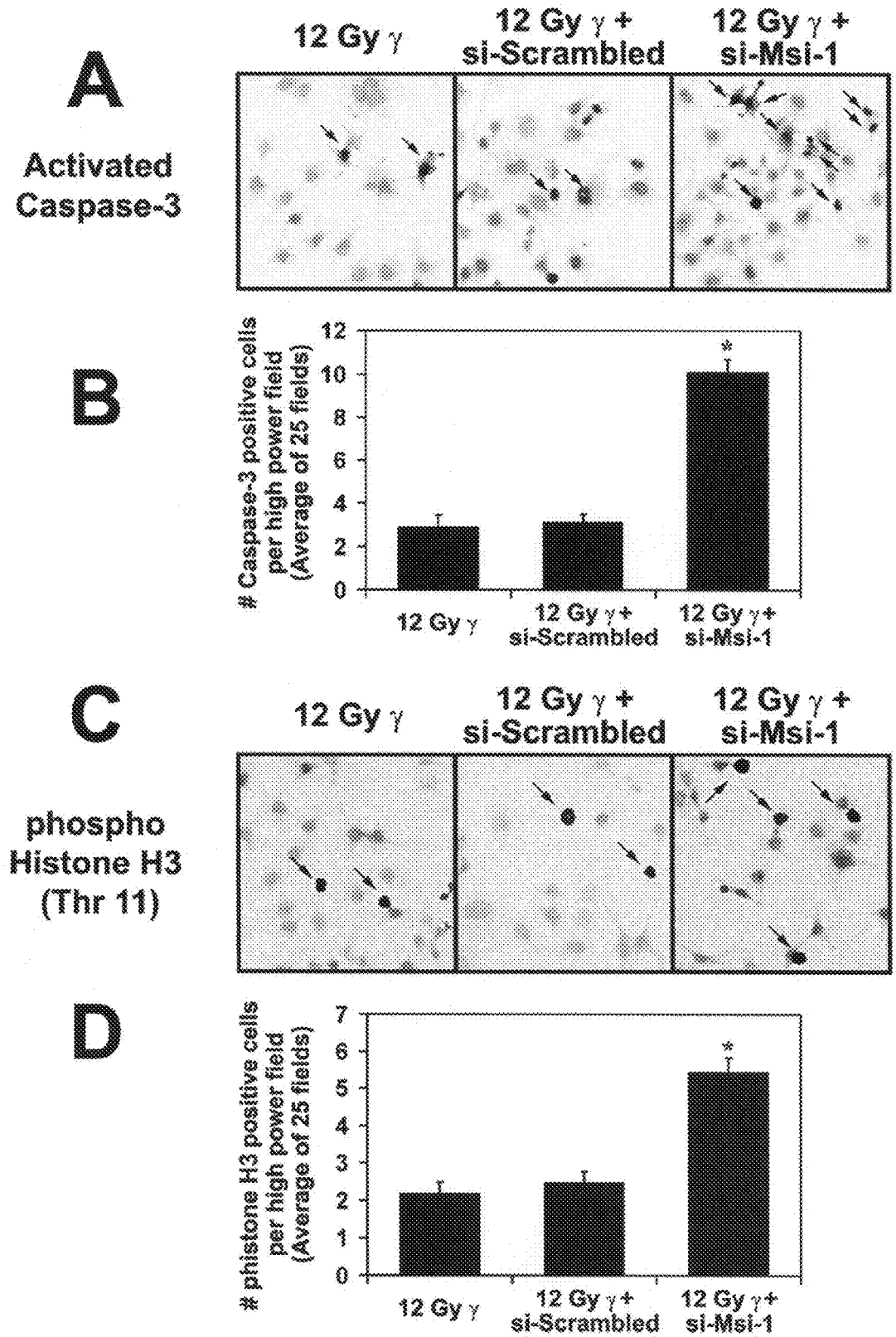

FIG. 5 demonstrates that knockdown of Msi-1 augments radiation induced apoptosis. HCT116 cells transfected with 30 nM si-Msi-1 #1 or si-scrambled for 48 h was subjected to 12 Gy γ-radiation. Then the cells were fixed and stained for activated caspase-3 (A) The cells positive for activated caspase-3 indicated by the arrows were quantified and represented as an average of 25 high power fields (B) Error bars indicate the SEM; *p<0.01. (C) The siRNA transfected cells followed by radiation were subjected to staining for phosphorylated histone H3. The cells positive for phosphorylated histone H3 are indicated by the arrows. (D) The cells quantified are represented as an average of 25 high power fields. Error bars indicate the SEM; *p<0.01.

Figure 6:
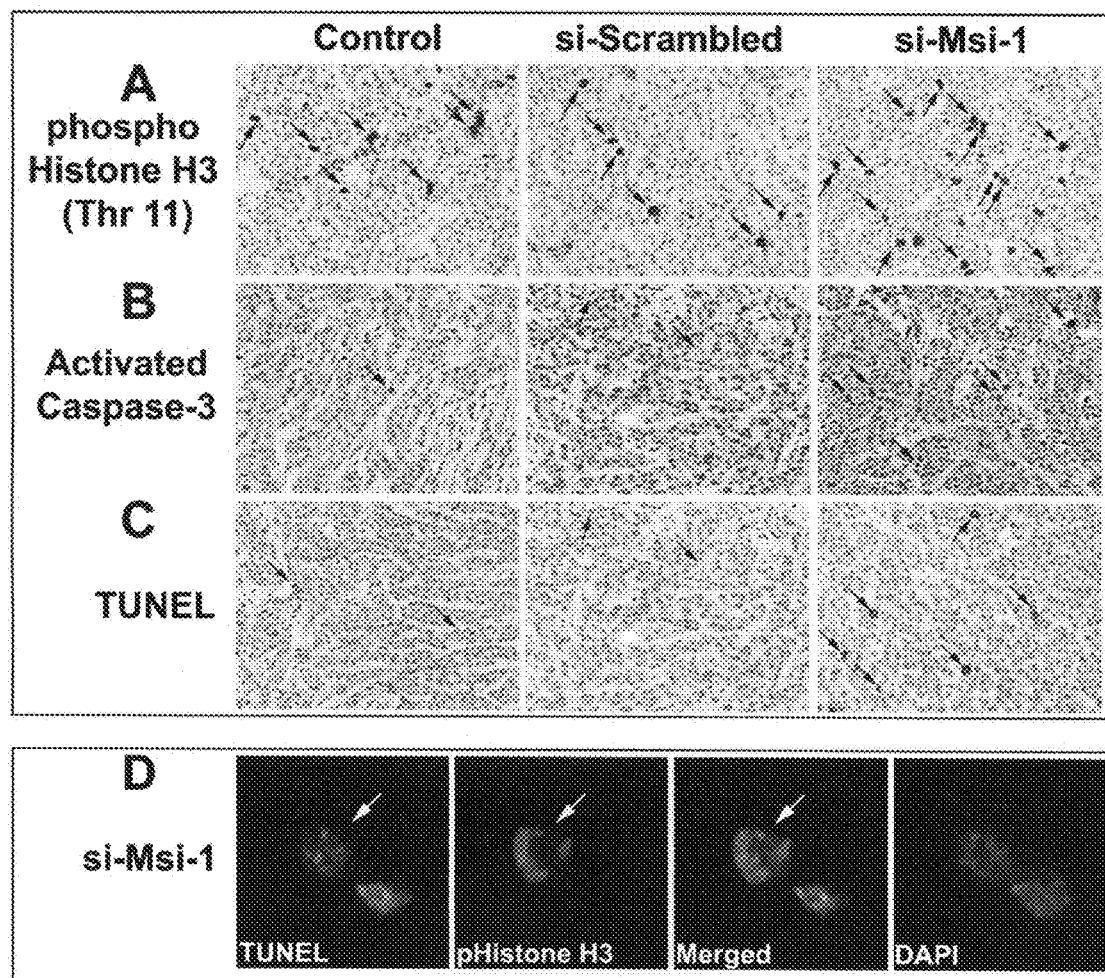

FIG. 6 demonstrates that knockdown of Msi-1 leads to mitotic catastrophe in the tumors. The control, si-scrambled or si-Msi-1 treated tumors were subjected to immunohistochemical staining for phosphorylated histone H3 (A), activated caspase-3 (B), TUNEL (C). The cells positive for the above are indicated by the arrows in the particular photograph. (D) si-Msi-1 treated tumors were subjected to immunofluorescence staining for TUNEL (Green) and phosphorylated histone H3 (Red). The cell positive for TUNEL and phosphorylated histone H3 in the merged image is indicated by the arrow. The nucleus was stained with DAPI.

FIG. 7 demonstrates that downregulation of Msi-1 leads to increased mitosis and apoptosis. (A) Msi-1 siRNA treated tumor xenografts co-stained for Msi-1 and phosphorylated histone H3 demonstrate that cells positive for phosphorylated histone H3 (Green) is negative for Msi-1 (Red). Nucleus was stained with Hoechst 33342 (Blue). (B) The cells positive for TUNEL (Green) are negative for Msi-1 (Red) in the tumor xenografts stained with Hoechst 33342 (Blue).

FIG. 8 demonstrates that siRNA mediated knockdown of Msi-1 leads to a decrease in Notch-1 and increase in $p21^{WAF1}$. The control (A), scrambled siRNA treated (B) and Msi-1 siRNA treated (C) tumors were stained for Notch-1. The brown staining demonstrate cells positive for Notch-1. The arrow in the control or tumors treated with scrambled siRNA indicates a representative cell positive for cytoplasmic and nuclear Notch-1. The tumors treated with Msi-1 siRNA demonstrated a loss of Notch-1 staining. (D) HCT116 cells were transfected with (10 and 50 nM) of Msi-1 siRNA or with 50 nM of scrambled siRNA for 72 h. The cells were lysed and subjected to western blot analyses for Notch-1. The representative blot shown demonstrates decreased Notch-1 and cleaved Notch-1 expression in the cells treated with si-Msi-1 compared to control or si-scrambled treated HCT116 cells. Actin was used as loading control. Control transfection reagent (E), scrambled siRNA treated (F) and Msi-1 siRNA treated (G) tumors were stained for $p21^{WAF1}$. The brown staining demonstrate cells positive for $p21^{WAF1}$. The arrow in the control tumors or tumors treated with scrambled siRNA indicates a representative cell positive for $p21^{WAF-1}$. The tumors treated with Msi-1 siRNA demonstrated increased expression of $p21^{WAF-1}$ immunostaining. (H) Control, scrambled siRNA and Msi-1 siRNA treated tumor xenografts were lysed and subjected to western blot analyses for $p21^{WAF-1}$. The representative blot shown demonstrates increased $p21^{WAF-1}$ expression in the cells treated with si-Msi-1 compared to control or si-scrambled treated tumor xenografts. Actin was used as loading control.

Figure 9:
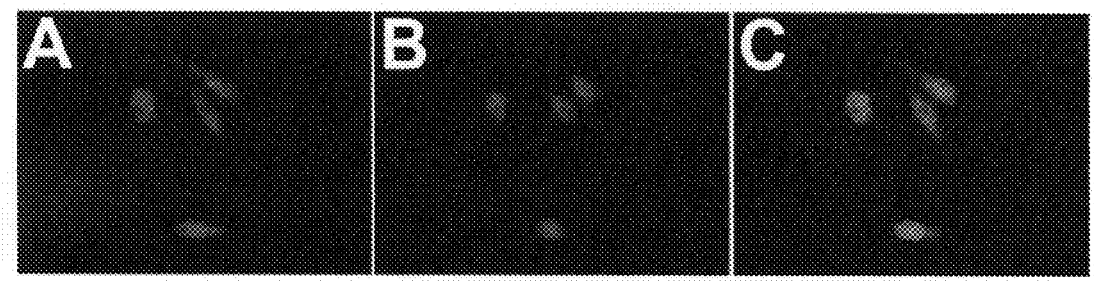

FIG. 9 demonstrates expression of CD133/AC133 in HCT116 cells. HCT116 cells were immunostained for CD133/AC133 antibody. The cells positive for CD133/AC133 are stained red (A). The nucleus was stained using Hoechst 33342 (blue) (B). (C) Merged image of (A) and (B).

Figure 10:
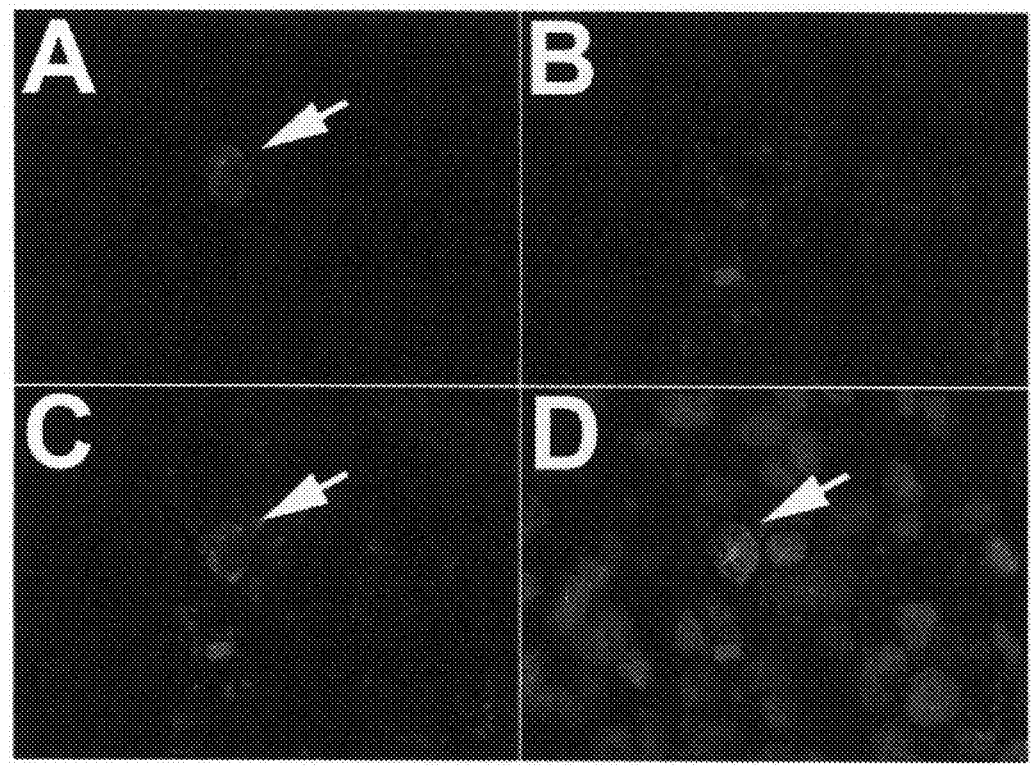

FIG. 10 demonstrates expression of CD133/AC133 in tumor xenograft. The control tumor xenograft was immunohistologically stained for Msi-1 (green) indicated by the arrow (A), CD133/AC133 (red) (B). (C) Cell positive for both Msi-1 and CD133/AC133 is indicated by the arrow in the merged image of (A) and (B). (D) Merged image of (A) (B) and (C), the cell positive for Msi-1, CD133/AC133 is indicated by the arrow.

Figure 11:
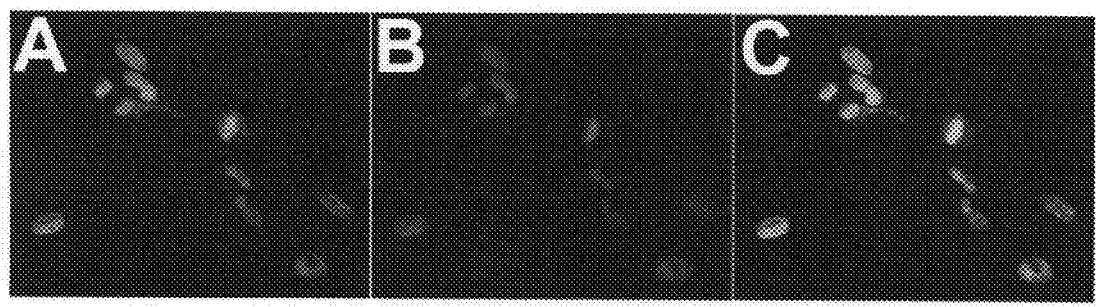

FIG. 11 demonstrates expression of Msi-2 in HCT116 cells. HCT116 cells were immunostained for Msi-2 antibody. The cells positive for Msi-2 are stained green (A). The nucleus was stained using Hoechst 33342 (blue) (B). (C) Merged image of (A) and (B).

Figure 12:
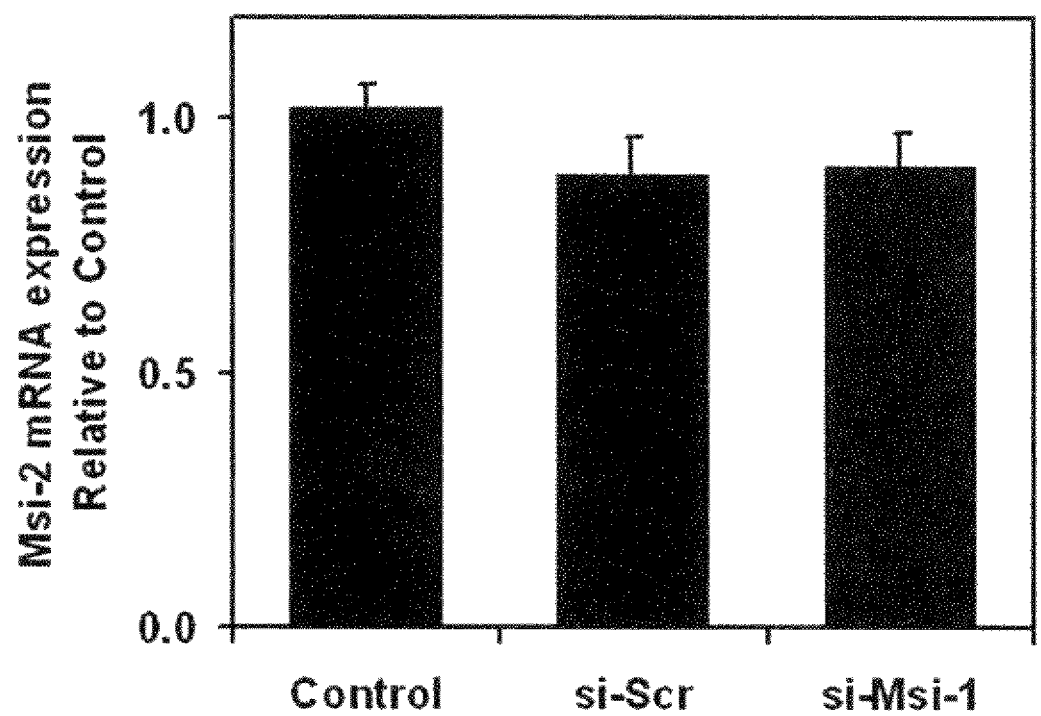

FIG. 12 demonstrates expression of Msi-2 in tumor xenograft. Total RNA isolated from control, scrambled siRNA and Msi-1 siRNA treated tumor xenografts was subjected to real-time RT PCR for Msi-2. n=5; error bars represent 95% confidence interval.

Figure 13:
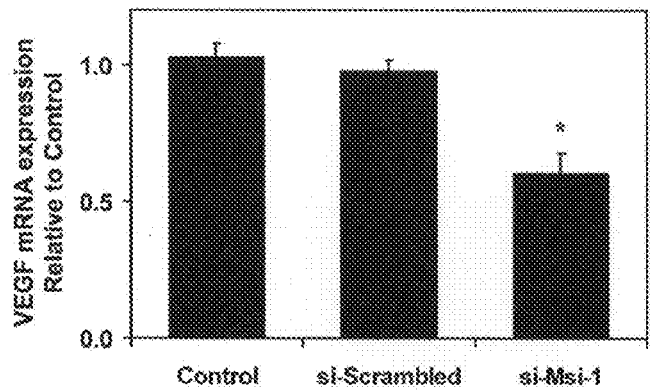

FIG. 13 demonstrates that siRNA mediated knockdown of Msi-1 results in downregulation of VEGF in HCT116 tumor xenografts compared to Control or si-scrambled treated tumors. *p=0.05.

Figure 14:
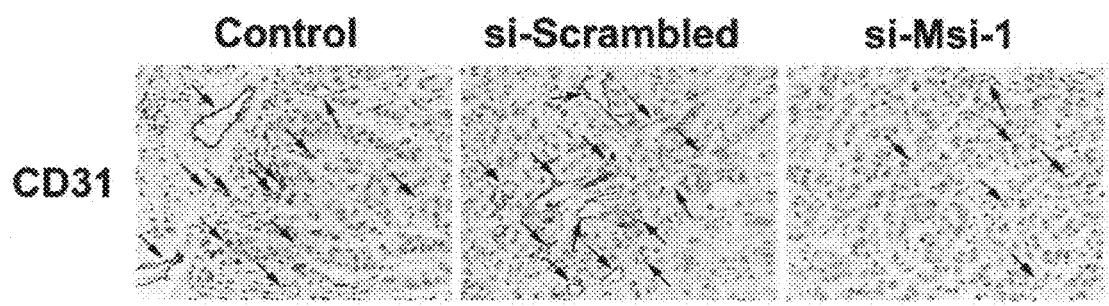

FIG. 14 demonstrates that lack of msi-1 leads to reduction of angiogenesis in the tumors. The control untreated, si-scrambled or si-Msi-1 treated tumors were subjected to immunohistochemical staining for CD31. The cells positive for CD31 are indicated by the arrows.

Figure 15:
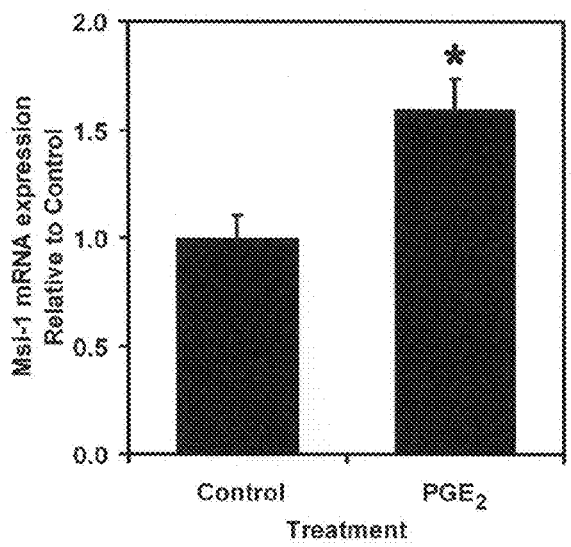

FIG. 15 demonstrates that $PGE_2$ induces Msi-1. HCT116 cells were treated with $PGE_2$, and total RNA isolated was subject to real-time RT PCR for Msi-1 mRNA expression. Following treatment with $PGE_2$, 1.6 fold increase in Msi-1 mRNA was observed. *p=0.05.

Figure 16:
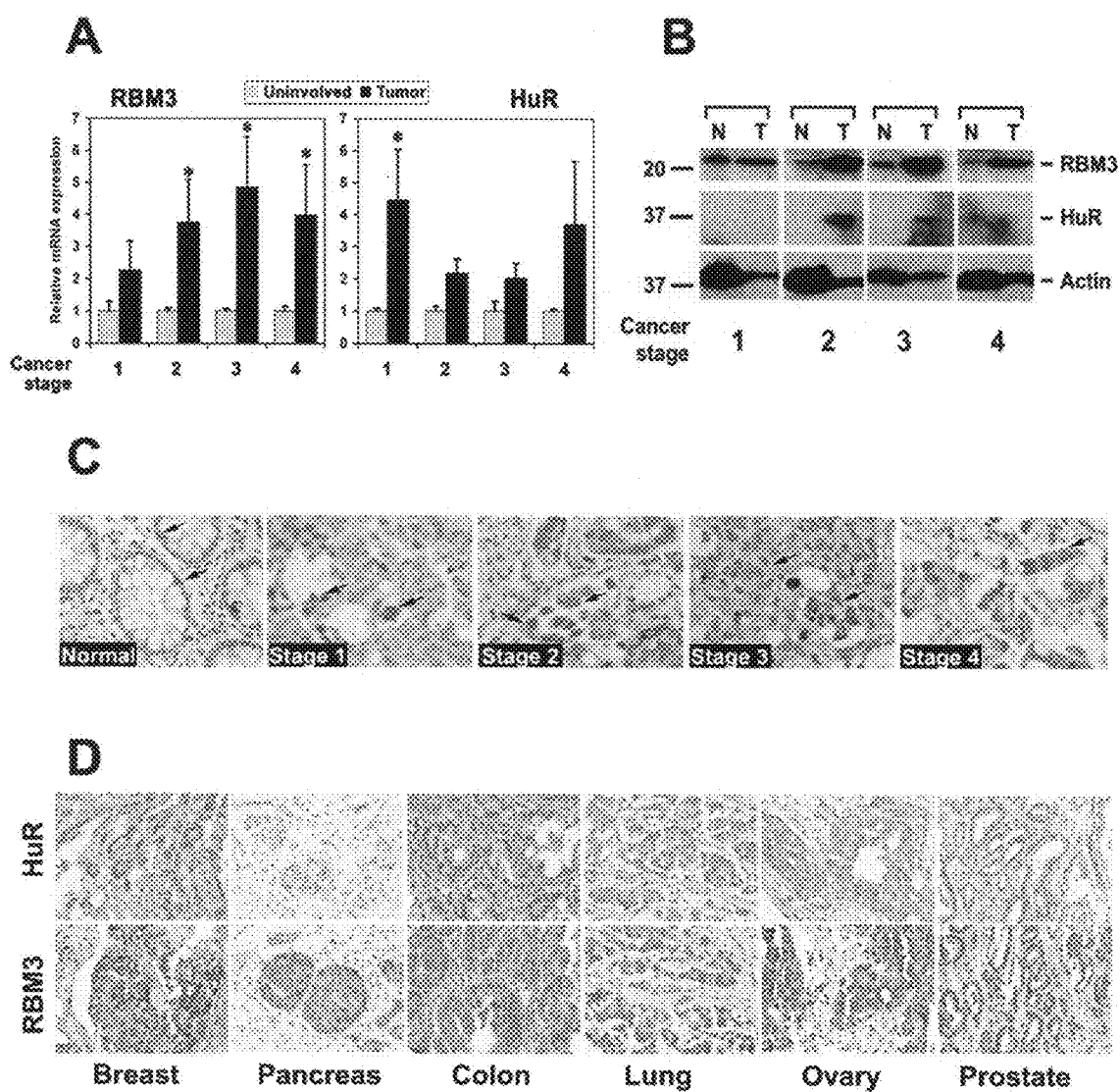

FIG. 16 demonstrates that RBM3 is a binding partner of HuR and is overexpressed in colon cancer. (A) RBM3 and HuR gene expression in tumor and surrounding uninvolved tissues. Significant induction of RBM3 mRNA expression was observed in stages 2-4, while HuR was induced only in stage 1. Asterisks denote statistically significant differences ($*p<0.01$). (B) Western blot analyses of total tissue extracts for RBM3 and HuR. Actin was determined as control for gel loading. RBM3 expression is significantly upregulated in the tumors. (C) Immunohistochemistry for RBM3 in normal and colon cancer tissues. Brown stain demonstrates the location of the RBM3 protein in the tissues. (D) Immunohistochemistry for HuR and RBM3 in various human tumors. Brown stain shows the location of the protein.

FIG. 17 demonstrates increased expression of RBM3, HuR and COX-2 mRNA in human colorectal tumors. Abbreviations—Pt—Patient; NOS—not otherwise specified. a. Patient ID number. b. All the colorectal cancer tumors were adenocarcinomas. c. Stage of cancer. d. Staging code from the American Joint Committee on Cancer staging (AJCC). These symbols were provided for most specimens in the accompanying material supplied by the Siteman Cancer Center. '-' in the column indicates that the staging symbol was not provided for the indicated patients. e. Real Time PCR for RBM3, COX-2 and HuR. Values in the column indicate expression of mRNA in tumor samples relative to paired uninvolved tissues. ?-actin was used as internal control for normalization for all the Real Time PCR analyses.

Figure 18:
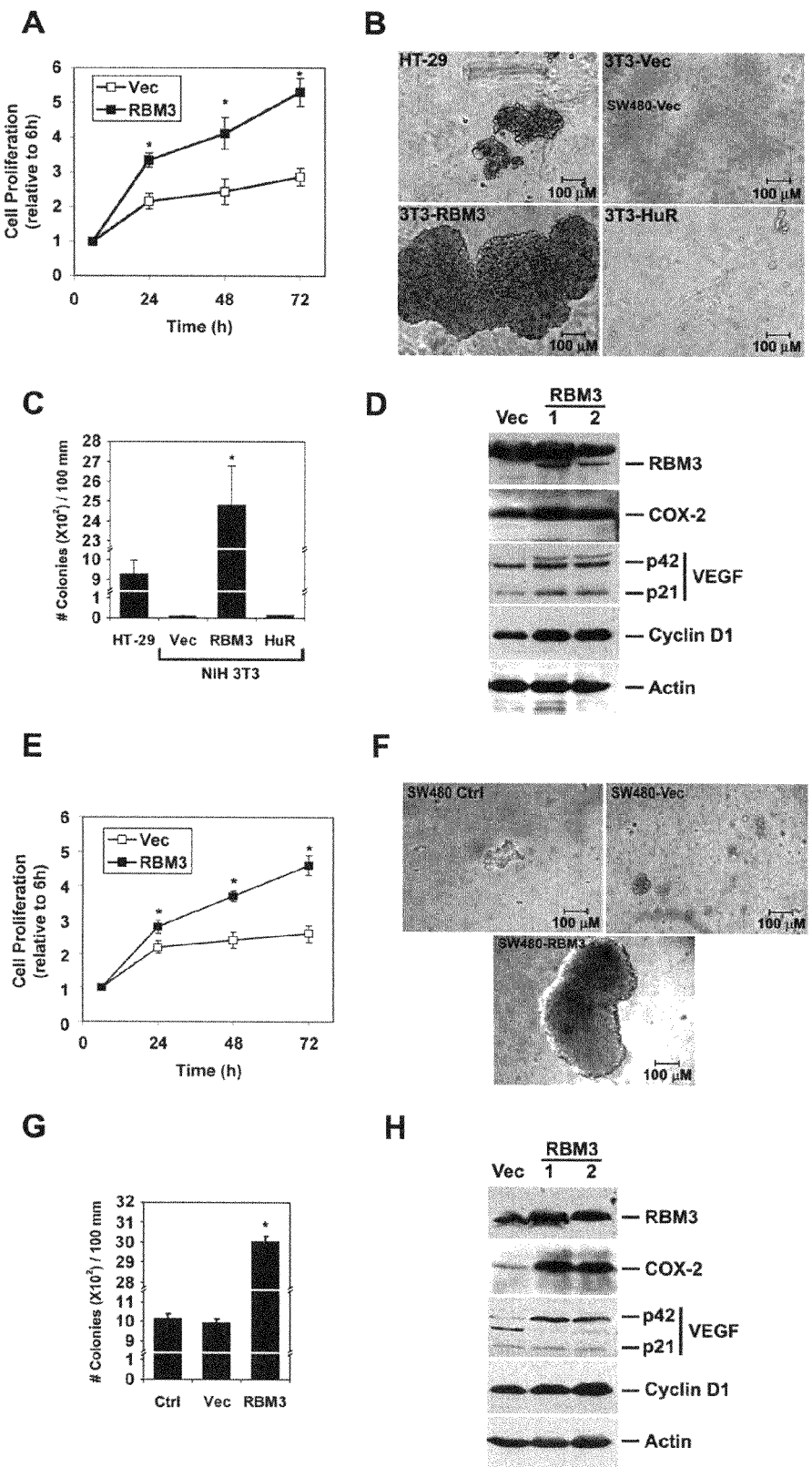

FIG. 18 demonstrates that RBM3 overexpression induces oncogenic transformation. (A) Proliferation of the NIH3T3-RBM3 clones was significantly higher than that observed with NIH3T3-vector clones. (B) NIH-3T3-RBM3 cells develop large colonies in soft agar, which are bigger than those formed by HT-29 cells. HuR overexpressing cells, on the other hand did not form any colonies in the soft agar. (C) Quantitative estimation of number of colonies formed in soft agar. $*p<0.01$. (D) Two clones of NIH3T3 cells stably expressing RBM3 were selected based on western blot analyses. Expression of COX-2, VEGF and cyclin D1 increases in the RBM3 overexpressing cells. (E) Proliferation of the SW480-RBM3 clones was significantly higher than that observed with SW480-vector clones. (F) SW480-RBM3 cells develop large colonies in soft agar, when compared to control, untransfected or vector transfected cells. (G) Quantitative estimation of number of colonies formed in soft agar. $*p<0.01$. (H) Two clones of SW480 cells stably expressing RBM3 were selected based on western blot analyses. Expression of COX-2, VEGF and cyclin D1 increases in the RBM3 overexpressing cells.

Figure 19:
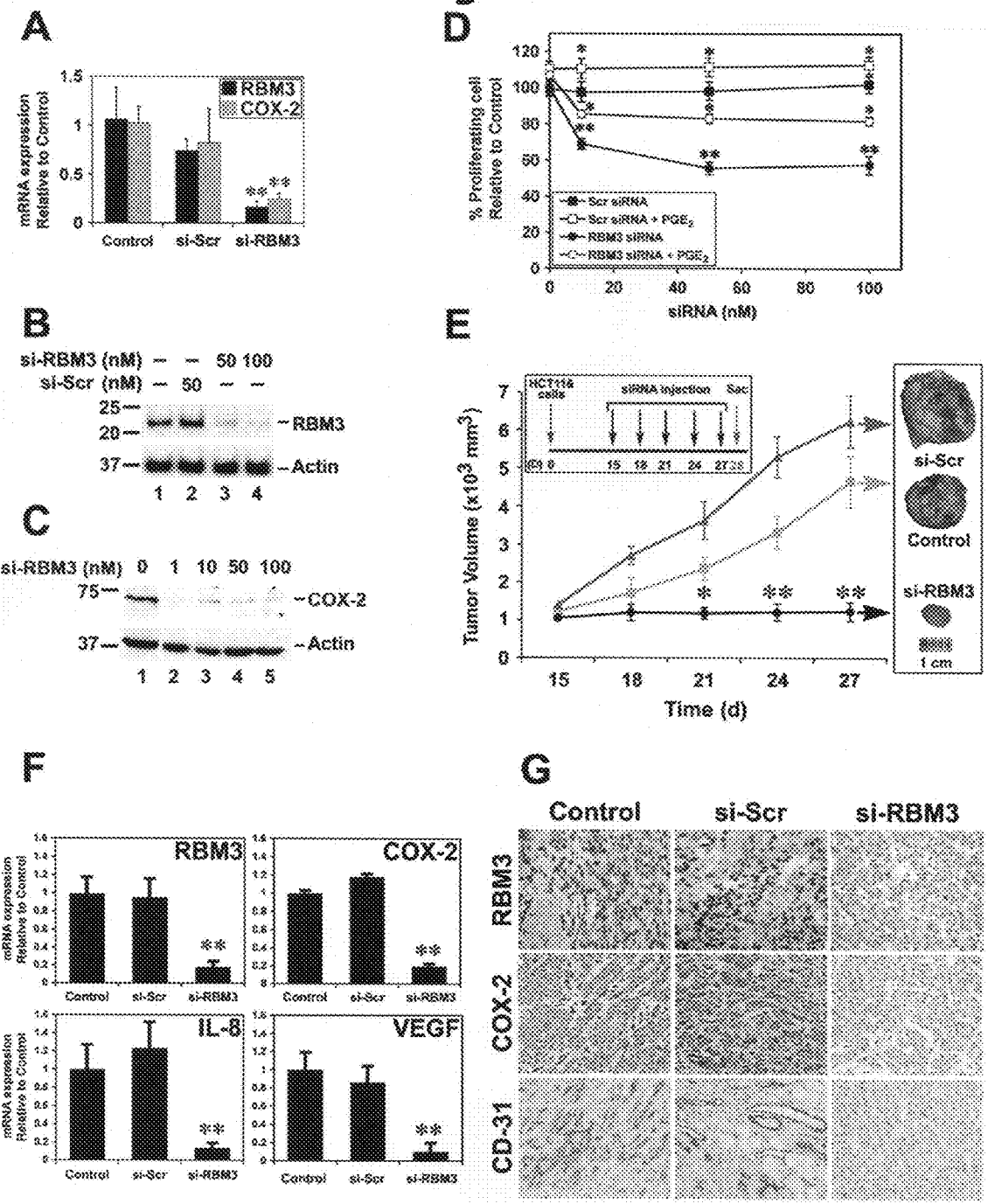

FIG. 19 demonstrates that RBM3 is essential for tumor growth. (A) RBM3 specific siRNA (si-RBM3), but not a scrambled siRNA (si-Scr) decreases RBM3 and COX-2 mRNA expression. Asterisks denote statistically significant differences ($**p<0.01$). (B, C) RBM3 and COX-2 protein were significantly reduced in the cell treated with RBM3-targeted siRNA. (D) Knockdown of RBM3 expression decreases colon cancer cell proliferation. HCT116 cells were transfected with increasing doses (0-100 nM) of either RBM3-specific or scrambled (Scr) siRNA, and also treated with $PGE_2$ after 48 h. Cells transfected with RBM3-specific siRNA demonstrated significant reduction in proliferation, which was rescued in the presence of $PGE_2$. Asterisks denote statistically significant differences ($*p<0.05$, $**p<0.01$). (E) Antitumor activity of si-RBM3 in mice carrying HCT116 cell tumor xenografts. HCT116 cells were injected into the flanks of Ncr nude mice and tumors were allowed to develop for 15 d. siRNA was injected directly into the tumors starting on day 15 and every third day for a total of five injections. Tumor sizes with standard error are shown from data collected at the time of every injection. si-Scr treated tumors were larger than the control carrier injected tumors, while si-RBM3 treated tumors were smaller. A representative excised tumor at d 28 is shown to the right. Asterisks denote statistically significant differences ($*p<0.05$ and $**p<0.01$). (F) Decreased gene expression in the si-RBM3 injected tumors. Real Time RT-PCR was performed with total RNA from the tissues and the expression of RBM3, COX-2, IL-8 and VEGF is plotted as relative to control, carrier injected tumors. ($*p<0.01$). (G) Immunohistochemistry for RBM3, COX-2 and CD31 in HCT116 xenografts. Data shows that there is complete suppression of RBM3 and COX-2 expression and decreased microvessel density.

Figure 20:
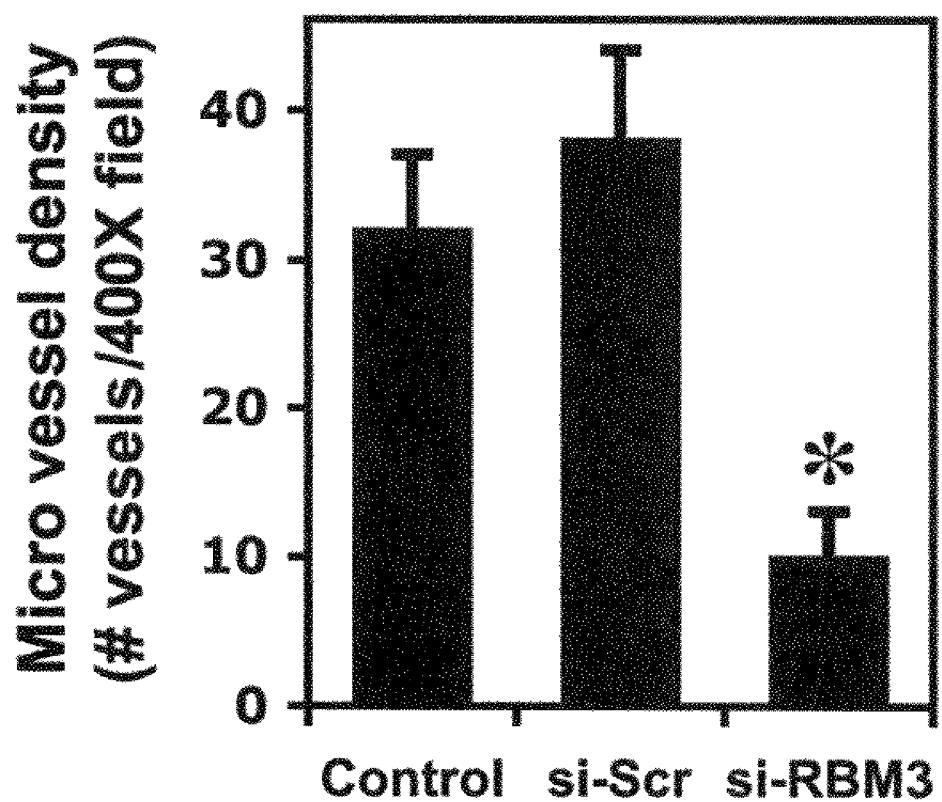

FIG. 20 demonstrates decreased angiogenesis in si-RBM3 administered HCT-116 tumor xenografts. Formalin fixed paraffin embedded tumor xenograft tissues were immunostained for CD31 to detect the endothelial cells that line the blood vessels. The number of blood vessels in the various conditions were counted and graphed. Graph represents the average number of blood vessels per 400× field. ($*p<0.01$).

Figure 21:
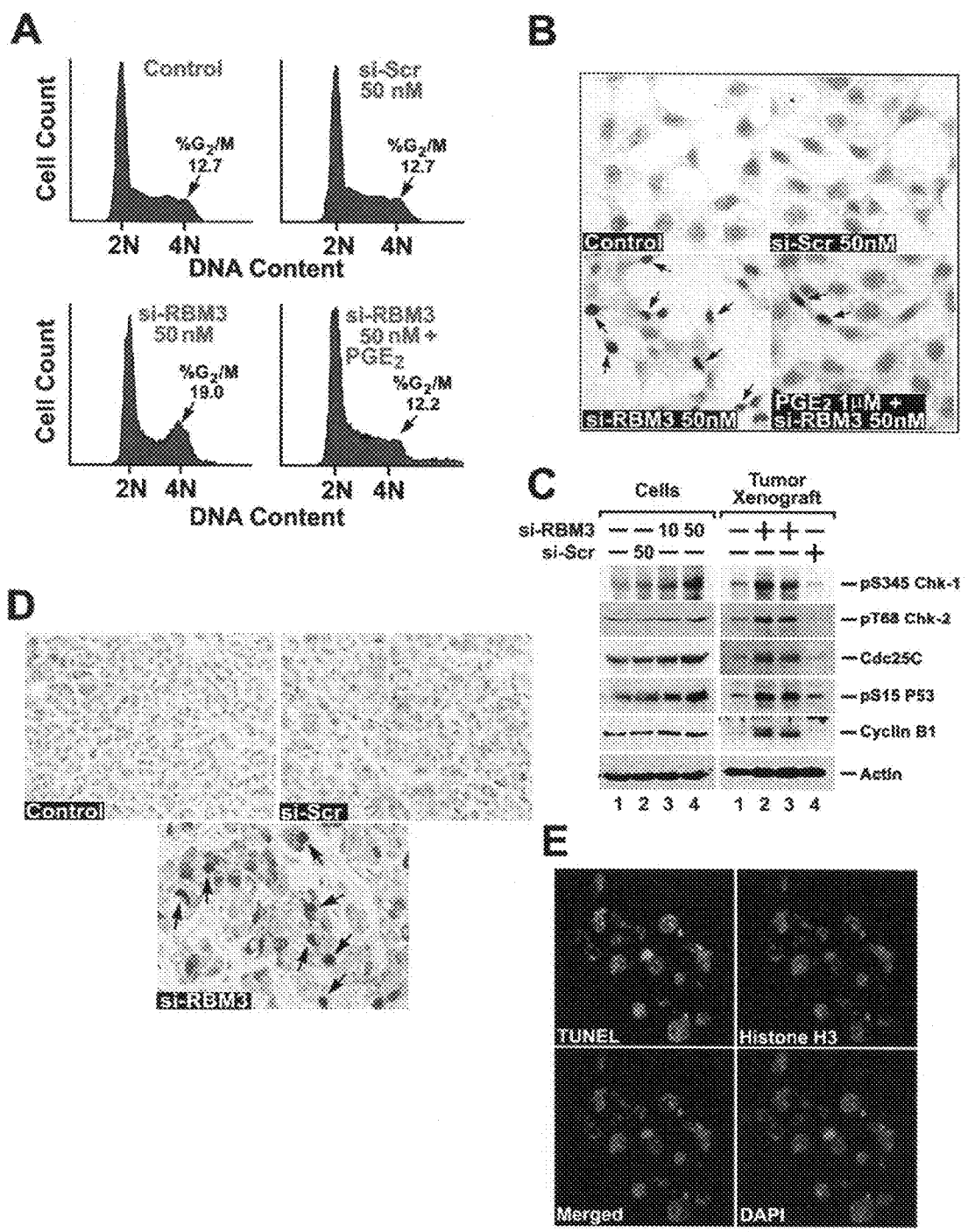

FIG. 21 demonstrates that RBM3 downregulation results in mitotic catastrophe. (A) siRNA downregulation of RBM3 increased cells in the $G_2$/M phase. HCT116 cells were transfected at the indicated dose of either scrambled (si-Scr) or RBM3-specific (si-RBM3) siRNA for 72 h. Cell-cycle profiles were analyzed by FACS using PI staining for DNA content. The percentage of cells in the $G_2$/M phase following si-RBM3 transfection was increased compared to control and si-Scr cells. Addition of $PGE_2$ partially suppressed the RBM3 siRNA mediated effects. (B) Knockdown of RBM3 leads to apoptosis. HCT116 cells following siRNA transfection were stained by the TUNEL method. Arrows show the TUNEL positive cells found in si-RBM3 transfected cells, but less in cells also treated with $PGE_2$. (C) Loss of RBM3 induces checkpoint proteins. Lysates from HCT116 cells treated with scrambled (si-Scr, 50 nM) or RBM3-specific (si-RBM3, 10, 50 nM) siRNA, and tumor xenografts from the various treatments were subjected to western blot analyses using specific antibodies for phospho-Ser345 Chk-1, phospho-Thr68 Chk-2, Cdc25C, phospho-Ser15 p53 and cyclin B1. Actin was used as internal control for loading the gels. (D) Lack of RBM3 increases cyclin B1 translocation to nucleus. Tumor xenografts were subjected to immunohistochemical staining for cyclin B1. The arrows in the si-RBM3 treated tumors indicate cyclin B1 positive cells in the nucleus. (E) RBM3 depletion leads to mitotic catastrophe. Tumors treated with si-RBM3 were stained for TUNEL (green) and Histone H3 (red). The cells positive for both are shown in the merged image with yellow stain. DAPI is used to stain the nucleus.

Figure 22:
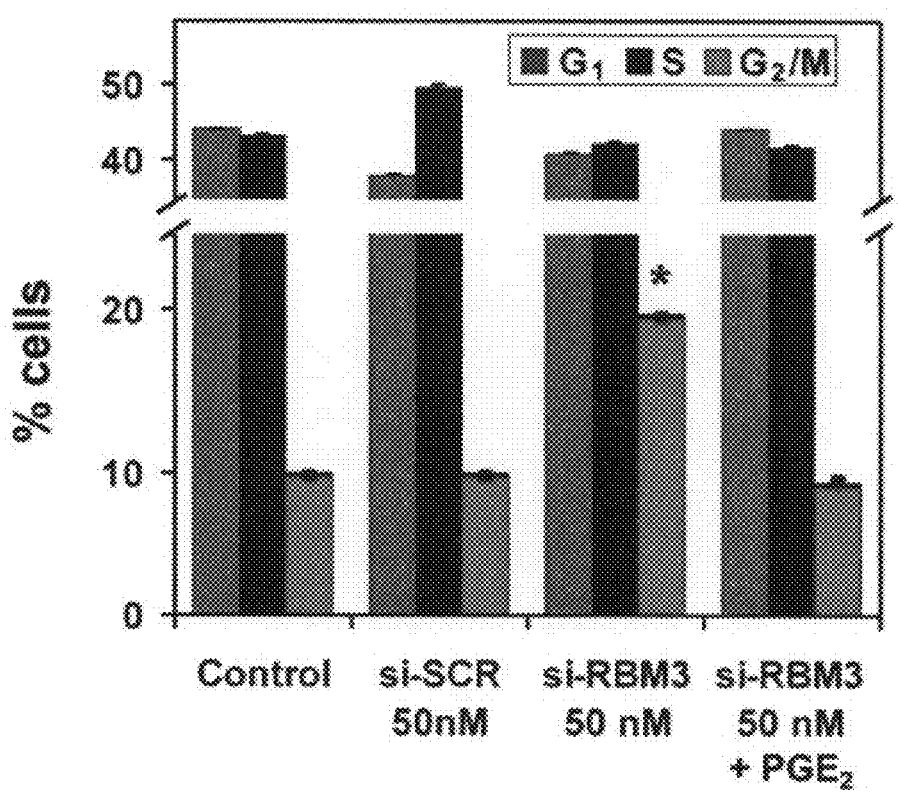

FIG. 22 demonstrates that depletion of RBM3 increases the number of cells in $G_2$/M phase of cell cycle. Control HCT116, si-Scr, si-RBM3 and si-RBM3 followed $PGE_2$ treated cells were subjected to FACS analysis. The graph represents the percent of cells in each phase. Asterisks denote statistically significant differences (p<0.01 when compared with control or scrambled).

Figure 23:
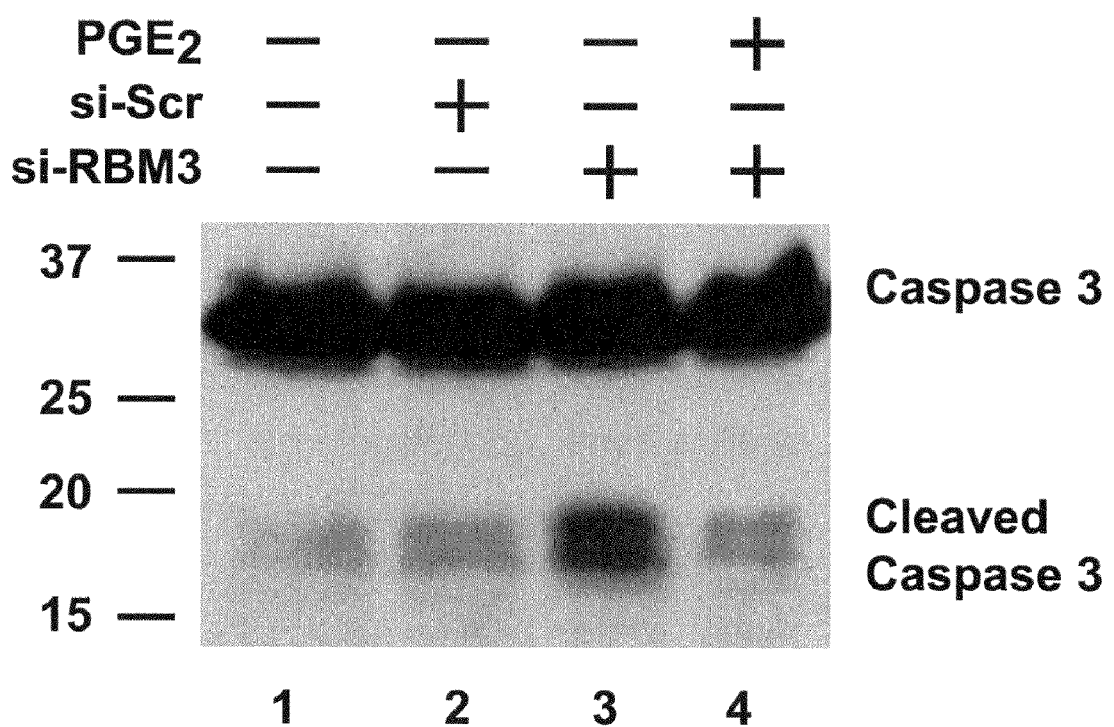

FIG. 23 demonstrates that $PGE_2$ treatment suppresses the apoptosis induced following silencer RNA mediated reduction of RBM3. Western blot analysis for caspase 3 following transfection of si-RBM3 demonstrates increased caspase 3 activation. (17 and 32 kDa in size) due to downregulation of RBM3 expression. In contrast, treatment with 1 µM $PGE_2$ results in inhibition of caspase activation even when RBM3 expression is suppressed.

Figure 24:
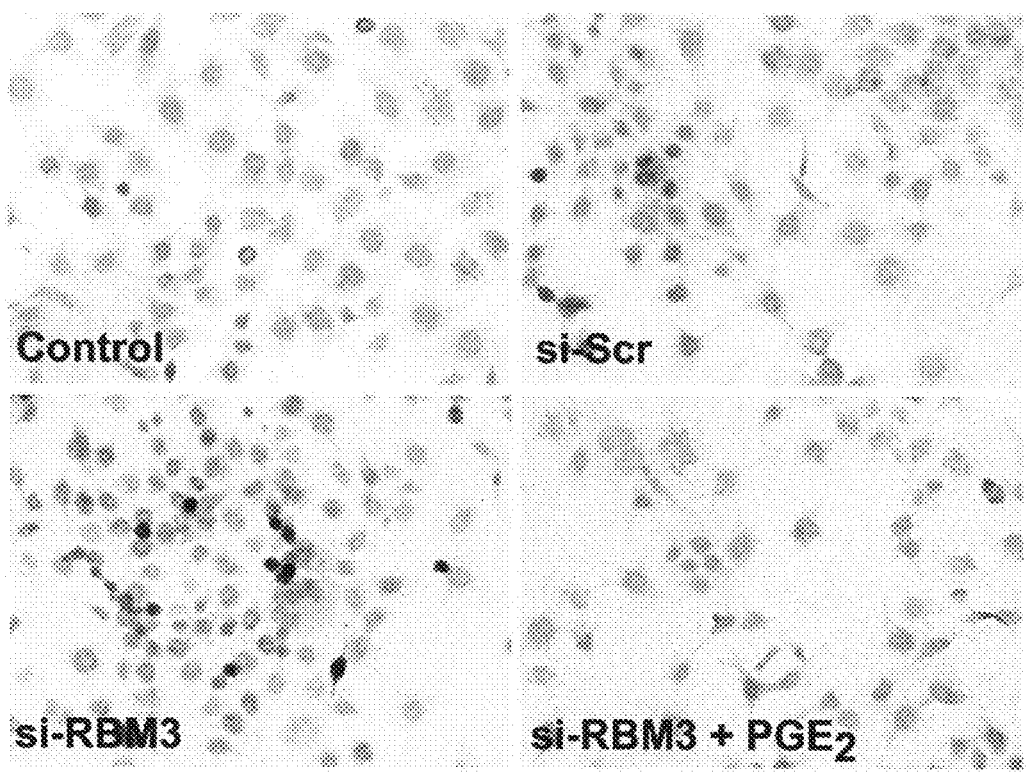

FIG. 24 demonstrates that $PGE_2$ treatment inhibits apoptosis induced by suppression of RBM3 expression. HCT116 cells transfected with si-RBM3 was incubated with 1 µM $PGE_2$ and then levels of caspase 3 was determined by immunocytochemistry. Inhibition of RBM3 demonstrated high levels of apoptosis cells (arrow), which was reduced when cells were also incubated with $PGE_2$.

Figure 25:
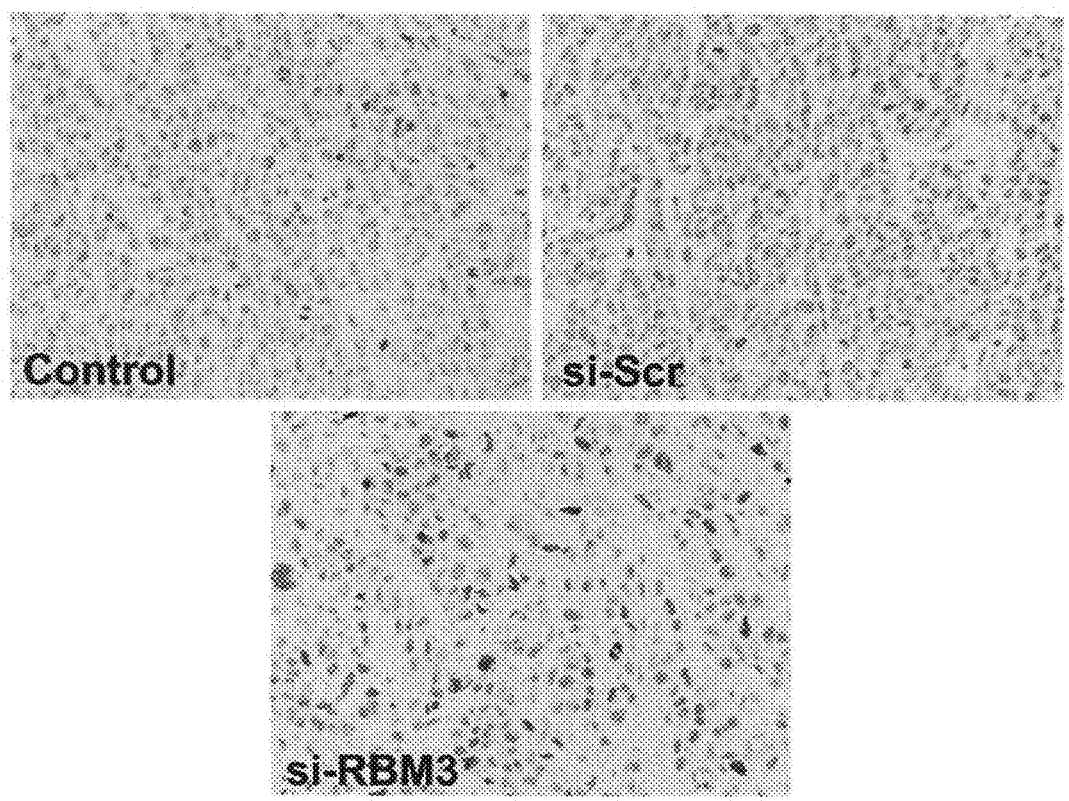

FIG. 25 demonstrates high levels of phospho-H2AX expression following suppression of RBM3 expression. HCT116 cell tumor xenografts treated with si-RBM3 to inhibit RBM3 expression demonstrated high levels of phospho-H2AX expression as compared to si-Scr treated tumors.

Figure 26:
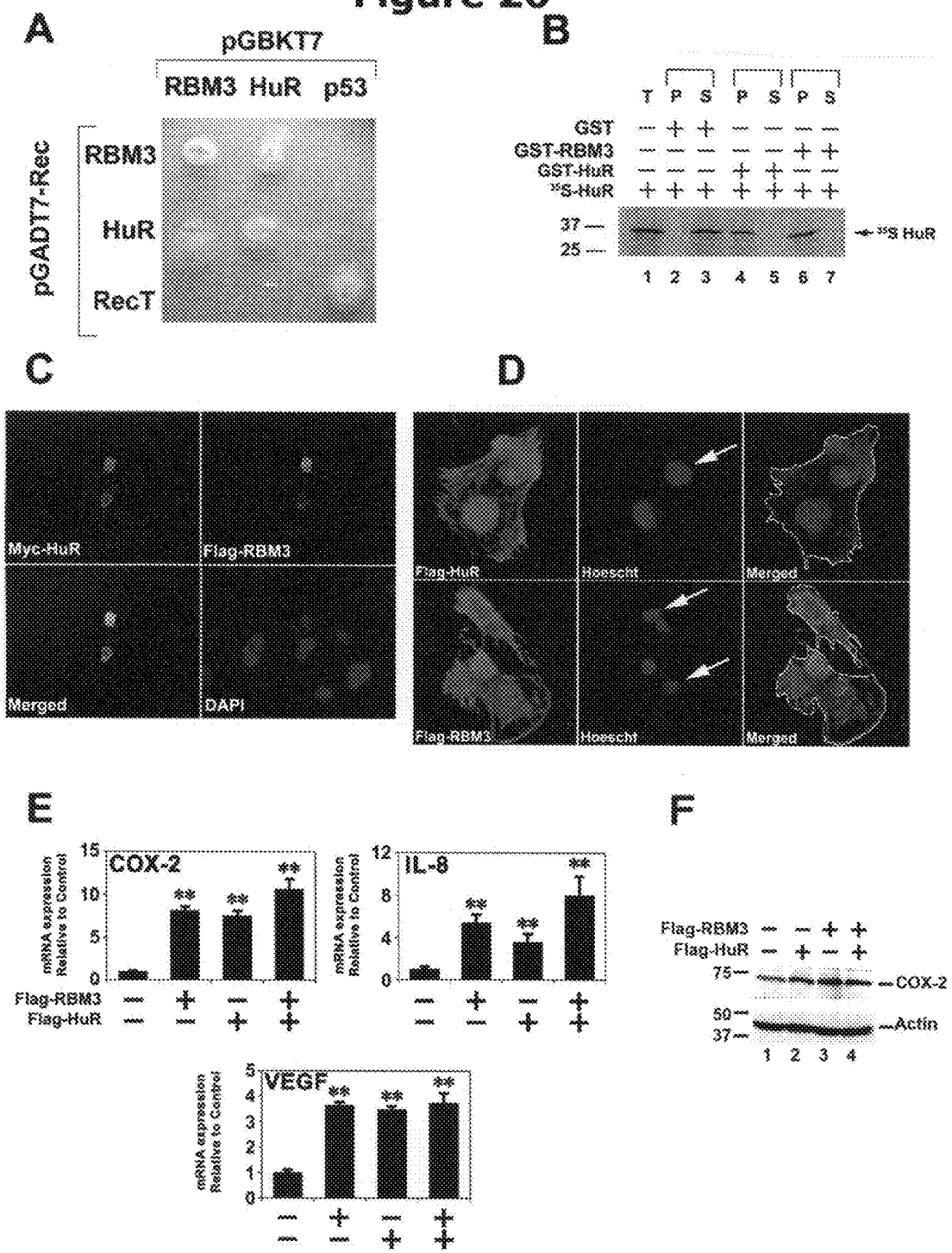

FIG. 26 demonstrates that RBM3 and HuR interact and enhance stability. (A) Yeast two-hybrid interaction of RBM3 with HuR. RBM3 and HuR expressed as bait and test proteins interact in the yeast by the colonies formed on quadruple dropout media. Breakdown of the X-?-gal results in a blue colony. Tumor suppressor protein p53 and SV40 T antigen (RecT) were used as positive control for interaction, but negative for interaction with either RBM3 or HuR. (B) GST pull-down assay. $^{35}$S-methonine labeled in vitro translated HuR ($^{35}$S-HuR) was incubated with either GST-RBM3 or GST-HuR. The GST-proteins were immobilized on to glutathione sepharose beads. The immobilized proteins were separated and separated in a SDS-PAGE gel and subjected to phosphorimager analyses. Pure GST served as negative control. (C) Colocalization of HuR and RBM3. HeLa cells were transiently transfected with plasmids expressing myc-epitope tagged HuR and FLAG-epitope tagged RBM3. Immunocytochemistry was performed for the myc and FLAG epitopes. Images for the HuR and RBM3 were merged demonstrating colocalization. Nucleus was stained by DAPI. (D) Nuclear-cytoplasmic shuttling of HuR and RBM3. Plasmids encoding FLAG-epitope tagged HuR or RBM3 were transiently transfected into human HeLa cells and subsequently fused with mouse NIH-3T3 cells. The proteins were immunostained for the FLAG tag, and the nuclei by Hoescht stain to differentiate human and mouse nuclei. Mouse nuclei, seen as punctuate staining are denoted by an arrow. (E) RBM3 and HuR induce COX-2, IL-8 and VEGF mRNA expression. Ectopic expression of Flag epitope-tagged RBM3 and HuR resulted in significant increase in endogenous COX-2 mRNA (left panel), IL-8 mRNA (middle panel) and VEGF mRNA (right panel) in HCT116 cells. There was a trend for even higher levels when proteins were coexpressed. (**p<0.01). (F) COX-2 protein increased in cells expressing RBM3 and HuR.

Figure 27:
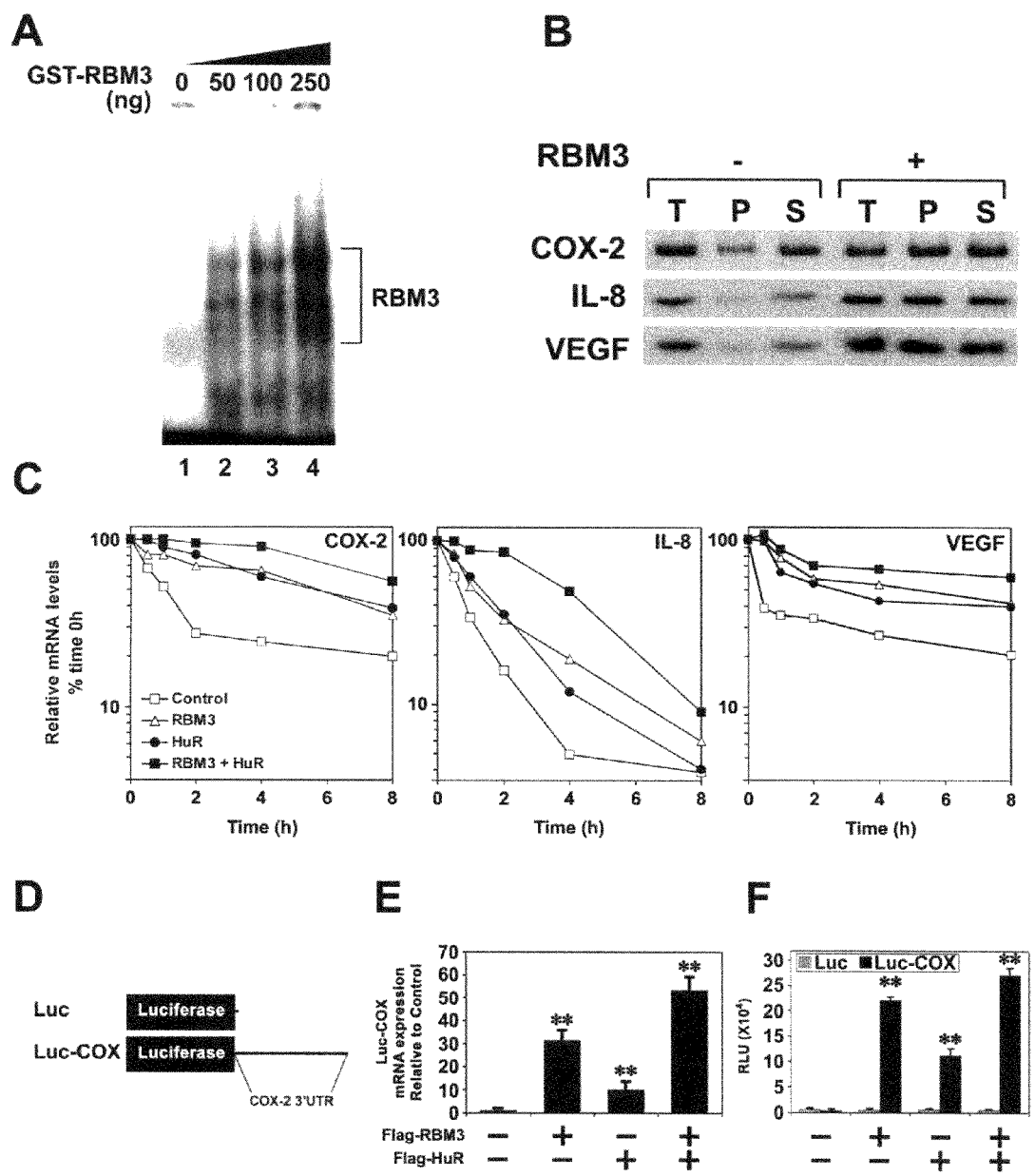

FIG. 27 demonstrates that RBM3 overexpression increases COX-2 mRNA stability and translation. (A) RBM3 is an ARE binding protein. The first sixty nucleotides of COX-2 3'UTR containing many ARE sequences was transcribed in vitro in the presence of $^{32}$P-UTP. Purified recombinant GST-RBM3 was allowed to interact with the radiolabeled RNA and subsequently separated in a native PAGE gel. Presence of the RBM3 bound RNA is shown by a mobility shift as indicated to the right. (B) Increased binding of COX-2, IL-8 and VEGF mRNA to RBM3 following overexpression. Whole cell extracts (T) from vector transfected or RBM3 overexpressing cells were prepared after crosslinking, and subjected to immunoprecipitation with anti-RBM3 antibody. RNA present in the immunoprecipitate (P) and supernatant (S) were isolated after reversing the crosslink and subjected to RT-PCR for COX-2, IL-8 and VEGF mRNA. Data demonstrates increased COX-2, Il-8 and VEGF mRNA in the pellet of RBM3 overexpressing cells. (C) RBM3 and HuR increase COX-2, IL-8 and VEGF mRNA stability. HCT116 cells were transfected with Flag epitope-tagged RBM3 and/or HuR and the stability of endogenous transcripts was determined following addition of actinomycin D. Both RBM3 and HuR increased COX-2 (left panel), IL-8 (middle panel) and VEGF (right panel) mRNA stability on their own, which was further increased when the two were coexpressed. (D) Schematic representation of control luciferase mRNA (Luc) and luciferase mRNA containing the full length COX-2 3'UTR (Luc-COX) that is encoded in the plasmid under the control of the CMV promoter. (E) RBM3 and HuR increases the translation of Luc mRNA containing COX-2 3'UTR. HCT116 cells transiently overexpressing RBM3, HuR or both were cotransfected with plasmids encoding either the Luc-COX or Luc control mRNA and luciferase activity was measured. Luciferase activity of Luc-COX is shown in black bars and that of Luc in grey bars. Asterisks denote statistically significant differences (p<0.01). (F) RBM3 and HuR increases the translation of Luc mRNA containing COX-2 3'UTR. HCT116 cells transiently overexpressing RBM3, HuR or both were cotransfected with plasmids encoding either the Luc-COX or Luc control mRNA and luciferase activity was measured. Luciferase activity of Luc-COX is shown in black bars and that of Luc in grey bars. Asterisks denote statistically significant differences (p<0.01).

Figure 28:
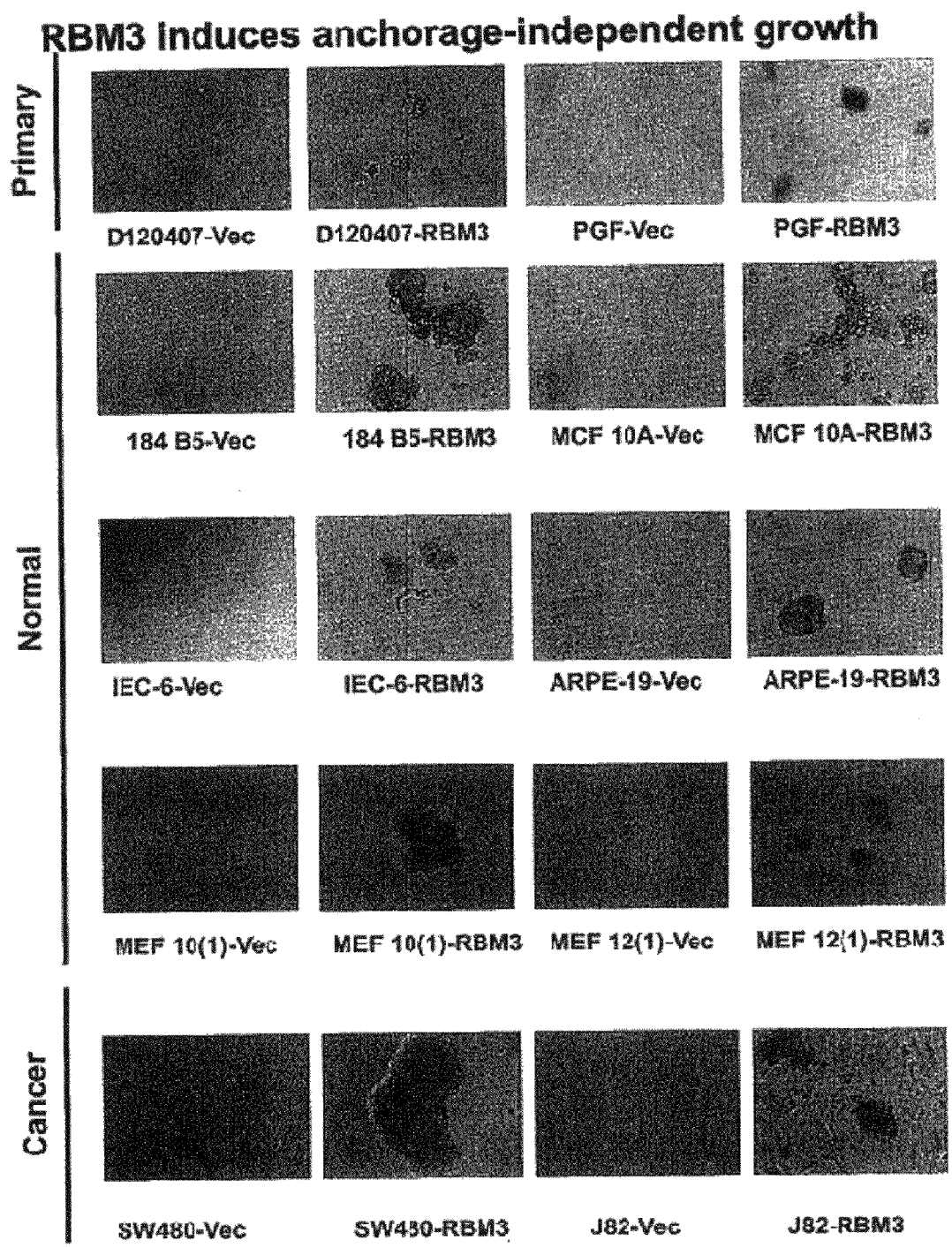

FIG. 28 demonstrates that RBM3 induces anchorage independent growth. RBM3 overexpression induces oncogenic transformation of primary [D120407 primary culture of human endometrial cells established by Dr. Doris M. Benbrook (OUHSC), PGF primary gingival fibroblast cells established by Dr. Barbara Mioczka (OUHSC)], and non-transformed cells [184B5 normal breast epithelial cells (ATCC), MCF 10A breast epithelial cells (Berkeley Lab, CA), IEC-6 normal rat intestinal epithelial cells (ATCC), ARPE-19 normal retinal pigmented epithelial cells (ATCC), MEF 12(1) mouse embryonic fibroblast wild type cells and MEF 10(1) mouse embryonic fibroblast p53 mutant cells established by Dr. Prabhat Goswami (University of IOWA)]. The SW480 colon cancer cell line (ATCC) and J82 bladder cancer cell line (ATCC) were used as positive controls. The cells transfected with plasmid vector (Vec) or stably expressing RBM3 were suspended in a 0.3% Sea Plaque agarose overlay in DMEM, 5% FBS. The overlay (1.0 ml), consisting of cells, agarose, and medium, was plated at 2000 cells/well in Nunc 10 cm plates over bottom layers of soft agarose (0.8%) containing only DMEM, 5% FBS. Plates were incubated at 37° C. for 7 d. Colonies were counted and photographed. RBM3 over expression in cancer cells increased the size number of colonies when compared to vector transfected cancer cells.

Figure 29:
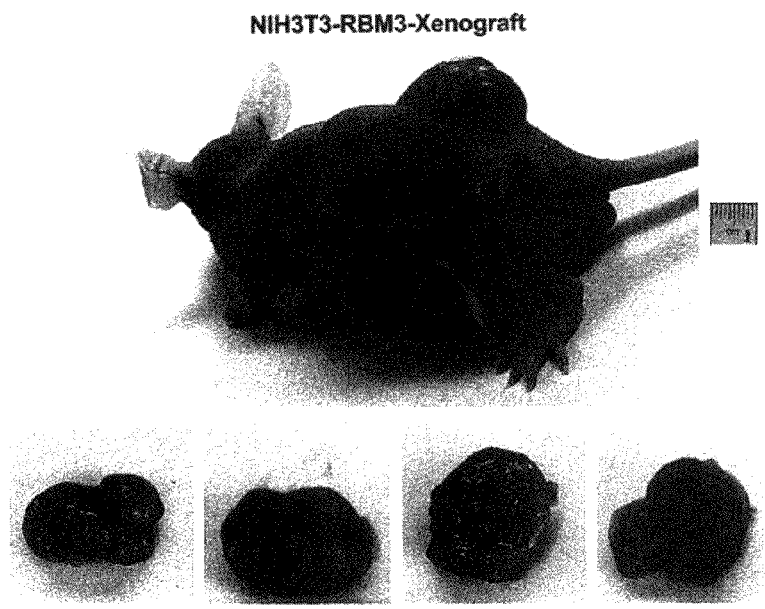

FIG. 29 demonstrates that NIH-3T3-RBM3 develops tumors in immuno-compromised mice. NIH-3T3-RBM3 overexpressing cells were injected subcutaneously into the flanks of female athymic nude mice and housed in specific pathogen-free conditions. Tumors were dissected after 21 d. Control NIH-3T3 did not develop tumors.

Figure 30:
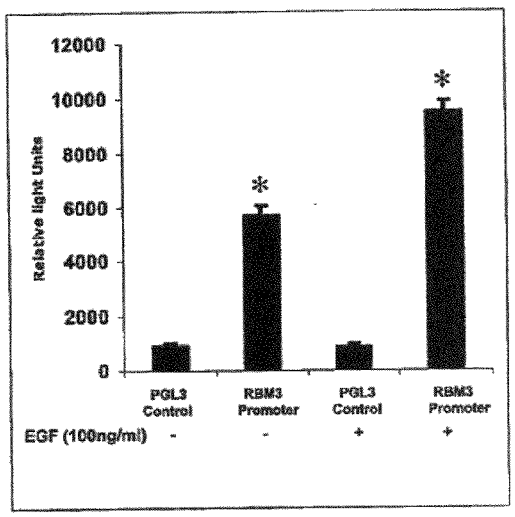

FIG. 30 illustrates RBM3 promoter activity. Transcription activity from the 2-kb region upstream of transcription start site. The 2000 bp PCR product was cloned into pGL3 Basic vector (Promega). This places the PCR product upstream of the luciferase gene for promoter activity analysis. To normalize for transfection efficiency, the cells were co-transfected with 100 ng of pRL-TK (Promega) plasmid along with the promoter construct. The total cell lysates was prepared from cells 24 h post transfection and firefly luciferase activity was assayed using the dual Luciferase Kit (Promega). Data shows that the region has promoter activity and is responsive to EGF. * denotes p<0.001.

Figure 31:
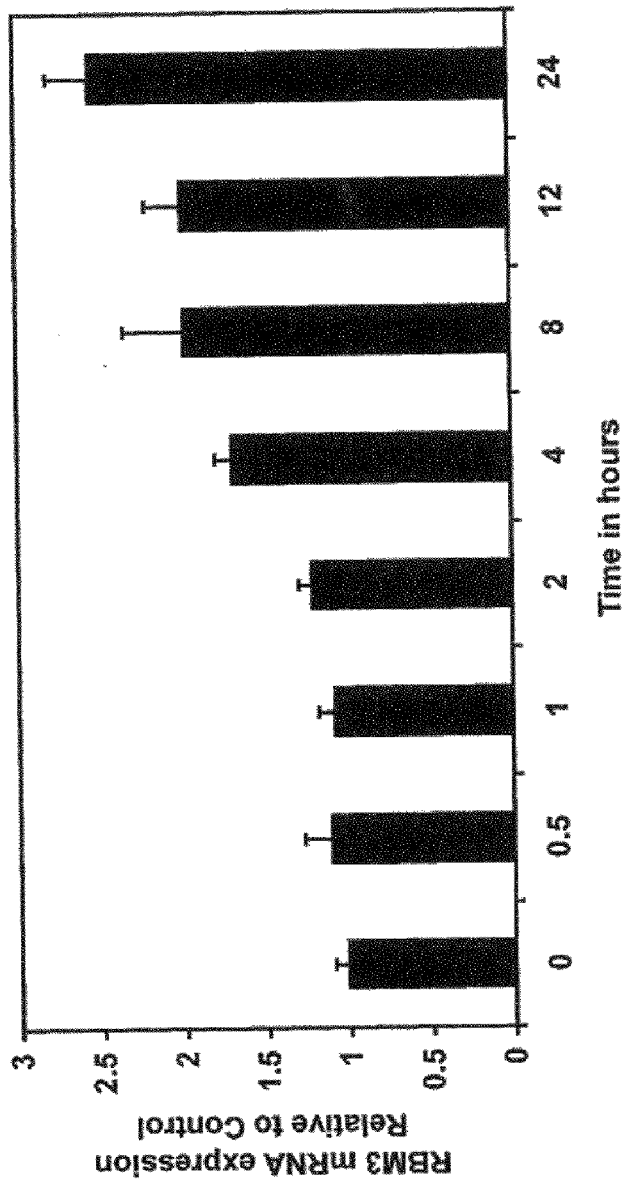

FIG. 31 illustrates that VEGF induces RBM3 expression. Human Umbilical Vein Endothelial cells following Vascular Endothelial Growth Factor (50 ng/ml) (Sigma) treatment and total RNA was isolated using Trizol reagent (Invitrogen) and RBM3 expression was determined. β-actin was used as internal control Data shows RBM3 mRNA levels were increased from 4 to 24 h following VEGF treatment.

Figure 32:
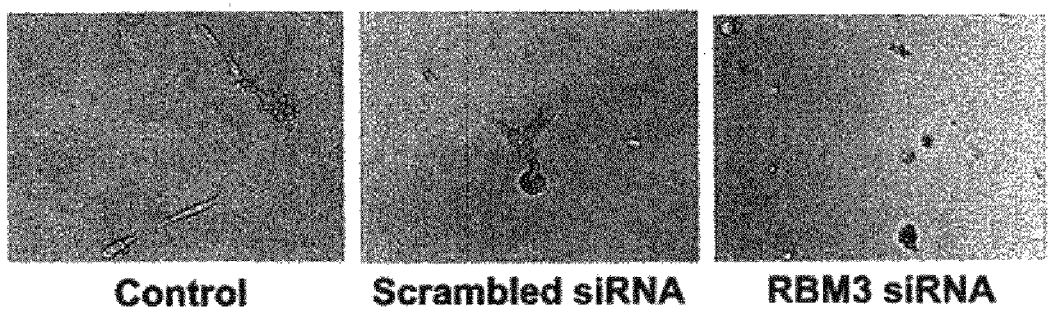

FIG. 32 illustrates that siRNA-mediated knockdown of RBM3 inhibits angiogenesis in vitro. HUVEC Cells ($1\times10^4$ cells per well) incubated 6-10 hours at 37° C. onto the surface of the polymerized ECMatrix™. Data demonstrates that siRNA-mediated knockdown of RBM3 inhibited the angiogenesis.

DETAILED DESCRIPTION OF THE INVENTION

Before explaining at least one embodiment of the invention in detail by way of exemplary drawings, experimentation, results, and laboratory procedures, it is to be understood that the invention is not limited in its application to the details of construction and the arrangement of the components set forth in the following description or illustrated in the drawings, experimentation and/or results. The invention is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

RNA interference (hereinafter "RNAi") is a method of post-transcriptional gene regulation that is conserved throughout many eukaryotic organisms. RNAi is induced by short (i.e., <30 nucleotide) double stranded RNA ("dsRNA") molecules which are present in the cell. These short dsRNA molecules, called "short interfering RNA" or "siRNA," cause the destruction of messenger RNAs ("mRNAs") which share sequence homology with the siRNA. It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

Specific methods of using siRNAs are described in detail in U.S. Pat. Nos. 7,345,027, issued to Tolentino et al. on Mar. 18, 2008; 7,148,342, issued to Tolentino et al. on Dec. 12, 2006; 7,511,025, issued to Wyatt et al. on Mar. 31, 2009; and 7,511,132, issued to Khvorova et al. on Mar. 31, 2009; the entire contents of such patents are expressly incorporated herein by reference. These patents describe siRNAs which specifically target and cause RNAi-induced degradation of mRNA, such as RNA from VEGF and VEGF receptors, MMP-1 and BCL-2, respectively, and such siRNA compounds may be used to suppress invasion and/or metastasis of tumor cells and/or inhibit angiogenesis, in particular for the treatment of cancerous tumors, age-related macular degeneration, and other angiogenic diseases. The methods of these patents may be applied to the production and use of siRNAs in accordance with the presently disclosed and claimed invention.

As used herein, the term "anticancer agent" refers to a molecule capable of inhibiting cancer cell function. The agent may inhibit proliferation or may be cytotoxic to cells. A variety of anticancer agents can be used and include those that inhibit protein synthesis and those that inhibit expression of certain genes essential for cellular growth or survival. Anticancer agents include those that result in cell death and those that inhibit cell growth, proliferation and/or differentiation. In one embodiment, the anticancer agent may be selectively toxic against certain types of cancer cells but does not affect or is less effective against other normal cells. In another embodiment, the anticancer agent is an antineoplastic agent.

The term "antineoplastic agent" is used herein to refer to agents that have the functional property of inhibiting a development or progression of a neoplasm in a human or animal, particularly a malignant (cancerous) lesion, such as a carcinoma, sarcoma, lymphoma, or leukemia. Inhibition of metastasis is frequently a property of antineoplastic agents.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the invention. The therapeutic effect may include, for example but not by way of limitation, inhibiting the growth of undesired tissue or malignant cells. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy", and will be understood to mean that the patient in need of treatment is treated or given another drug for the disease in conjunction with the pharmaceutical compositions of the presently disclosed and claimed invention. This concurrent therapy can be sequential therapy where the patient is treated first with one drug and then the other, or the two drugs are given simultaneously.

The terms "administration" and "administering", as used herein will be understood to include all routes of administration known in the art, including but not limited to, oral, topical, transdermal, parenteral, subcutaneous, intranasal, mucosal, intramuscular and intravenous routes, including both local and systemic applications. In addition, the methods of administration may be designed to provide delayed or controlled release using formulation techniques which are well known in the art.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism. A molecule can be biologically active through its own functionalities, or may be biologically active based on its ability to activate or inhibit molecules having their own biological activity.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

A "liposome" is a small vesicle composed of various types of lipids, phospholipids and/or surfactant. The components of the liposome are commonly arranged in a bilayer formation, similar to the lipid arrangement of biological membranes.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

The term "patient" as used herein includes human and veterinary subjects. "Mammal" for purposes of treatment refers to any animal classified as a mammal, including human, domestic and farm animals, nonhuman primates, and any other animal that has mammary tissue.

The terms "treat", "treating" and "treatment", as used herein, will be understood to include both inhibition of tumor growth as well as induction of tumor cell death.

As used herein, the term treating cancer or treatment of cancer means to inhibit the spread of cancer, decrease tumor size, lessen or reduce the number of cancerous cells in the body, or ameliorate or alleviate the symptoms associated with the cancer. The treatment is considered therapeutic if there is a decrease in mortality and/or morbidity, or a decrease in disease burden manifested by reduced numbers of malignant cells in the body.

Preventing cancer or prevention of cancer is intended to mean preventing the occurrence or recurrence of the disease state of cancer. As such, a treatment that impedes, inhibits, or interferes with metastasis, tumor growth, or cancer proliferation is deemed preventive.

As used herein, managing cancer encompasses preventing the recurrence of cancer in a patient who had suffered from cancer, lengthening the time a patient remains in remission, preventing the occurrence of cancer in patients at risk of suffering from cancer (e.g., patients who had been exposed to high amounts of radiation or carcinogenic materials; patients infected with viruses associated with the occurrence of cancer; and patients with genetic predispositions to cancer), and preventing the occurrence of malignant cancer in patients suffering from pre-malignant or non-malignant cancers.

Administering a therapeutically effective amount or prophylactically effective amount is intended to provide a therapeutic benefit in the treatment, prevention, or management of cancer. The specific amount that is therapeutically effective can be readily determined by the ordinary medical practitioner, and can vary depending on factors known in the art, such as the type of cancer, the patient's history and age, the stage of cancer, the co-administration of other anti-cancer agents, including radiation therapy.

The presently disclosed and claimed invention is related to methods of inhibiting tumor growth. Such methods involve an inhibition of one or more RNA binding proteins in the tumor cells. In one embodiment, the RNA binding protein is Musashi-1 (Msi-1); in another embodiment, the RNA binding protein is RNA binding motif protein 3 (RBM3). Such methods of inhibition of RNA binding proteins result in a decrease in cancer cell proliferation and apoptosis, as well as $G_2/M$ arrest, coupled with mitotic catastrophe. Inhibition of RNA binding protein(s) may also result in a decrease in mRNA stability and/or translation for the gene products of at least one of vascular endothelial growth factor (VEGF), interleukin-8 (IL-8), cyclooxygenase-2 (COX-2), Notch-1 and matrix metalloproteinase 7 (MMP7).

The expression of said RNA binding protein(s) can be inhibited using any well known method that targets the RNA binding protein's gene or its mRNA. These methods include, but are not limited to, the use of antisense oligonucleotides, ribozymes, nucleic acid molecules that promote triple helix formation, and short-interfering RNAs (siRNAs) or co-repression of a target gene by introducing a homologous gene fragment into the cell that harbors the target gene. In particular embodiments, the methods of the presently disclosed and claimed invention employ siRNAs that specifically reduces expression of the RNA binding protein.

In one embodiment, the expression of at least one RNA binding protein is inhibited by the use of an RNA interference technique referred to as RNAi. RNAi allows for the selective knockout of a target gene in a highly effective and specific manner. This technique involves introducing into a cell double-stranded RNA (dsRNA), having a sequence corresponding to the exon portion of the target gene. The dsRNA causes a rapid destruction of the target gene's mRNA.

RNAi can be performed, for example, using chemically-synthesized RNA. Alternatively, suitable expression vectors can be used to transcribe such RNA either in vitro or in vivo. In vitro transcription of sense and antisense strands (encoded by sequences present on the same vector or on separate vectors) can be effected using for example T7 RNA polymerase, in which case the vector can contain a suitable coding sequence operably-linked to a T7 promoter. The in vitro-transcribed RNA can, in certain embodiments, be processed (e.g., using *E. coli* RNase III) in vitro to a size conducive to RNAi. The sense and antisense transcripts are combined to form an RNA duplex which is introduced into a target cell of interest. Other vectors can be used, which express small hairpin RNAs (shRNAs) which can be processed into siRNA-like molecules. Various vector-based methods are described in, for example, Brummelkamp, et al. (2002) Science 296(5567): 550-3; Lee, et al. (2002) Nat. Biotechnol. 20(5):500-5; Miyagashi and Taira (2002) Nat. Biotechnol. 20(5):497-500; Paddison, et al. (2002) Proc. Natl. Acad. Sci. USA 99(3):1443-8; Paul, et al. (2002); and Sui, et al. (2002) Proc. Natl. Acad. Sci. USA 99 (8):5515-20. Various methods for introducing such vectors into cells, either in vitro or in vivo (e.g., gene therapy), are known in the art.

Kits for production of dsRNA for use in RNAi are available commercially, e.g., from New England Biolabs, Inc. and Ambion Inc. (Austin, Tex., USA). Methods of transfection of dsRNA or plasmids engineered to make dsRNA are routine in the art.

The methods described herein may be utilized for treatment of any cancer, including but not limited to, cancers of the colon, pancreas, breast, prostate, lung and ovaries. Particular cancers that can be treated and managed by the methods of the presently disclosed and claimed invention include, but are not limited to, those associated with an increase in the expression of at least one RNA binding protein, including but not limited to, Musashi-1 (Msi-1) and RNA binding motif protein 3 (RBM3).

In one embodiment, the presently disclosed and claimed invention is directed to a short-interfering ribonucleic acid (siRNA) molecule effective at silencing Musashi-1 (Msi-1) expression. The siRNA molecule comprises a sense RNA strand and an antisense RNA strand, wherein the sense and antisense RNA strands form an RNA duplex, and wherein the sense RNA strand comprises a nucleotide sequence identical to a target sequence of about 15 to about 25 contiguous nucleotides in Msi-1 mRNA (or a homolog thereof). The Msi-1 target sequence that binds the siRNA can be selected experimentally or empirically. In certain embodiments, the Msi-1 mRNA may be in accordance with SEQ ID NO:1, and the sense RNA strand may comprise at least one of SEQ ID NOS:2 and 3.

Alternatively, depending on the conditions under which binding is sufficient to disrupt the function of the Msi-1 gene, a sequence complementary to a target sequence within the Msi-1 nucleic acid sequences need not be 100 percent identical to the target sequence. For example, a sequence can be complementary to its target sequence when at least about 80 or 90 percent of its nucleotides bind via matched base pairings with nucleotides of the target sequence.

Therefore, the sense RNA strand may comprise a sequence homologous to a portion of SEQ ID NO:1 that is capable of hybridizing to its target sequence under stringent conditions. In general, for complementary sequences to hybridize under stringent conditions, said sequences are at least 80 or 90 percent identical to each other. One non-limiting example of stringent hybridization conditions includes 6× sodium chloride/sodium citrate (SSC) at about 45° C., followed by 0.2× SSC, 0.1% SDS at 50-65° C. Thus, the presently disclosed and claimed invention also includes siRNAs having a sense RNA strand that comprises a nucleotide sequence that is at least 90% identical to a target sequence of about 15 to about 25 contiguous nucleotides in Msi-1 mRNA (or a homolog thereof).

In another embodiment, the presently disclosed and claimed invention is directed to a short-interfering ribonucleic acid (siRNA) molecule effective at silencing RNA binding motif protein 3 (RBM3) expression. The siRNA molecule comprises a sense RNA strand and an antisense RNA strand, wherein the sense and antisense RNA strands form an RNA duplex, and wherein the sense RNA strand comprises a nucleotide sequence identical to a target sequence of about 15 to about 25 contiguous nucleotides in RBM3 mRNA (or a homolog thereof). The RBM3 target sequence that binds the siRNA can be selected experimentally or empirically. In certain embodiments, the RBM3 mRNA may be in accordance with SEQ ID NO:10, and the sense RNA strand may comprise SEQ ID NO:11.

Alternatively, depending on the conditions under which binding is sufficient to disrupt the function of the RBM3 gene, a sequence complementary to a target sequence within the RBM3 nucleic acid sequences need not be 100 percent identical to the target sequence. For example, a sequence can be complementary to its target sequence when at least about 80 or 90 percent of its nucleotides bind via matched base pairings with nucleotides of the target sequence.

Therefore, the sense RNA strand may comprise a sequence homologous to a portion of SEQ ID NO:10 that is capable of hybridizing to its target sequence under stringent conditions. In general, for complementary sequences to hybridize under stringent conditions, said sequences are at least 80 or 90 percent identical to each other. One non-limiting example of stringent hybridization conditions includes 6× sodium chloride/sodium citrate (SSC) at about 45° C., followed by 0.2× SSC, 0.1% SDS at 50-65° C. Thus, the presently disclosed and claimed invention also includes siRNAs having a sense RNA strand that comprises a nucleotide sequence that is at least 90% identical to a target sequence of about 15 to about 25 contiguous nucleotides in RBM3 mRNA (or a homolog thereof).

The siRNAs of the presently disclosed and claimed invention may include modifications to their sugar-phosphate backbone or nucleosides. These modifications can be tailored to promote selective genetic inhibition, while avoiding a general panic response reported to be generated by siRNA in some cells. Moreover, modifications can be introduced in the bases to protect siRNAs from the actin of one or more endogenous degradative enzymes.

The presently disclosed and claimed invention also includes a pharmaceutical composition comprising any of the siRNA molecules described herein above. The pharmaceutical composition may further comprise at least one additional chemotherapeutic agent, as described in detail herein. In addition, the pharmaceutical composition may also further comprise a delivery agent, such as but not limited to, a liposome.

Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to, tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the agents of the invention from degradation within the gastrointestinal tract. In another example, the agents of the invention may be administered in a liposomal formulation to shield the agents from degradative enzymes, facilitate transport in circulatory system, and effect delivery across cell membranes to intracellular sites.

The composition, shape, and type of dosage forms of the pharmaceutical compositions of the presently disclosed and claimed invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by the invention will vary from one another and will be readily apparent to those skilled in the art. See, e.g., Remington: The Science and Practice of Pharmacy, Alfonso R. Gennaro, editor, 20th ed. Lippincott Williams & Wilkins: Philadelphia, Pa., 2000.

In one embodiment, the presently disclosed and claimed invention also includes a method of inhibiting expression of Musashi-1 (Msi-1) protein. Said method includes providing a cell expressing Msi-1 and providing the siRNA molecule described herein above; the cell is then contacting with the siRNA, thereby specifically inhibiting the expression of Msi-1.

The presently disclosed and claimed invention also includes a method of inhibiting expression of Musashi-1 (Msi-1) protein in a subject. In said method an effective amount of the pharmaceutical composition described herein above is administered to the subject, thereby specifically inhibiting the expression of Msi-1.

In one embodiment, the presently disclosed and claimed invention also includes a method of inhibiting expression of RNA binding motif protein 3 (RBM3). Said method includes providing a cell expressing RBM3 and providing the siRNA molecule described herein above; the cell is then contacting with the siRNA, thereby specifically inhibiting the expression of RBM3.

The presently disclosed and claimed invention also includes a method of inhibiting expression of RNA binding motif protein 3 (RBM3) in a subject. In said method an effective amount of the pharmaceutical composition described herein above is administered to the subject, thereby specifically inhibiting the expression of RBM3.

The presently disclosed and claimed invention further includes a method of inhibiting tumor growth. In said method, at least one of the siRNAs described herein above is provided and contacted with the tumor, thereby specifically inhibiting the expression of at least one RNA binding protein (such as but not limited to, Msi-1 and RBM3) in the tumor and thus inhibiting growth of the tumor. Said method may result in at least one of a decrease in cancer cell proliferation, apoptosis, $G_2$/M arrest, mitotic catastrophe and a decrease in at least one of mRNA stability and mRNA translation for at least one protein selected from the group consisting of vascular endothelial growth factor (VEGF), interleukin-8 (IL-8), cyclooxygenase-2 (COX-2), matrix metalloproteinase 7 (MMP7), Notch-1 and combinations thereof.

The presently disclosed and claimed invention also includes a method of inhibiting tumor growth in a subject, which includes providing at least one of the pharmaceutical compositions described herein above and administering an effective amount thereof to the subject, thereby specifically inhibiting the expression of at least one RNA binding protein (such as but not limited to, Msi-1 and RBM3) in the tumor and thus inhibiting growth of the tumor. Said method may result in at least one of a decrease in cancer cell proliferation, apoptosis, $G_2$/M arrest, mitotic catastrophe and a decrease in at least one of mRNA stability and mRNA translation for at least one protein selected from the group consisting of vascular endothelial growth factor (VEGF), interleukin-8 (IL-8), cyclooxygenase-2 (COX-2), matrix metalloproteinase 7 (MMP7), Notch-1 and combinations thereof.

Delivery of the agents of the presently disclosed and claimed invention (e.g., siRNAs) into a patient can either be direct, i.e., the patient is directly exposed to an agent of the invention or agent-carrying vector, or indirect, i.e., cells are first transformed with the nucleic acid sequences encoding an agent of the invention in vitro, then transplanted into the patient for cell replacement therapy. These two approaches are known as in vivo and ex vivo therapy, respectively.

The presently disclosed and claimed invention is also directed to a method of generating a tumor cell. Such method includes providing at least one of a primary cell and an immortalized cell, and introducing a gene encoding at least one RNA binding protein (such as, but not limited to, Msi-1 and RBM3) into the cell such that the cell overexpresses the at least one RNA binding protein and exhibits increased cell proliferation and induction of anchorage independent growth. Such generated tumor cell may then be utilized as a model system for identifying novel therapeutics for cancer therapy.

The presently disclosed and claimed invention is also directed to a diagnostic method for cancer detection, progression and/or prognosis. Such diagnostic method involves the detection of at least one RNA binding protein, such as but not limited to, Msi-1 and RBM3, as a marker. The method may also include detection of the specific level of RNA binding protein present and comparison thereof to known levels of RNA binding protein present in normal cells and in cells at various stages of tumor progression and/or metastasis.

Examples are provided hereinbelow. However, the presently disclosed and claimed invention is to be understood to not be limited in its application to the specific experimentation, results and laboratory procedures. Rather, the Examples are simply provided as one of various embodiments and are meant to be exemplary, not exhaustive.

Example 1

The present Example demonstrates that Msi-1 expression is upregulated in human colorectal tumors compared with its paired uninvolved tissue. siRNA-mediated knockdown of Msi-1 in the tumor xenografts resulted in the arrest of tumor growth. Furthermore, inhibition of Msi-1 resulted in decreased cancer cell proliferation, increased caspase-3-mediated apoptosis alone, and enhanced radiation-induced apoptosis. However, there was increased staining for phosphorylated histone H3 (a marker of mitosis) and colocalization of terminal deoxynucleotidyl transferase-mediated deoxyuridine triphosphate nick-end labeling (TUNEL) staining in phosphorylated histone H3 immunoreactive cells, particularly in the tumor xenografts, suggestive of mitotic catastrophe. Furthermore, siRNA mediated down-regulation of Msi-1 resulted in a shift towards the $G_2/M$ phase of the cell cycle. Furthermore, there was down-regulation of Notch-1 and activated Notch-1, and up-regulation of $p21^{WAF1}$ after downregulation of Msi-1. These results support a novel role for Msi-1 in intestinal tumorigenesis as a cell proliferation regulator and inhibitor of mitotic catastrophe.

Materials and Methods for Example 1

Cell culture: HCT116 and HT29 human colon adenocarcinoma cell lines were obtained from the American type culture collection (ATCC) and grown in Dulbecco's modified eagle's medium (DMEM) supplemented with 10% fetal bovine serum and 100-U/mL penicillin-streptomycin in a humidified chamber at 37° C. with 5% $CO_2$.

Silencer RNA: Msi-1 siRNA (si-Msi-1) sequence targeting the coding region of Msi-1 (Accession # NM_002442; SEQ ID NO:1) was (#1-CUUUUGGAUUUGUGCAU (SEQ ID NO:2) and #2-ACAUCGUGGAGAAAGUG (SEQ ID NO:3)) and scrambled control siRNAs (si-scrambled) not matching any of the human genes was obtained (Ambion Inc., Austin, Tex.) and transfected using Transfectol™ (Ambion Inc.).

Human colorectal carcinoma specimens: Total RNA isolated from human colorectal specimens and its paired uninvolved tissues were provided by Dr. Howard L. McLeod at the University of North Carolina, which was obtained from Tissue Procurement Core of the Siteman Cancer Center, Washington University.

Real Time PCR Analyses: Total RNA isolated either from cells or human colon cancer tumors and its paired uninvolved tissues or from human colon cancer cell tumor xenograft samples were subjected to reverse transcription with Superscript™ II RNase H—Reverse Transcriptase and random hexanucleotide primers (Invitrogen, Carlsbad, Calif.). The cDNA was subsequently used to perform Real Time PCR by SYBR chemistry (SYBR® Green I; Molecular Probes) for specific transcripts using gene specific primers and Jumpstart Taq DNA polymerase (Sigma-Aldrich, St. Louis, Mo.). The crossing threshold value assessed by Real Time PCR was noted for the transcripts and normalized with β-actin mRNA. The changes in mRNA expression were expressed as fold change relative to control with ±SEM value.

Primers Used are:

```
β-actin: Forward: 5'-GGTGATCCACATCTGCTGGAA-3',   (SEQ ID NO: 4)
         Reverse: 5'-ATCATTGCTCCTCCTCAGGG-3',    (SEQ ID NO: 5)

Msi-1:   Forward: 5'-CAGTTTCGGACCTATCTCTGAGGT-3', (SEQ ID NO: 6)
         Reverse: 5'-AAGGTGATGAAACCAAAACCCCT-3',  (SEQ ID NO: 7)

Msi-2:   Forward: 5'-TGAGCTGGCAGACCTCACCA-3',    (SEQ ID NO: 8)
         Reverse: 5'-AAACCGAAGCCTCTGGAGCG-3'.    (SEQ ID NO: 9)
```

Western Blot analysis: HCT116 cells were cultured in a 6 well plates to 40% confluency and were transfected with si-Msi-1 or si-scrambled for 72 h. Cells or the tumor xenograft samples were lysed and concentration of protein was determined by BCA protein assay kit (Pierce Biotechnology Inc., Rockford, Ill.). Forty μg of the protein was size separated in a 15% SDS polyacrylamide gel and transferred on to a nitrocellulose membrane with a semidry transfer apparatus (Amersham-Pharmacia, Piscataway, N.J.). The membrane was blocked in 5% non-fat dry milk for 1 h and probed overnight with a rabbit anti-Msi-1 antipeptide antibody (Abcam Inc., Cambridge, Mass.) or with goat anti-Notch-1 antibody (Santa Cruz Biotechnology Inc., Santa Cruz, Calif.) or with rabbit anti-p21 antibody (Santa Cruz Biotechnology Inc.). Subsequently the membrane was incubated with anti-rabbit IgG or with anti-goat IgG horseradish peroxidase-conjugated (Amersham-Pharmacia) for 1 h at room temperature. The 39 kDa Msi-1 protein, 21 kDa $p21^{WAF1}$, 300 kDa Notch-1 and 120 kDa cleaved Notch-1 were detected using ECL™ Western Blotting detection reagents (Amersham-Pharmacia). Actin (43 kDa), used as loading control was identified using a goat polyclonal IgG (Santa Cruz Biotechnology Inc., Santa Cruz, Calif.).

Immunohistochemistry: (a) Brightfield: Heat Induced Epitope Retrieval (HIER) was performed on 4 μm paraffin-embedded tumor xenograft sections utilizing a pressurized de-cloaking chamber (Biocare Medical, LLC, Concord, Calif.) and incubated in citrate buffer (pH 6.0) at 99° C. for 18 min. The sections were then washed three times with PBS (Sigma), and endogenous biotin activity was blocked using Avidin/Biotin blocking kit (Vector Lab, Burlingame, Calif.) according to manufacturer's instructions. Further, endogenous peroxidase activity was quenched with 3% hydrogen peroxide. After washing, the slides were then incubated in horse normal serum (2%) and BSA (1%) at room temperature for 20 min to block non-specific binding. The sections were then exposed to primary antibodies [(rabbit anti-Msi-1 (Abcam), rabbit anti-caspase-3 (Cell Signaling, Danvers, Mass.), rabbit anti-phosphorylated histone H3 (Thr-11) (Upstate, Lake Placid, N.Y.), goat anti-Notch-1 (Santa Cruz Biotechnologies) or rabbit antip2$^{WAF1}$ (Santa Cruz Biotechnologies)] overnight at 4° C. Slides were then washed three times with PBS and incubated in the appropriate secondary antibody biotinylated donkey anti-rabbit, donkey anti-goat (Jackson Immuno Research Lab, West Grove, Pa.) for 30 min at room temperature. Slides were washed again and then incubated in Streptavidin-HRP (Dako, Carpinteria, Calif.) at room temperature for 12 min. After final wash in PBS, chromogenic development was performed utilizing DAB substrate (Sigma). TUNEL staining was performed using In situ Cell Death Kit (Roche diagnostics, Indianapolis, Ind.) according to the manufacturer's instructions, and the POD converter was utilized to enable DAB chromogenic development. All slides were counterstained with hematoxylin (Biocare Medical), dehydrated in graded alcohols, cleared in xylene, and permanently mounted with cryoseal (Richard-Allen, Kalamazoo, Mich.). (b) Fluorescence: HIER was performed on 4 μm paraffin-embedded tumor xenograft sections utilizing a pressurized de-cloaking chamber (Biocare Medical, LLC) and incubated in citrate buffer (pH 6.0) at 99° C. for 18 min. After washing three times with PBS, the slides were then incubated in horse normal serum (2%) and BSA (1%) at room temperature for 20 min to block non-specific binding. Sections were then sequentially exposed to rabbit phosphorylated histone H3 (Upstate) or rabbit Musashi-1 (Abcam) for 1 h at 30° C. and its appropriate secondary fluorescent conjugate alexa fluor 488 (green) or alexa fluor 568 (red) (Invitrogen) for 30 min at room temperature wherever indicated. Finally fluorescein conjugated Terminal deoxynucleotidyl Transferase Biotin-dUTP Nick End Labeling (TUNEL) staining was performed using "In situ Cell Death Kit" (Roche diagnostics), according to manufacturer's instructions. The slides were then wet-mounted and counterstained utilizing Vectashield with DAPI (Vector Lab) or with Hoechst 33342 (Invitrogen). (c) Microscopic Examination: Slides were examined using Nikon 80i microscope base. For brightfield, 60× digital images were taken with PlanAPO objective and DXM1200C camera (Nikon, Melville, N.Y.). Fluorescent images were taken with 60× PlanFluoro objective and 2× optical converter for a final magnification of 120×, utilizing CoolSnap ES2 camera (Photometrics, Tucson, Ariz.). Filter sets with excitation ranges for Cy3, FITC, and DAPI were used. All images were captured utilizing NIS-Elements software (Nikon) and further processed using Adobe Photoshop 8.0 software (Adobe Systems Inc., San Jose, Calif.).

Cell Proliferation Assays.

Hexosaminidase assay: Msi-1-targeted siRNA was transfected with 1×10⁴ HCT116 or HT29 cells and plated simultaneously in a 96 well plates. Cell numbers were estimated at time point 24, 48 and 72 h after 48 h of siRNA transfection using a chromogenic substrate (p-nitrophenyl-N-acetyl-β-D-Glucosaminide) (Sigma-Aldrich). The lysozyme enzyme (N-acetyl-β-D-hexosaminidase) released from the proliferating cells convert the substrate to p-nitrophenyl, which was measured in a microtitre plate reader (Synergy HT, BIOTEK, Winooski, Vt.) at 405 nm (Landegren et al., 1984). The cell numbers were plotted as mean±SEM of 3 different experiments. The Students t test was used to calculate the statistical significance.

MTT assay: Msi-1-targeted siRNA was transfected with 1×10⁴ HCT116 cells and plated simultaneously in 96 well plates. Cell numbers were estimated at time point 72 h after 48 h of siRNA transfection using 50 μg of 3-[4,5-dimethylthiazol-2-yl]-2,5-diphenol tetrazolium bromide (MTT) assay. 10 μl of MTT (5 mg/ml) (Invitrogen) was added to each well, and the plates were incubated at 37° C. for 2 h. Then, 100 μL of solubilization solution (20% SDS, 50% dimethyl formamide, 2% acetic acid and 0.1N HCl in anhydrous isopropanol) was added, and the solution was pipetted up and down to dissolve the crystals. Absorbance was measured spectrophotometrically at a dual wavelength of 570 and 405 nm (Mosmann et al., 1983; and Agarwal et al., 1999).

Flow Cytometric analysis. HCT116 cells were transfected with 30 nM si-Msi-1 or si-scrambled for 72 h. The control and transfected cells were washed twice with ice-cold phosphate buffered saline (PBS) and harvested by trypsinization and further washed 6 times with PBS. The single-cell suspensions were fixed using 70% ethanol for 2 h. The cells were centrifuged to remove the 70% ethanol and washed with PBS. The ethanol fixed cells was permeabilized with PBS containing 1 mg/ml propidium iodide (Sigma-Aldrich), 0.1% triton X-100 (Sigma-Aldrich) and 2 mg DNase-free RNase (Sigma-Aldrich) at room temperature. Flow cytometry was done with a FACSCalibur analyzer 3-color (Becton Dickinson, Mountain, View, Calif.), capturing 50,000 events for each sample; results were analyzed with ModFit LT™ software (Verity Software House, Topsham, Me.).

Xenograft tumor model. (a) Liposomal preparation: siRNA was administered into the xenografts after incorporation into 1,2-Dioleoyl-sn-Glycero-3-Phosphocholine (DOPC) (Avanti Polar Lipids, Alabaster, Ala.). DOPC and siRNA were mixed in the presence of excess tertiary butanol at a ratio of 1:10 (w/w) (siRNA/DOPC). TWEEN® 20 (Sigma-Aldrich) was added to the mixture in a ratio of 1:19 TWEEN® 20: siRNA/DOPC. The mixture was vortexed and frozen in an acetone/dry ice bath and lyophilized. Before administration, the siRNA preparation was reconstituted in 0.9% sterile saline and injected at a dose of 50 μl (5 μM) per injection. (b) Tumor therapy: Female athymic nude mice (NCr-nu) were purchased from the National Cancer Institute-Frederick Cancer Research and Development Center (Frederick, Md.) and housed in specific pathogen-free conditions. They were cared for in accordance with guidelines set forth by the American Association for Accreditation of Laboratory Animal Care and the USPHS "Policy on Human Care and Use of Laboratory Animals," and all studies were approved and supervised by the Institutional Animal Care and Use Committee. HCT116 cells (6×10⁶) cells were injected subcutaneously into the flanks of 4-6 week-old female athymic nude mice (5 mice per group). Tumors were measured with calipers and calculated volume as (length×width²)×0.5. The tumors reached 500 mm³ after 15 days of injection of cells. These tumors were injected with 50 μl (5 μM) of siRNA preparation on every third day from day 15 for a total of 5 doses.

Results for Example 1

Msi-1 is expressed in human colorectal tumor and knockdown inhibits growth of tumor xenografts. Msi-1 is overexpressed in $APC^{min/+}$ mice tumors compared to uninvolved tissue (Potten et al., 2003). To determine the expression of Msi-1 in human colorectal tumors, total RNA was isolated from resection specimens of patients with colonic or rectal adenocarcinoma. The RNA from the tumors and the paired surrounding uninvolved tissue were subjected to real-time RT PCR for Msi-1. A greater than 2 fold increase ($p<0.01$) of Msi-1 mRNA expression was found in 10 out of 15 tumor specimens, compared to its paired uninvolved tissues (FIG. 1A). In order to determine the role of Msi-1 in tumor progression, tumor xenografts were generated by injecting HCT116 cells subcutaneously into athymic nude mice and injected those tumors with siRNA targeted against human Msi-1 (si-Msi-1), scrambled siRNA (si-scrambled) or transfection reagent/carrier alone (Control). The tumor volume was calculated at various time points. Administration of si-Msi-1 arrested HCT116 colon adenocarcinoma tumor xenograft growth. Moreover, si-Msi-1 treated tumors (average tumor volume of 899.2±517.4 mm³) were considerably smaller than the control (4124.3±1301.1 mm³) or the si-scrambled treated tumors (6225.7±638.18 mm³). The inhibition produced by si-Msi-1 was statistically significant ($p<0.05$) compared to control or ($p<0.01$) compared to si-scrambled treated tumors (FIG. 1B). Total RNA isolated from these tumors was subjected to real-time RT PCR and demonstrated a significant (60%) downregulation of Msi-1 mRNA expression in the si-Msi-1 treated tumors compared to control or si-scrambled treated tumors (FIG. 1C). Similarly, reduced expression of Msi-1 protein was found in those tumors as demonstrated by the western blot analyses (FIG. 1D) and by immunohistochemistry (FIG. 1E).

Downregulation of Msi-1 results in reduced cancer cell proliferation. Given the reduction in tumor size following knockdown of Msi-1, the possibility that downregulation of Msi-1 affects cancer cell proliferation was tested next. To demonstrate knockdown of Msi-1 in the cells following transfection with 2 different siRNAs, si-Msi-1 (si-Msi-1 #1—used in tumor xenograft study) and si-Msi-1 #2 and si-scrambled, total RNA isolated from these cells was subjected to real-time RT PCR. A significant down regulation of Msi-1 mRNA was noted at 10 and 50 nM of both si-Msi-1 #1 and #2. At 50 nM, there was more than 60% reduction in expression (FIG. 2A). si-Msi-1 #1 and si-Msi-1 #2 demonstrated a dose dependent decrease in Msi-1 protein as demonstrated by Western blot analyses (FIG. 2B). Scrambled siRNA did not inhibit Msi-1 mRNA or protein expression. Subsequently, the impact of siRNA transfection on cell proliferation in HCT116 and HT29 colon cancer cells was investigated. It was noted that proliferation of the HCT116 cells was significantly inhibited when Msi-1-targeted siRNAs was transfected into cells (FIG. 2C). A significant ($p<0.01$) reduction in HCT116 cell proliferation was observed when two different si-Msi-1 were used at a concentration of 30 nM. The total numbers of cells in the si-Msi-1 transfected cells were 780×10³ cells (si-Msi-1 #1) and 760×10³ cells (si-Msi-1 #2) compared to control (transfection treatment alone) (980×10³) and si-scrambled treated tumors (1068×10³ cells). A subtle increase in proliferation was observed when the cells were transfected with si-scrambled. A significant ($p<0.01$) reduction (30%) in HT29 colon cancer cell proliferation was also observed following 30 nM siRNA mediated knockdown of Msi-1 (FIG. 2D). One of the tools for validation of siRNA is to adopt 2 or more siRNAs to demonstrate similar activity. Here a total of 3 different si-scrambled (Ambion Inc.,) and were utilized to transfect HCT116 cells using TRANSFECTOL™ reagent (Ambion Inc.), and proliferation was assessed by hexosaminidase and MTT assays. Similar results were found with both proliferation assays. All the three scrambled siRNAs increased HCT116 cancer cell proliferation by 30%, estimated by both hexosaminidase and MTT assays. There was an increase in proliferation (50%) by the scrambled siRNA in the DOPC transfection reagent used for injecting into tumor xenografts. DOPC transfection reagent alone did not alter the proliferation of HCT116 cells. si-Msi-1 transfected using Transfectol™ or DOPC transfection reagent demonstrated a down regulation of HCT116 cancer cell proliferation (FIG. 3A—Hexosaminidase assay; FIG. 3B—MTT assay).

Knockdown of Msi-1 induces apoptosis, mitosis and G2/M arrest in cancer cells. Additionally, the role of Msi-1 in apoptosis and mitosis was investigated. HCT116 cells transfected with si-Msi-1 and si-scrambled, were fixed and immunostained for activated caspase-3, for measuring apoptosis and phosphorylated histone H3 (Thr-11), a protein that is phosphorylated during mitosis. si-scrambled transfected cells demonstrated minimal activated caspase-3 staining similar to control cells. In contrast, several activated caspase-3 positive cells were noted following si-Msi-1 transfection (FIG. 4A). The number of cells positive for activated caspase-3 was estimated as an average of 25 high power fields. siRNA mediated knockdown of Msi-1 in HCT116 cells demonstrated a 4 fold increase in activated caspase-3 positive cells (FIG. 4B). The HCT116 cells transfected with si-scrambled and si-Msi-1 were also subjected to immunohistochemical staining for phosphorylated histone H3, a marker for mitosis. The si-Msi-1 treated cells demonstrated an increased number (greater than 3 fold) of cells positive for phosphorylated histone H3 compared to control cells or si-scrambled treated cells (FIG. 4C, D).

To demonstrate the effect of Msi-1 knockdown on cell cycle analysis and control, si-scrambled and si-Msi-1 transfected HCT116 cells were subjected to cell cycle distribution monitored by Fluorescence activated cell sorting (FACS). DNA content was measured by the PI (propidium iodide) staining. There was no change in the $G_2/M$ phase of cell cycle distribution in the si-scrambled and control cells, whereas an increased number of cell accumulations in the $G_2/M$ phase were observed following si-Msi-1 transfection (FIG. 4E). The percentage of cells in each phase was plotted as a bar graph and revealed a significant decrease in the percentage of $G_0$-$G_1$ phase and an increase in $S_1$ phase cells treated with si-scrambled compared to control cells. However, there was a significant decrease in the $G_0$-$G_1$ and $S_1$ phase in si-Msi-1 treated cells. Furthermore, a significant increase in the percentage of cells in $G_2/M$ was observed following si-Msi-1 transfection (FIG. 4F). Thus, knockdown of Msi-1 resulted in changes in cell cycle distribution compared to control or scrambled si-RNA treated cells.

Knockdown of Msi-1 augments radiation-induced apoptosis. To determine whether si-Msi-1 can sensitize cells to radiation injury, cells transfected with si-scrambled and si-Msi-1 were subjected to 12 Gy γ-irradiation. By 24 h after radiation, cells were evaluated immunohistochemically for activated caspase-3 and phosphorylated histone H3 (Thr 11). si-scrambled treatment did not affect radiation-induced apoptosis, whereas knockdown of Msi-1 increased the number of activated caspase-3 positive cells compared to cells treated with radiation alone (FIG. 5A). There was a 4-fold induction of apoptosis in the si-Msi-1 combined with radiation treated cells compared to cells treated with radiation alone (FIG. 5B). These data demonstrate that si-Msi-1 is an attractive candidate as a potential adjuvant to radiation in the treatment of colon cancer. Similarly, cells were stained for phosphorylated histone H3 to assess mitosis. A nearly 2.3 fold increase in phosphorylated histone H3 staining was observed in cells treated with si-Msi-1 and radiation compared to the cells treated with radiation alone (FIGS. 5C&D). These data further illustrate that knockdown of Msi-1 triggers both apoptosis and mitosis, suggestive of mitotic catastrophe (Castedo et al., 2004; and Ueno et al., 2006).

Knockdown of Msi-1 results in mitotic catastrophe. As a result of the observation that knockdown of Msi-1 resulted in increased apoptosis coupled with mitosis in vitro and given the reduced size of tumors in the xenograft study, the inventors hypothesized that some cells were undergoing mitotic catastrophe. To confirm this, control, si-scrambled and si-Msi-1 treated xenograft tumors were stained for activated caspase-3, TUNEL for detection of apoptosis, and phosphorylated histone H3 for the detection of mitosis. Tumors treated with si-Msi-1 demonstrated an increased number of cells positive for phosphorylated histone H3 (FIG. 6A), activated caspase-3 (FIG. 6B), and TUNEL (FIG. 6C). Furthermore, siRNA mediated knockdown of Msi-1 in the tumors resulted in mitotic catastrophe as evidenced by cells positive for both TUNEL and phosphorylated histone H3 (FIG. 6D). It was found that approximately 20-25% of the apoptotic cells in the tumors undergo mitotic catastrophe following treatment with si-Msi-1.

Furthermore, it was found that most cells positive for phosphorylated histone H3 and TUNEL in the tumor xenografts treated with Msi-1 siRNA were negative for msi-1 as demonstrated by the lack of co-staining (FIG. 7A—Msi-1 co-stained with phosphorylated histone H3; FIG. 7B—Msi-1 co-stained with TUNEL). The nuclear stain was performed using Hoechst 33342.

siRNA mediated downregulation of Msi-1 leads to downregulation of Notch-1 and upregulation of $p21^{WAF1}$. Control, si-scrambled and si-Msi-1 treated tumor xenografts were immunohistochemically stained for Notch-1. Evidence of nuclear and cytoplasmic Notch-1 was found in control and si-scrambled treated tumors, whereas in the tumor xenografts treated with si-Msi-1, there was a loss of Notch-1 staining (FIG. 8A-C). This was further confirmed by Western blot analyses of cells treated with either si-scrambled or si-Msi-1. Downregulation of Notch-1 and cleaved Notch-1 was also observed by Western blot analysis (FIG. 8D). Next, tumor xenografts were stained for $p21^{WAF1}$. There was increased expression of $p21^{WAF1}$ in tumor xenografts treated with si-Msi-1 compared with control or scrambled siRNA treated tumor xenografts (FIG. 8E-G). This was further confirmed by Western blot analyses of the tumor xenografts. Upregulation of $p21^{WAF1}$ was found in si-Msi-1 treated tumors compared to control or si-scrambled treated tumors. Actin was used as loading control (FIG. 8H).

Expression pattern of CD133/AC133 in HCT116 cells and tumor xenografts. Human colon cancer-initiating cells (CC-IC) within tumors are capable of initiating and sustaining neoplastic growth. The CD133 positive cell population in colon tumors is thought to identify these cancer initiating cells which exhibit the capacity for self-renewal, differentiation and establishment of tumor heterogeneity (O'Brien et al., 2007; and Ricci-Vitiani et al., 207). HCT116 cells and HCT116 colon cancer tumor xenografts were immunohistochemically stained for CD133. CD133 was found to be ubiquitously expressed in HCT116 cells in tissue culture (FIG. 9). In tumor xenografts, many of the cells were positive for CD133, and a subset of those cells were also positive for Msi-1 (FIG. 10).

Expression of Msi-2 in HCT116 cells and tumor xenografts. Msi-2 is a structural homolog of Msi-1. Msi-2 expression was determined in HCT116 cells. HCT116 cells were immunostained for Msi-2 and found to be ubiquitously expressed (FIG. 11). Msi-2 expression was also determined in xenografts, as was whether Msi-2 expression was affected following knockdown of Msi-1. Total RNA isolated from tumor xenografts was subjected to real-time RT PCR for Msi-2. There was no change in Msi-2 mRNA expression in Msi-1 siRNA treated tumor xenografts compared with control or scrambled siRNA (FIG. 12). This demonstrates that the si-Msi-1 specifically knocks down Msi-1 and not Msi-2. Furthermore, inhibition of tumor growth has no effect on Msi-2.

Discussion of Example 1

There is increasing evidence demonstrating the role of RNA binding proteins in cell proliferation and/or apoptosis by regulating the translation of key factors such as protooncogenes and tumor suppressors. Several RNA binding proteins involved in tumorigenesis are overexpressed during the various stages of cancer. Msi-1, initially identified as a neuronal stem cell marker and more recently identified as a putative intestinal stem cell and early lineage marker, is upregulated in tumors of $APC^{min/+}$ mice (Potten et al., 2003). It has been postulated that gut tumors arise from stem cells expressed at the base of intestinal and colonic crypts. Msi-1, is also upregulated in brain tumors, including medulloblastoma and gliomas (Hemmati et al., 2003; and Yokota et al., 2004). The demonstration of a functional role of Msi-1 in tumorigenesis has implications in stem cell biology as well as cancer research. In the present example, it is demonstrated that expression of Msi-1 mRNA is increased in human colon cancer tumors compared to its paired uninvolved tissue. While each colon tumor differs in its Msi-1 expression, in the present example these data demonstrate that Msi-1 may be involved in majority of the tumor formations. In tumor xenografts derived from HCT116 cells grown in nude mice, treatment with Msi-1 siRNA arrested tumor growth completely and Msi-1 was lost in the treated tumors. These results demonstrate that Msi-1 is an important regulator of tumor growth.

To further understand mechanistically the role of Msi-1 in tumorigenesis, HCT116 cells were transfected with si-Msi-1, and proliferation was assessed. A nearly 30% reduction in proliferation was observed following 45% Msi-1 knockdown. It has been previously demonstrated that Msi-1 enhances cell proliferative capacity through direct binding and regulation of $p21^{WAF1}$ mRNA. Furthermore, overexpression of Msi-1 leads to decreased $p21^{WAF1}$ in HEK293 cells (Battelli et al, 2006). Moreover, following knockdown of Msi-1 in tumor xenografts, upregulation of $p21^{WAF1}$ was observed. Taken together these data demonstrate that Msi-1 regulates cancer cell proliferation. This may be one of the mechanisms responsible for the tumor growth arrest observed in the xenograft model. Thus Msi-1 inhibition has emerged through the presently disclosed and claimed invention as an attractive target for anti-cancer therapy.

In this example, a small increase in cell proliferation was found following si-scrambled transfection. Therefore, 3 si-scrambled siRNAs and 2 Msi-1 siRNAs were tested. The 3 scrambled siRNAs all demonstrated a similar increase in proliferation in cells transfected with TRANSFECTOL™ and DOPC (transfection reagent used for tumor xenograft study) compared to transfection reagent controls. This explains the increased tumor volume following scrambled siRNA treatment of the tumor xenografts compared to treatment with transfection reagent alone. Similarly both Msi-1 siRNAs demonstrated a significant reduction in proliferation compared to scrambled siRNAs and transfection reagent controls. Moreover, the scrambled siRNA demonstrated a decreased $G_0$-$G_1$ population and increased S1 population compared to transfection reagent treatment alone. Taken together, these data demonstrate potential off-target effects of the scrambled siRNA oligo transfection.

Nuclear translocation of Notch may contribute to increased tumorigenesis, by increasing proliferation and inhibiting apoptosis (Artavanis-Tsakonas et al., 1999). Cells over expressing Msi-1 have been reported to demonstrate nuclear translocation of Notch. This is achieved by translational repression of m-Numb, an inhibitor of Notch (Kanemura et al., 2001; Sakakibara et al., 1996; and Imai et al., 2001). In this example, transfecting HCT116 cells with si-Msi-1 lead to increased apoptosis, as evidenced by increased activated caspase-3 and TUNEL staining. Interestingly, there was increased staining for phosphorylated histone H3 (a marker for mitosis) in the cells following knockdown of Msi-1 as well. Furthermore, si-Msi-1 transfection of HCT-116 cells resulted in an increased number of cells at $G_2$/M phase of the cell cycle. It has been demonstrated that increased expression of p21$^{WAF1}$ leads to apoptosis and $G_2$/M arrest in various cell lines including human cervical cancer (Niculescu et al., 1998; and Tsao et al., 1999). This example demonstrates that following knockdown of Msi-1, there is increased expression of p21$^{WAF1}$ which leads the cells to $G_2$/M arrest. In addition, when the cells treated with si-Msi-1 were subjected to radiation injury, an augmentation of apoptosis was observed. Apoptosis caused by reduced Msi-1 leads to $G_2$/M arrest and mitotic catastrophe by nuclear translocation of cyclin B1 (Curry et al., 2007). Furthermore, although there was evidence of Notch-1 in the nucleus and cytoplasm of the cells in the control or scrambled siRNA treated tumors, this expression was lost in the tumors treated with Msi-1 siRNA. Additionally, there was loss of cleaved Notch-1 in HCT-116 cells transfected with si-Msi-1 even at 10 nM, as demonstrated by Western blot analyses. These data demonstrate that reduction of Msi-1 drives cells to undergo apoptosis/mitotic catastrophe, by reducing Notch-1 expression. This may explain the reduced tumor size in xenografts.

A hallmark of mitotic catastrophe is entry of cells into mitosis despite the presence of damaged DNA, resulting in activation of apoptotic cell death pathway (Ueno et al., 2006). There is evidence that inhibition of Notch signaling leads to mitotic catastrophe. Inhibition of Notch leads to increased G2/M phase arrest, and accumulation of cyclin B1. The initial step in mitotic catastrophe is evidence of apoptosis and DNA damage in a cell, which is undergoing mitosis (Curry et al., 2007). There is evidence that increased expression of Msi-1 increases Notch (Kanemura et al., 2001). It has been shown herein that inhibition of Msi-1 following siRNA transfection in HCT116 cells as well as tumor xenografts lead to inhibition of Notch-1. Furthermore, si-Msi-1 treated tumors demonstrated increased phosphorylated histone H3, activated caspase-3, as well as TUNEL staining. Several cells stained for both phosphorylated histone H3 and TUNEL, with aberrant DAPI staining in the nucleus. There were few caspase-3 positive cells (20-25%) that also stained for phosphorylated histone H3. These cells may represent stem/progenitor-like cells within the tumor and the presence of Msi-1 enhances tumorigenesis, whereas inhibition of Msi-1 in these particular cells leads to mitotic catastrophe (evidenced by absence of Msi-1 in the cells positive for phosphorylated histone H3 and TUNEL), resulting in increased apoptosis and tumor growth arrest.

Recently, colon cancer-initiating cells (CC-IC) have been described (O'Brien et al., 2007; and Ricci-Vitiani et al., 2007), and these cells are a subset of CD133 positive cells within colon cancer tumors. It has been postulated that these cells may define a cancer stem cell population. Msi-1 is a putative stem/progenitor cell marker in the intestine, and both Msi-1 and CD133 expressing cells were demonstrated in tumor xenografts generated from HCT116 cells. Furthermore, there were rare cells where Msi-1 and CD133 were co-expressed. It is tempting to speculate that these cells might represent cancer stem cells or at the very least cancer progenitor cells. Nevertheless, knockdown of Msi-1 results in xenograft tumor growth arrest.

Collectively Example 1 indicates that Msi-1, a putative stem/progenitor cell marker is also an important positive regulator of cell proliferation and inhibitor of apoptosis. Knockdown of Msi-1 in colon cancer cells results in mitotic arrest and simultaneously leads the cell to undergo apoptosis, consistent with mitotic catastrophe. This activity further augments radiation-induced apoptosis. Taken together, these data demonstrates that Msi-1 promotes tumorigenesis by inhibiting mitotic catastrophe particularly in stem/progenitor cells. Furthermore, Msi-1 regulates p21$^{WAF1}$ and Notch-1 signaling, as demonstrated by the siRNA mediated knockdown of Msi-1 that resulted in decreased Notch-1 and cleaved Notch-1 expression with increased expression of p21$^{WAF1}$. These data taken together highlight a previously unappreciated function of Msi-1, and identify Msi-1 as a novel candidate for therapeutic intervention either alone or in combination with radiation therapy.

Example 2 siRNA mediated knockdown of Msi-1 results in reduced angiogenesis. Several reports have demonstrated the positive role of angiogenesis in tumorigenesis (see, for example, Larcher et al., 1998). Several targets that regulate angiogenesis have been identified; vascular endothelial growth factor (VEGF) (Takei et al., 2004) is one among them. Therefore, the effect of Msi-1 on VEGF mRNA expression was analyzed.

Tumor xenografts treated with si-msi-1 demonstrated a significant decrease in VEGF mRNA expression compared with control untreated or si-scrambled treated tumors (FIG. 13). si-msi-1 treated tumors demonstrated a decreased CD31 immunohistochemical staining for micro vessels. Decreases were observed in number as well as size of the blood vessels of si-msi-1 treated tumors compared to the blood vessels associated with control or si-scrambled treated tumors (FIG. 14), as indicated by the arrows. These data demonstrate that msi-1 plays an important role in angiogenesis and that knockdown of msi-1 is beneficial for prevention and/or reduction of angiogenesis.

Prostaglandin $E_2$ (PGE$_2$) induces Msi-1. PGE$_2$, a product of the cyclooxygenase (COX) reaction, stimulates the growth of colonic epithelial cells. Furthermore, PGE$_2$ elevates tumor incidence in various murine models for colorectal cancer (Kawamori et al., 2003; Wang et al., 2004); in addition, cell culture experiments have implicated PGE$_2$ and PGE$_2$ receptor-dependent signaling in the stimulation of colon cancer epithelial cell growth (Shao et al., 2003). In this example, the effect of PGE$_2$ on Msi-1 expression was investigated. HCT116 colorectal cancer cells were treated with 1 µM PGE$_2$ for 1 h. Total RNA isolated was subjected to real-time RT PCR for Msi-1 mRNA expression. A 1.6 fold increase in Msi-1 mRNA was observed following treatment with PGE$_2$ (FIG. 15). This data demonstrates that PGE$_2$ enhances colorectal cancer cell proliferation via enhancement of Msi-1.

Example 3

The present Example demonstrates that RBM3, a ubiquitously expressed serine- and glycine-rich protein, is a protooncogene that binds to COX-2 ARE and regulates COX-2 mRNA stability and translation (Danno et al., 1997). RBM3 level is upregulated in human tumors, and expressing the protein in non-transformed cells induces the cells to grow in an anchorage-independent manner. In contrast, downregulating RBM3 with specific siRNA decreases HCT116 colon adenocarcinoma cell proliferation. Moreover, there is an increase in apoptosis and activation of checkpoint-related proteins that enhance cell cycle progression at the level of mitosis suggesting mitotic catastrophe. Furthermore, downregulating RBM3 in nude mice tumor xenografts decreased angiogenesis.

Materials and Methods for Example 3

Plasmids: For mammalian expression, FLAG epitope-tagged RBM3 were generated by cloning the full-length coding region into plasmid pCMV-Tag 2B at the BamH1 and Xho1 restriction sites. Myc epitope-tagged HuR was generated by cloning the full length coding region into plasmid pCMV-Tag 3B at the EcoR1 and Xho1 restriction sites. HuR full length clone in pcDNA 3.1 was a generous gift from Dr. Joan A. Steitz. COX-2 3'UTR entire 2232 nt (FL) cloned in the pGL3 Basic vector was as described earlier (Fan & Steitz, 1998b). Renila luciferase reporter gene plasmid pRL-TK (Promega) was used as control vector for the luciferase assays. All the plasmid DNA were transfected with FuGENE 6 Transfection Reagent (Roche).

Yeast two-hybrid screening: Full-length HuR cDNA was cloned into the yeast vector pGBKT7 (Clontech) as bait at the EcoR1 and Sal1 restriction sites, and performed yeast two-hybrid screening with the human cDNA liver library according to the manufacturer's protocols. To further confirm, the full length RBM3 cDNA was cloned in to yeast vectors pGBKT7 and pGADT7 at the EcoR1 and BamH1 restriction sites, and HuR in pGADT7 at the EcoR1 and Xho1 restriction sites.

Cell culture and treatment: HCT116, SW480 human colon adenocarcinoma, HeLa cervical carcinoma and NIH-3T3 mouse fibroblast cells were obtained from the ATCC and grown in Dulbecco's modified eagle's medium (DMEM) supplemented with 10% fetal bovine serum. To examine RNA stability, HeLa cells were transiently transfected with pCMV-Tag2B plasmids (Stratagene) expressing FLAG-tagged RBM3 and/or FLAG-tagged HuR. Twenty-four h after transfection, the cells were treated with actinomycin D 10 µg/mL to prevent the de novo mRNA synthesis, and total RNA was isolated using Trizol reagent. For stable expression, NIH-3T3 and SW480 cells were stably transfected and colonies isolated following incubation in 800 ?g/ml geneticin.

Anchorage independent growth: NIH-3T3 and SW480 cells transfected with plasmid vector (Vec) or stably expressing RBM3 were suspended in a 0.3% Sea Plaque agarose overlay in DMEM, 5% FBS. The overlay (1.0 ml), consisting of cells, agarose, and medium, was plated at 2000 cells/well in Nunc 10 cm plates over bottom layers of soft agarose (0.8%) containing only DMEM, 5% FBS. Plates were incubated at 37° C. for 7 d. Colonies were counted and photographed.

Recombinant proteins: Recombinant RBM3 and HuR were expressed as N-terminal glutathione S-transferase (GST) fusion proteins from the plasmid pGEX-4T3 (Amersham-Pharmacia) at BamHI and XhoI. Electrophoretic mobility shift assays were performed as previously described (Deschenes-Furry et al., 2005), using a in vitro transcribed $^{32}$P-labeled cRNA encoding the first sixty nucleotides of COX-2 3'UTR.

Silencer RNA: RBM3 siRNA sequence targeting the coding region of RBM3 (nucleotides 470-488, Accession # nm_006743; SEQ ID NO:10) was GGGTATGGATATG-GATATG (SEQ ID NO:11) and a scrambled control siRNA not matching any of the human genes were obtained from Ambion Inc. and transfected using Transfectol™ (Ambion Inc.).

Immunoprecipitation coupled RT-PCR: HCT116 whole cell lysates were prepared following crosslinking with formaldehyde, and immunoprecipitated with anti-RBM3 IgG using Seize X protein A purification kit (Pierce). The pellet and supernatant was subsequently incubated at 70° C. for 1 h to reverse the crosslinks. RNA was isolated and subjected to RT-PCR for COX-2, IL-8 and VEGF.

Flow Cytometric Analysis: HCT116 cells were transfected with si-RBM3 10 and 50 nM for 72 h. The cells were and harvested by trypsinization and washed 6 times with PBS. The single-cell suspensions were fixed using 70% ethanol for 2 h. The cells were centrifuged to remove the 70% ethanol and washed with PBS. The ethanol fixed cells was permeabilized with PBS containing 1 mg/ml propidium iodide (Sigma-Aldrich), 0.1% v/v triton X-100 (Sigma-Aldrich) and 2 mg DNase-free RNase (Sigma-Aldrich) at room temperature. Flow cytometry was done with a FACSCalibur analyzer 3-color (Becton Dickinson, Mountain, View, Calif.), capturing 50,000 events for each sample; results were analyzed with ModFit LT™ software (Verity Software House, Topsham, Me.).

In vitro Protein interaction studies: The study was performed as reported earlier with recombinant GST-HuR or GST-RBM3 (Sureban et al., 2007).

Real Time PCR Analyses: Total RNA isolated either from cells or from the human colorectal tumor samples was subjected to mRNA analysis for various genes wherever indicated as described earlier. β-actin was used as internal control. Primer sequences are as follows:

```
β-actin:  Forward: 5'-GGTGATCCACATCTGCTGGAA-3',     (SEQ ID NO: 4)
          Reverse: 5'-ATCATTGCTCCTCCTCAGGG-3',       (SEQ ID NO: 5)

RBM3:     Forward: 5'-CAGTTTCGGACCTATCTCTGAGGT-3',   (SEQ ID NO: 12)
          Reverse: 5'-AAGGTGATGAAACCAAAACCCCT-3',    (SEQ ID NO: 13)

HuR:      Forward: 5'-GTGAACTACGTGACCGCGAA-3',       (SEQ ID NO: 14)
          Reverse: 5'-GACTGGAGCCTCAAGCCG-3',         (SEQ ID NO: 15)

COX-2:    Forward: 5'- GAATCATTCACCAGGCAAATTG- 3',   (SEQ ID NO: 16)
          Reverse: 5'- TCTGTACTGCGGGTGGAACA-3',      (SEQ ID NO: 17)

IL-8:     Forward: 5'-CTCTTGGCAGCCTTCCTGATT-3',      (SEQ ID NO: 18)
          Reverse: 5'-TATGCACTGAGATCTAAGTTCTTTAGC-3', (SEQ ID NO: 19)

VEGF:     Forward: 5'-AGCGCAAGAAATCCCGGTA-3',        (SEQ ID NO: 20)
          Reverse: 5'-TGCTTTCTCCGCTCTGAGC-3'.        (SEQ ID NO: 21)
```

Western Blotting: HCT116 cells were cultured in a 6 well plates to a confluency of 80% and were treated with EGF (100 ng/mL) for the indicated time. Cells were lyzed and concentration of protein was determined by BCA protein assay (Pierce) and 40 µg of the protein subjected to western blot analysis as described earlier. Antibodies used are rabbit anti-RBM3 antipeptide antibody (YDRYSGGNYRDNYDN (SEQ ID NO:22), Sigma-Genosys), rabbit polyclonal anti COX-2 antibody (Cell Signaling), mouse monoclonal anti-HuR antibody (Santa Cruz). Actin used as internal control for loading was identified using a goat polyclonal IgG (Santa Cruz).

Immunocytochemistry: HeLa cells transfected with plasmid encoding FLAG and Myc tags were stained by immunofluoresence. Tumor xenografts and human multiple tissue slides were immunostained as described herein below.

a. Fluorescent staining. HeLa cells, grown in coverslips were fixed with 10% formaldehyde for 10 min, permeabilized with 0.5% Triton X-100/1% normal goat serum (Jackson ImmunoResearch Laboratory) in PBS. The coverslips were then incubated with primary antibodies [rabbit anti-FLAG (Affinity Bioreagents) and mouse monoclonal anti-Myc (Sigma-Aldrich)] at RT for 1 h. The coverslips were incubated with the secondary antibodies at RT for 1 h. Secondary antibodies were fluorescein isothiocyanate (FITC)-conjugated anti-rabbit IgG for FLAG and Indocarbocyanine (Cy3)-conjugated anti-mouse IgG for Myc (Jackson Immuno Research Laboratories). Nuclei were counterstained with DAPI (Vector laboratories). Slides were examined using a Zeiss Axiaskop 2 MOT plus microscope (Carl Zeiss, Inc.) equipped with a 40× plan neofluar objective and a CCD camera (DAGE-MTI Inc.). A Zeiss Attoarc variable intensity lamp was used with filter sets designed for Cy3, FITC and DAPI. Images were processed using Adobe Photoshop 8.0 software.

b. Immunoperoxidase staining. Paraffin-embedded tissues were freshly cut into 4-μm-thick sections, deparaffinized and treated with citrate buffer in a decloaking chamber 90° C. Incubated with Avidin/Biotin blocking reagent (Vector Lab.) for 20 min. The sections were incubated overnight with either a rabbit anti-COX-2 antibody (Cell Signaling), a rabbit anti-RBM3 peptide antibody, or anti-CD31 antibody (BD Pharmingen). After the overnight incubation with the primary antibody, the sections were treated with respective secondary antibody (Jackson Immuno Research Laboratories) for 1 h. The sections were subsequently incubated with SA-HRP (Dako) and visualized with DAB (Sigma-Aldrich). Finally, the sections were counterstained with hematoxylin (Richard Allan Scientific).

Luciferase reporter gene assay: Luciferase reporter assay was performed with plasmid encoding RBM3 and HuR as described earlier (Sureban et al., 2007).

Cell Proliferation assay: RBM3-targeted siRNA was transfected with $1 \times 10^5$ HCT116 cells and plated simultaneously in a 96 well plates. Cell numbers were estimated after 48 h transfection as described earlier (Landegren, 1984).

Xenograft tumor model: siRNA was administered into the xenografts after incorporation into DOPC (1,2-Dioleoyl-sn-Glycero-3-Phosphocholine) (Avanti Polar Lipids) (Landen et al., 2005) generated by injecting HCT116 cells ($6 \times 10^6$ cells) subcutaneously into the flanks of female athymic nude mice (NCr-nu) and housed in specific pathogen-free conditions. Tumors were measured with calipers and calculated volume as (length×width$^2$)×0.5. The tumors reached 1000 mm$^3$ after 15 days of injection of cells. These tumors were injected with 50 μl (5 μM) on every third day from day 15 for a total of 5 doses. Data are represented as ±s.e.

Statistics. All the experiments were performed in triplicate. The data was analyzed by Student's t-test. Where indicated, the data is presented as mean±SEM.

Results for Example 3

RBM3 is induced in colon cancers. RBM3 regulates global mRNA translation by interacting with the 60S ribosome (Danno et al., 1997; Derry et al., 1995; Dresios et al., 2005). In addition, RBM3 was identified through its binding to AU-rich sequences in COX-2 3'UTR (Cok and Morrison, 2001). Since COX-2 is a significantly upregulated in cancers, RBM3 expression in colon cancers was first examined. There was a stage dependent increase in RBM3 mRNA levels compared to the paired uninvolved tissues, with highest levels observed in later stages (FIG. 16A). HuR was also significantly upregulated in the cancers, confirming previous reports (Dixon et al., 2001; Erkinheimo et al., 2003; Nabors et al., 2001). Details of colorectal adenocarcinoma and specific expression patterns for the three genes are presented in FIG. 17. Western blot analyses for protein expression confirmed that both RBM3 and HuR are expressed at higher levels in the tumors, with at least a 10-fold increase in RBM3 at every stage (FIG. 16B). RBM3 expression was also determined by immunohistochemistry of paraffin-embedded tissues. In normal, human colonic epithelium, a single cell within the crypt demonstrated RBM3 expression, which was nuclear (FIG. 16C). However, in the cancer tissues, the expression was widespread, and both nuclear and cytoplasmic, especially at the later stages of tumorigenesis (FIG. 16C). In addition, high levels of RBM3 expression was observed in other tumors, including pancreas, breast, lung, ovary and prostate (FIG. 16D). A subset of these tumors also showed high level expression of HuR. Thus, expression of RBM3 is significantly induced in cancers and is localized in both the nucleus and cytoplasm.

RBM3 overexpression induces anchorage-independent growth. To determine whether RBM3 overexpression affects growth rate, NIH3T3 cells stably expressing RBM3 were generated. There was a significantly higher level of proliferation in the RBM3-transfected cells when comparing to the wild-type, vector-transfected controls (FIG. 18A). Next, it was tested whether the RBM-3 expressing cells can grow in an anchorage-independent manner, a characteristic of transformed cells. All the fast growing RBM3 expressing cells show anchorage-independent phenotype and grow in 0.3% agar (FIG. 18B). More importantly, the cells exhibited obvious morphological differences. The NIH-3T3-RBM3 cells formed tight, densely packed multi-cellular spheroids where single cells could not be distinguished. Moreover, when the colony size was compared to that produced by HT-29 colon adenocarcinoma cells, the NIH3T3-RBM3 colonies were significantly bigger, demonstrating an aggressive phenotype (FIG. 18C). To determine whether RBM3 overexpression affected growth of cells that were already transformed, SW480 colon cancer cells were stably transfected with RBM3. Cells overexpressing RBM3 had higher levels of proliferation when compared to vector transfected controls and formed larger colonies in soft agar (FIG. 18 D-F). Moreover, the colonies with RBM3 overexpression were significantly larger than that observed with vector transfected or untransfected controls (FIG. 19 E, F). Western Blot analyses demonstrated that expression of COX-2, VEGF and cyclin D1 was upregulated in both NIH-3T3 and SW480 cells that have RBM3 overexpression (FIG. 19G). Together, these data demonstrate that RNA binding protein RBM3 is a protooncogene that induces anchorage independent growth when overexpressed.

RBM3 is essential for tumor growth. Next, the effect of downregulating RBM3 expression on proliferation was determined. RBM3 protein levels in HCT116 colon adenocarcinoma cells were significantly downregulated following transfection with an RBM3-specific, but not scrambled siRNA (FIG. 19A,B). Furthermore, COX-2 mRNA and proteins levels were decreased in these cells (FIG. 19A,C). Next, the effect of RBM3 downregulation on HCT116 cell proliferation was determined. While the scrambled siRNA did not affect proliferation, siRNA-mediated downregulation of RBM3 significantly reduced it (FIG. 18D). A 50% reduction in HCT116 cell proliferation was observed with 50 nM siRNA. To determine whether this was due to loss of COX-2, cells were also treated with PGE$_2$, the product of COX-2 enzyme activity. There was significantly higher levels of proliferation in cells also treated with PGE$_2$, demonstrating that the decreased proliferation resulting from reducing RBM3 levels is due to decreased COX-2-mediated PGE$_2$ synthesis. Similar results were observed with HT-29 cells (data not shown). Next, the effect of RBM3 downregulation on the growth of HCT116 tumor cell xenografts was determined in nude mice. After the tumors were allowed to develop (15 d), siRNA was injected a total of 5 times at an interval of 3 days. Tumors that received either liposome preparation without any siRNA or those that included the scrambled siRNA continued to grow, with tumor volume reaching 4×10$^3$ mm$^3$ and 6×10$^3$ mm$^3$, respectively (FIG. 19E). On the other hand, tumors that received RBM3-specific siRNA were arrested in growth. RBM3 silencing in the tumors was confirmed by Real Time PCR and immunohistochemistry analyses (FIG. 19F,G). In addition, there was a 5-fold decrease in COX-2 mRNA when compared to the controls in the xenografts where RBM3 was knocked down (FIG. 19F). Furthermore, while COX-2 protein was widely expressed in the controls, the expression was significantly reduced in tumors lacking RBM3 (FIG. 19G). These data demonstrate that RBM3 is essential for COX-2 expression in vivo. COX-2 derived PGE$_2$ regulates expression of angiogenesis inducing factors VEGF and IL-8. Real Time PCR analyses demonstrated a significant decrease in VEGF and IL-8 mRNA in the RBM3 targeted tumors, the amounts similar to that seen with COX-2 (FIG. 19F). Furthermore, staining for CD-31, a platelet endothelial cell adhesion molecule that marks the endothelial cells in blood vessels demonstrated a 70% reduction in microvessel density in the RBM3-targeted tumors (FIG. 19G, 20). Together, these data demonstrate that targeting RBM3 effectively suppressed capillary formation through decreased expression of angiogenic factors, resulting in loss of tumor growth.

RBM3 is necessary for overcoming mitotic catastrophe. To characterize the inhibition of cell growth by RBM3 depletion, cell cycle progression was analyzed. While transfection with the scrambled siRNA did not affect the cell cycle profile after 3 d, RBM3 depletion increased the percentage of cells with 4N DNA content, demonstrating that RBM3-depleted cells are blocked at G$_2$/M phase (FIG. 21A). While the control and scrambled siRNA transfection resulted in 12.7% cells in the G$_2$/M phase, RBM3-targeted cells had 17.1% cells in the G$_2$/M phase when 10 nM RBM3 siRNA was transfected (data not shown), which was further increased to 19% with 50 nM RBM3 siRNA (FIG. 21A, 22). However, further treatment of cells with PGE$_2$ in the setting of RBM3 suppression resulted in only 12.2% of the cells in G$_2$/M phase, demonstrating that PGE$_2$ is able to override the RBM3-mediated effects on cell cycle. To determine whether the cells were undergoing apoptosis, the cells were stained by the TUNEL technique and for activated caspase-3. The number of apoptotic cells following RBM3 knockdown was significantly higher than that seen with the scrambled siRNA (FIG. 21B). Furthermore, treatment with PGE$_2$ resulted significantly lowered the number of apoptotic cells, demonstrating that PGE$_2$ is able to protect the cells from undergoing apoptosis due to loss of RBM3. This further implies that COX-2 expression due to the action of RBM3 in protects the cells from apoptosis in an autocrine manner through PGE$_2$. Further conformation was obtained when western blot analyses were performed, which demonstrated increased caspase-3 activation, that was suppressed by PGE$_2$ (FIGS. 23-24). To gain further insights into the mechanism of G$_2$/M cell cycle coupled apoptosis upon suppression of RBM3 expression, western blot analyses was performed for Cdc25c, a protein that catalyzes the activation of the Cdk1:cyclin B1 kinase complex which is believed to be a rate-limiting step for entry into mitosis (Mailer, 1991; Millar & Russell, 1992). Suppression of RBM3 induced Cdc25c protein levels (FIG. 21C). In addition, there was an increase in the level of cyclin B1, which were higher than that observed in the control or scrambled siRNA transfected cells (FIG. 21C). Similar results were obtained with extracts from the tumor xenografts. There was also increased cyclin B1 in the tumors in which RBM3 expression was suppressed (FIG. 21C). Furthermore, in tumors lacking RBM3, there was increased nuclear accumulation of cyclin B1 (FIG. 21D). Two kinases Chk1 and Chk2 that are intermediaries of DNA damage checkpoint and activated by phosphorylation on Ser-345/Ser-317 and Thr-68, respectively have been implicated in Ser-216 phosphorylation of Cdc25c (Bulavin et al., 2002; Canman, 2001; Walworth, 2001). In addition phosphorylation of p53 protein at Ser-15 is critical for p53 protein stabilization and for activating its apoptotic function and G$_2$/M checkpoint (Taylor & Stark, 2001). Representative immunoblots for phospho-Chk1 (Ser-345), phospho-Chk2 (Thr-68) and phosphor-p53 (Ser-15) showed increased phosphorylation of all three proteins over control in the RBM3 depleted cells in culture and in the tumors (FIG. 21C). Collectively, these data imply that RBM3-depleted HCT116 cells undergo massive apoptosis while in the G$_2$/M phase of the cell cycle, which is in part due to loss of COX-2 derived PGE$_2$. To confirm that the cells were undergoing apoptosis while in mitosis, the xenograft cancer tissues were co-stained for phosphorylated histone H3 (Thr-11), a protein that is phosphorylated during mitosis and for DNA damage by TUNEL. Many cells in the tumor, in which RBM3 expression was suppressed, demonstrated staining for both phospho-H3 and were TUNEL positive (FIG. 21E). There was also an increase in phospho-H2AX staining in the RBM3-depleted tumors (FIG. 25). Taken together, these data demonstrate that the cells in which RBM3 expression is suppressed were undergoing mitotic catastrophe because they are in the process of mitosis while at the same time undergoing apoptosis.

RBM3 is a nucleocytoplasmic shuttling protein that stabilizes COX-2, VEGF and IL-8 mRNA. Previous studies have demonstrated that COX-2 derived PGE2 induces cells to divide by enhancing mitosis (Andreis et al., 1981; Munkarah et al., 2002; Wu et al., 2005). Furthermore, treatment of colon cancer cells with NS-398, a COX-2 selective inhibitor increased the number of cells in the G2/M phase, while decreasing those in the G0/G1 phase (Yamashita et al., 2003). This demonstrates that mechanisms to increase COX-2 expression would result in protecting the cells from mitotic catastrophe. To identify the mechanism by which RBM3 inhibits mitotic catastrophe, the cellular functions of RBM3 were determined next. Previous studies identified HuR and RBM3 as being in a complex bound to AU-rich sequences in COX-2 3'UTR (Cok and Morrison, 2001). Here, it was observed that RBM3 interacts with HuR in a yeast two hybrid analysis (FIG. 26A). Moreover, RBM3 was isolated in a yeast two-hybrid screen using HuR as bait (data not shown). To confirm that the two proteins interact, HuR was generated by in vitro translation in the presence of $^{35}$S-methionine, and incubated with recombinant GST-HuR or GST-RBM3 fusion proteins, followed by affinity purification with a glutathione-sepharose column. Radiolabeled HuR bound to RBM3, demonstrating that the proteins can interact in solution in the absence of RNA (FIG. 26B). To examine the interaction of HuR and RBM3 in mammalian cells, immunostaining was performed following transient transfection of HeLa cells with N-terminal myc epitope-tagged HuR and N-terminal FLAG epitope-tagged RBM3 plasmids. It was found that the two proteins colocalize, predominantly in the nucleus (FIG. 26C). HuR is primarily nuclear, but can be induced to redistribute from the nucleus to the cytoplasm (Fan & Steitz, 1998a). Furthermore, cytoplasmic HuR expression in cancer cells has been suggested to be a prognostic marker for cancers (Denkert et al., 2006a; Erkinheimo et al., 2003; Erkinheimo et al., 2005; Heinonen et al., 2005; Lopez de Silanes et al., 2003). Given the strong nuclear colocalization of HuR and RBM3, and that there is increased cytoplasmic localization of the protein in cancers it was next determined whether RBM3 also exhibits shuttling activity. A heterokaryon assay was performed, where Flag-tagged RBM3 or HuR were transfected in human HeLa cells and fused the cells with the murine NIH3T3 cells. RBM3, like HuR was found in both the human and murine nuclei implying that RBM3 is a nucleocytoplasmic shuttling protein (FIG. 26D). HuR shuttles to the cytoplasm where it can stabilize certain transcripts such as COX-2 (Fan & Steitz, 1998a; Fan & Steitz, 1998b; Lopez de Silanes et al., 2003; Nabors et al., 2001; Peng et al., 1998). Since knockdown of RBM3 decreased COX-2 mRNA levels, and RBM3 is a nucleocytoplasmic protein, it was next determined whether RBM3 is able to regulate COX-2 expression. For this, the effect of ectopic transient FLAG-tagged RBM3 and FLAG-tagged HuR on COX-2, IL-8 and VEGF mRNA levels was determined in HCT116 cells. Both RBM3 and HuR alone significantly induced the endogenous expression of COX-2 mRNA (FIG. 26E). While the steady state levels of endogenous COX-2 mRNA was increased by approximately 7-fold in the presence of RBM3 and HuR, there was further increase to 10-fold when RBM3 and HuR are coexpressed (FIG. 26E). Furthermore, western blot analyses demonstrated increased COX-2 protein expression in the cells that expressed FLAG-tagged RBM3 (FIG. 26F). Similar results were obtained with IL-8 (FIG. 26E). However, while both RBM3 and HuR induced VEGF expression when expressed alone, there was no additive effect when the two proteins were coexpressed (FIG. 26E,F). These data demonstrate that RBM3 and HuR coordinate their functions to induce COX-2, VEGF and IL-8 gene expression.

RBM3 enhances COX-2 VEGF and IL-8 mRNA stability and translation. HuR is an RNA binding protein that encodes three RNA binding domains of the RNA Recognition Motif (RRM) family. It mediates nucleo-cytoplasmic transport, mRNA stability and translation functions following binding to ARE sequences in the 3'UTR of rapidly degraded transcripts such as COX-2, VEGF and IL-8. RBM3 is a glycine-rich protein that also encodes a single RRM type RNA binding domain suggesting that it might also modulate RNA stability function in a similar manner (Derry et al., 1995; Sutherland et al., 2005). Electrophoretic mobility shift assays demonstrated the ability of recombinant GST-RBM3 protein binding to ARE sequences located in the first sixty nucleotides of the COX-2 3'UTR (FIG. 27A). To confirm that increased expression of RBM3 resulted in increased RBM3 binding to the COX-2 mRNA, a coupled immunoprecipitation followed by RT-PCR was performed. There was a significantly higher level of RBM3-bound COX-2 mRNA compared to vector-transfected cells (FIG. 27B). Similar results were obtained with VEGF and IL-8. Since HuR is a RNA stabilizing protein, it was next determined whether RBM3 is also involved in regulating the mRNA decay pathway. RBM3 and HuR were transiently overexpressed in HCT116 cells following which, actinomycin D was added to inhibit de novo synthesis and RNA was isolated to determine COX-2 mRNA levels. In cells transfected either RBM3 or HuR alone, there was increased stability of COX-2 mRNA, the half-life increasing from 60 min in control vector transfected cells to 5 h in the RBM3 or HuR expressing cells (FIG. 27C). Furthermore, when RBM3 and HuR were co-expressed, COX-2 mRNA stability increased to 8 h (FIG. 27C). Similar results were obtained with IL-8 and VEGF mRNA. The half-life of IL-8 mRNA increased from 0.5 h to 1 h with either RBM3 or HuR, which was further increased to 4 h when the two proteins were co-expressed (FIG. 27C, middle panel). The half-life of VEGF mRNA was increased from 30 min to 8 h with either RBM3 or HuR, which was further increased to >8 h when the two proteins were co-expressed (FIG. 27C, right panel). These data, taken together demonstrate that RBM3 interacts with HuR to increase the mRNA stability of key oncogenic factors including COX-2, IL-8 and VEGF.

To determine whether RBM3-mediated increased the translation of COX-2 mRNA occurs through the 3'UTR, the effect of the transiently expressed RBM3 and HuR on a chimeric luciferase-COX-2 3'UTR mRNA was determined (FIG. 27D). Both RBM3 and HuR significantly induced luciferase mRNA expression, which was further increased when both RBM3 and HuR are co-expressed (FIG. 27E). A similar increase in luciferase activity was also observed with cotransfection of RBM3 and HuR (FIG. 27F). In contrast, neither RBM3 nor HuR affected the steady state levels of control luciferase mRNA that lacked the COX-2 3'UTR (FIG. 27E) or the luciferase levels that was expressed from this control transcript (FIG. 27F). These data demonstrate the ability of RBM3 and HuR to increase the translation of COX-2 mRNA via its 3'UTR, either alone or in partnership with each other.

Discussion of Example 3

Although it is becoming apparent that posttranscriptional events of mRNA stability and translation contribute to the development and progression of malignant tumors, the mechanisms that regulate these processes especially in inflammation and cancer are not clearly understood. A key sequence that is found in 3'UTR of transcripts encoding oncoproteins, cytokines and transcription factors and is a target for selective mRNA degradation are the AREs (Chen & Shyu, 1995; Chen et al., 1995). However, not much is known about the RNA binding proteins that regulated through these elements. HuR is the best characterized factor (Fan & Steitz, 1998b; Myer et al., 1997; Peng et al., 1998). HuR is a critical protein in regulating the stability of COX-2, IL-8 and VEGF mRNAs, resulting in their increased expression thereby enhancing tumorigenesis. Several tumors have been shown to have an increased expression of HuR (Blaxall et al., 2000; Denkert et al., 2006a; Denkert et al., 2004; Dixon et al., 2001; Erkinheimo et al., 2005; Heinonen et al., 2005; Nabors et al., 2001). However, more recently it is believed that cytoplasmic localization, rather than amount of HuR is an important feature that governed the activity of the protein (Blaxall et al., 2000; Denkert et al., 2006a; Denkert et al., 2006b; Denkert et al., 2004; Erkinheimo et al., 2003; Erkinheimo et al., 2005; Heinonen et al., 2005). Here, RBM3 has been identified as a novel interacting partner for HuR, whose expression is not only significantly upregulated in tumors, but also is localized in the cytoplasm. A more comprehensive study to determine whether there is a correlation between protein localization and tumor aggressiveness is required. Nevertheless, The present Example demonstrates a trend in RBM3 expression similar to that observed with HuR, implying a similar if not redundant function.

Nucleo-cytoplasmic shuttling of RBM3 is similar to that of the hnRNP proteins that are required for mRNA export from the nucleus (Carpenter et al., 2006; Hacker & Krebber, 2004;

Pinol-Roma, 1997; Shyu & Wilkinson, 2000). Previously, Shyu and colleagues have speculated that HuR may bind to ARE-containing mRNAs and remain associated during transit through the nuclear envelope (Fan & Steitz, 1998b). The possibility exists that RBM3 might interact with ARE-transcripts during its transit to the cytoplasm. In addition, since, RBM3 is a global translation inducer (Dresios et al., 2005), it is tempting to speculate that RBM3 not only binds to these ARE containing RNAs and transports them to the cytoplasm, but also loads them on to ribosomes to induce translation.

The observation that the increase in RBM3 expression is dependent on the tumor stage demonstrates that it may play a role in tumorigenesis. Indeed, it was observed that there is a significantly higher level of RBM3 expression in HCT-116 cells in the tumor xenograft as compared to the cell in culture (data not shown). In addition, RBM3 overexpression induced NIH3T3 cells to grow in an anchorage independent manner. Furthermore, when RBM3 expression was suppressed in the xenograft, there was a complete shut down of tumor growth. Previous studies from the Gorospe group have shown that knockdown of HuR also results in smaller tumors (Lopez de Silanes et al., 2003). However, the inhibition was not as pronounced with HuR suppression as that observed here with RBM3 suppression. This might be because HuR levels were only decreased by 35-50% in that study. In this regard, it should be noted that both proteins influence the expression of COX-2, IL-8 and VEGF expression. These factors play a major role in tumor cell growth and in angiogenesis, which are essential for the behavior of the tumor. Hence, further characterization of the role of HuR and RBM3 in tumorigenesis will be useful in understanding their contributions to the aggressive phenotype.

Not much is known about the pathways that regulate mitotic catastrophe and the role of apoptosis in the process. Previous studies have suggested that apoptosis is an early event in the mitotic catastrophe process, in such cases there was an arrest at the $G_2$/M phase (Chen et al., 1999; Ning & Knox, 1999; Wahl et al., 1996). $G_2$/M transition is regulated by the mitosis-promoting factor, cyclin B, and cdc2 kinase (Doree & Hunt, 2002; Ohi & Gould, 1999; Stark & Taylor, 2004). Activation of the cdc2 requires cyclin B binding, which is positively regulated through dephosphorylation by cdc25. In turn, Cdc25c can be inhibited by phosphorylation by Chk1 and Chk2. Activated cyclin B then translocates to the nucleus where it greatly reduces the damage-induced G2 arrest. A high level of DNA damage was observed in the RBM3 lacking cells, based on staining for H2AX. Furthermore, high levels of nuclear cyclin B1 were observed, suggesting that the protein is activated. Coupled with this, it was observed that both Chk1 and Chk2 are phosphorylated, and there was increased expression and phosphorylation of Cdc25C. At the same time, significant activation of caspase 3 and high levels of TUNEL positive cells were observed. These data demonstrate a novel process of mitotic catastrophe wherein RBM3 lacking cells undergo apoptosis while at the same time were progressing through G2/M transition, instead of G2/M arrest.

Together, these data imply that RBM3 is a novel protooncogene, which is required for preventing mitotic catastrophe. RBM3 exerts its effects by increasing mRNA stability and translation of otherwise rapidly degraded transcripts. Furthermore, RBM3 is central regulator of tumorigenesis, depletion of which enhances the regression of tumors. Hence, RBM3 may represent a potential target for chemotherapeutic and chemopreventive strategies.

Example 4

Overexpression of RBM3 induces a transformation phenotype. Anchorage independent survival and growth are critical characteristics of malignant cells. Except for some hematopoietic cells, normal cells do not proliferate in suspension culture, defined as anchorage dependence. However, tumor cells can continue to grow in suspension culture or embedded in soft agar, which has been found to closely correlate with their ability to form tumors in animals. Hence, to determine if RBM3 is a protooncogene, growth studies were performed in soft agar. Different cell lines were chosen for these studies where RBM3 was stably overexpressed. The cell lines used for this study were: primary cell lines [D120407 primary culture of human endometrial cells established by Dr. Doris M. Benbrook (OUHSC), PGF primary gingival fibroblast cells established by Dr. Barbara Mioczka (OUHSC)], and non-transformed cell lines [184B5 normal breast epithelial cells (ATCC), MCF 10A breast epithelial cells (Berkeley Lab, CA), IEC-6 normal rat intestinal epithelial cells (ATCC), ARPE-19 normal retinal pigmented epithelial cells (ATCC), MEF 12(1) mouse embryonic fibroblast wild type p53 cells and MEF 10(1) mouse embryonic fibroblast p53 mutant cells established by Dr. Prabhat Goswami (University of IOWA)]. The SW480 colon cancer cell line (ATCC) and J82 bladder cancer cell line (ATCC) were used as positive controls. All cell lines were transformed and formed tight, densely packed compact multicellular spheroids where single cells could not be discriminated (FIG. 28). In contrast, cells transfected with vector alone did not form colonies in soft agar. This data demonstrates that RBM3 is a protooncogene that transforms primary cells when overexpressed.

RBM3 overexpressing NIH-3T3 cells develop tumors in immunocompromised mice. To determine if RBM3 overexpression causes tumors, a xenograft study was performed. $1 \times 10^5$ cells were injected into the flanks of nude mice, and the mice were monitored for 21 days. There were significant size tumors that developed in the mice (FIG. 29). Analysis of the sections of tumors demonstrated that the tumors consisted of both malignant epithelial and malignant stromal cells. Again, these data further confirm that RBM3 is a protooncogene.

EGF induces RBM3 promoter activity: In order to determine that EGF-mediated induction of RBM3 is due to action on RBM3 promoter, a 2-kb fragment of genomic DNA upstream of the RBM3 transcription start site was PCR amplified and cloned upstream of the firefly luciferase gene after confirming the sequence by sequencing both strands. To demonstrate that the region has promoter activity, the plasmid was transfected into HCT-116 cells along with plasmid pRL-TK that encodes the Renila luciferase under the control of the thymidine kinase promoter as controls of transfection. Luciferase activity measurements demonstrated a 6-fold increase in RBM3 promoter activity when compared to the minimal TATA box promoter (FIG. 30). Furthermore, EGF treatment induced RBM3 promoter activity by 2-fold but did not affect the activity of the minimal promoter.

VEGF induces RBM3 expression. Angiogenesis is critical to the growth, invasion, and metastasis of human tumors. Key to this process is the vascular endothelial cell. Tumor growth is angiogenesis-dependent; therefore, cancer cells secrete substances that promote angiogenesis. The major signaling molecule in tumor angiogenesis is VEGF-A, which when bound to VEGFR-2 induces mitogenic, angiogenic and permeability enhancing effects. VEGF-A gene expression is up regulated under hypoxic conditions. In order to determine the role of RBM3 in angiogenesis, Human Umbilical Vein Endothelial cells were treated with Vascular Endothelial Growth Factor (50 ng/ml) (Sigma) for up to 24 h. Following treatment, total RNA was isolated, reverse transcribed and subjected to real-time RT PCR for RBM3. RBM3 mRNA levels were increased from 4 to 24 h following VEGF treatment (FIG. 31). β-actin was used as an internal control.

siRNA-mediated knockdown of RBM3 inhibits angiogenesis. In vitro angiogenesis assay was performed using The CHEMICON® In Vitro Angiogenesis Assay Kit. When cultured on ECMatrix™, a solid gel of basement proteins prepared from the Engelbreth Holm-Swarm (EHS) mouse tumor, these endothelial cells rapidly align and form hollow tube-like structures. Tube formation is a multi-step process involving cell adhesion, migration, differentiation and growth. HUVEC Cells were transfected with scrambled and RBM3 siRNA for 48 h. Following transfection, HUVEC cells ($1 \times 10^4$ cells per well) incubated for 6-10 hours at 37° C. onto the surface of the polymerized ECMatrix™. Data demonstrates that siRNA-mediated knockdown of RBM3 inhibited tube formation, which is a measure of angiogenesis (FIG. 32).

Thus, in accordance with the presently disclosed and claimed invention, there has been provided compositions for inhibiting RNA binding proteins, as well as methods of producing and using same, that fully satisfies the objectives and advantages set forth hereinabove. Although the invention has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the invention.

REFERENCES

The following references, to the extent that they provide exemplary procedural or other details supplementary to those set forth herein, are specifically incorporated herein by reference.

Andreis P G, Whitfield J F and Armato U. (1981). Stimulation of DNA synthesis and mitosis of hepatocytes in primary cultures of neonatal rat liver by arachidonic acid and prostaglandins. *Exp Cell Res* 134: 265-272.

Artavanis-Tsakonas S, Rand M D, Lake R J. Notch signaling: cell fate control and signal integration in development. Science 1999; 284:770-6.

Battelli C, Nikopoulos G N, Mitchell J G, Verdi J M. The RNA-binding protein Musashi-1 regulates neural development through the translational repression of p21WAF-1. Mol Cell Neurosci 2006; 31:85-96.

Blaxall B C, Dwyer-Nield L D, Bauer A K, Bohlmeyer T J, Malkinson A M and Port J D. (2000). Differential expression and localization of the mRNA binding proteins, AU-rich element mRNA binding protein (AUF1) and Hu antigen R (HuR), in neoplastic lung tissue. *Mol. Carcinog.* 28: 76-83.

Bulavin D V, Amundson S A and Fornace A J. (2002). p38 and Chk1 kinases: different conductors for the G(2)/M checkpoint symphony. *Curr Opin Genet Dev* 12: 92-97.

Canman C E. (2001). Replication checkpoint: preventing mitotic catastrophe. *Curr Biol* 11: R121-124.

Carpenter B, McKay M, Dundas S R, Lawrie L C, Telfer C and Murray G I. (2006). Heterogeneous nuclear ribonucleoprotein K is over expressed, aberrantly localised and is associated with poor prognosis in colorectal cancer. *Br J Cancer* 95: 921-927.

Castedo M, Perfettini J L, Roumier T, Andreau K, Medema R, Kroemer G. Cell death by mitotic catastrophe: a molecular definition. Oncogene 2004; 23:2825-37.

Chen C Y and Shyu A B. (1995). AU-rich elements: characterization and importance in mRNA degradation. *Trends Biochem Sci* 20: 465-470.

Chen C Y, Xu N and Shyu A B. (1995). mRNA decay mediated by two distinct AU-rich elements from c-fos and granulocyte-macrophage colony-stimulating factor transcripts: different deadenylation kinetics and uncoupling from translation. *Mol Cell Biol* 15: 5777-5788.

Chen Y Q, Hsieh J T, Yao F, Fang B, Pong R C, Cipriano S C and Krepulat F. (1999). Induction of apoptosis and G2/M cell cycle arrest by DCC. *Oncogene* 18: 2747-2754.

Cok S J and Morrison A R. (2001). The 3'-untranslated region of murine cyclooxygenase-2 contains multiple regulatory elements that alter message stability and translational efficiency. *J. Biol. Chem.* 276: 23179-23185.

Curry C L, Reed L L, Broude E, Golde T E, Miele L, Foreman K E. Notch inhibition in Kaposi's sarcoma tumor cells leads to mitotic catastrophe through nuclear factor-{kappa}B signaling. Mol Cancer Ther 2007; 6:1983-92.

Danno S, Nishiyama H, Higashitsuji H, Yokoi H, Xue J H, Itoh K, Matsuda T and Fujita J. (1997). Increased transcript level of RBM3, a member of the glycine-rich RNA-binding protein family, in human cells in response to cold stress. *Biochem. Biophys. Res. Commun.* 236: 804-807.

Denkert C, Koch I, von Keyserlingk N, Noske A, Niesporek S, Dietel M and Weichert W. (2006a). Expression of the ELAV-like protein HuR in human colon cancer: association with tumor stage and cyclooxygenase-2. *Mod. Pathol.* 19: 1261-1269.

Denkert C, Weichert W, Winzer K J, Muller B M, Noske A, Niesporek S, Kristiansen G, Guski H, Dietel M and Hauptmann S. (2004). Expression of the ELAV-like protein HuR is associated with higher tumor grade and increased cyclooxygenase-2 expression in human breast carcinoma. *Clin. Cancer Res.* 10: 5580-5586.

Derry J M, Kerns J A and Francke U. (1995). RBM3, a novel human gene in Xp11.23 with a putative RNA-binding domain. *Hum. Mol. Genet.* 4: 2307-2311.

Deschenes-Furry J, Belanger G, Mwanjewe J, Lunde J A, Parks R J, Perrone-Bizzozero N and Jasmin B J. (2005). The RNA-binding protein HuR binds to acetylcholinesterase transcripts and regulates their expression in differentiating skeletal muscle cells. *J. Biol. Chem.* 280: 25361-25368.

Dixon D A, Kaplan C D, McIntyre T M, Zimmerman G A and Prescott S M. (2000). Post-transcriptional control of cyclooxygenase-2 gene expression. The role of the 3'-untranslated region. *J. Biol. Chem.* 275: 11750-11757.

Dixon D A, Tolley N D, King P H, Nabors L B, McIntyre T M, Zimmerman G A and Prescott S M. (2001). Altered expression of the mRNA stability factor HuR promotes cyclooxygenase-2 expression in colon cancer cells. *J. Clin. Invest.* 108: 1657-1665.

Doree M and Hunt T. (2002). From Cdc2 to Cdk1: when did the cell cycle kinase join its cyclin partner? *J Cell Sci* 115: 2461-2464.

Dresios J, Aschrafi A, Owens G C, Vanderklish P W, Edelman G M and Mauro V P. (2005). Cold stress-induced protein Rbm3 binds 60S ribosomal subunits, alters microRNA levels, and enhances global protein synthesis. *Proc Natl Acad Sci USA* 102: 1865-1870.

Dubois R N, Abramson S B, Crofford L, Gupta R A, Simon L S, Van De Putte L B and Lipsky P E. (1998). Cyclooxygenase in biology and disease. *Faseb J* 12: 1063-1073.

Eberhart C E, Coffey R J, Radhika A, Giardiello F M, Ferrenbachii S and DuBois R N. (1994). Up-regulation of cyclooxygenase 2 gene expression in human colorectal adenomas and adenocarcinomas. *Gastroenterology* 107: 1183-1188.

Erkinheimo T L, Lassus H, Sivula A, Sengupta S, Furneaux H, Hla T, Haglund C, Butzow R X and Ristimaki A. (2003). Cytoplasmic HuR expression correlates with poor outcome and with cyclooxygenase 2 expression in serous ovarian carcinoma. *Cancer Res.* 63: 7591-7594.

Erkinheimo T L, Sivula A, Lassus H, Heinonen M, Furneaux H, Haglund C, Butzow R X and Ristimaki A. (2005). Cytoplasmic HuR expression correlates with epithelial cancer cell but not with stromal cell cyclooxygenase-2 expression in mucinous ovarian carcinoma. *Gynecol Oncol* 99: 14-19.

Fan X C and Steitz J A. (1998a). HNS, a nuclear-cytoplasmic shuttling sequence in HuR. *Proc. Natl. Acad. Sci. USA* 95: 15293-15298.

Fan X C and Steitz J A. (1998b). Overexpression of HuR, a nuclear-cytoplasmic shuttling protein, increases the in vivo stability of ARE-containing mRNAs. *Embo J.* 17: 3448-3460.

Hacker S and Krebber H. (2004). Differential export requirements for shuttling serine/arginine-type mRNA-binding proteins. *J Biol Chem* 279: 5049-5052.

Heinonen M, Bono P, Narko K, Chang S H, Lundin J, Joensuu H, Furneaux H, Hla T, Haglund C and Ristimaki A. (2005). Cytoplasmic HuR expression is a prognostic factor in invasive ductal breast carcinoma. *Cancer Res* 65: 2157-2161.

Hemmati H D, Nakano I, Lazareff J A, Masterman-Smith M, Geschwind D H, Bronner-Fraser M, Kornblum H I. Cancerous stem cells can arise from pediatric brain tumors. Proc Natl Acad Sci USA 2003; 100:15178-83.

Imai T, Tokunaga A, Yoshida T, Hashimoto M, Mikoshiba K, Weinmaster G, Nakafuku M, Okano H. The neural RNA-binding protein Musashi1 translationally regulates mammalian numb gene expression by interacting with its mRNA. Mol Cell Biol 2001; 21:3888-900.

Kanemura Y, Mori K, Sakakibara S, Fujikawa H, Hayashi H, Nakano A, Matsumoto T, Tamura K, Imai T, Ohnishi T, Fushiki S, Nakamura Y, Yamasaki M, Okano H, Arita N. Musashi1, an evolutionarily conserved neural RNA-binding protein, is a versatile marker of human glioma cells in determining their cellular origin, malignancy, and proliferative activity. Differentiation 2001; 68:141-52.

Kawamori T, Uchiya N, Sugimura T, Wakabayashi K. Enhancement of colon carcinogenesis by prostaglandin E2 administration. Carcinogenesis 2003; 24:985-90.

Krysan K, Reckamp K L, Dalwadi H, Sharma S, Rozengurt E, Dohadwala M and Dubinett S M. (2005). Prostaglandin E2 activates mitogen-activated protein kinase/Erk pathway signaling and cell proliferation in non-small cell lung cancer cells in an epidermal growth factor receptor-independent manner. *Cancer Res.* 65: 6275-6281.

Landegren U. (1984). Measurement of cell numbers by means of the endogenous enzyme hexosaminidase. Applications to detection of lymphokines and cell surface antigens. *J Immunol Methods* 67: 379-388.

Landen C N, Jr., Chavez-Reyes A, Bucana C, Schmandt R. Deavers M T, Lopez-Berestein G and Sood A K. (2005). Therapeutic EphA2 gene targeting in vivo using neutral liposomal small interfering RNA delivery. *Cancer Res* 65: 6910-6918.

Larcher F, Murillas R, Bolontrade M, Conti C J, Jorcano J L. VEGF/VPF overexpression in skin of transgenic mice induces angiogenesis, vascular hyperpermeability and accelerated tumor development. Oncogene 1998; 17:303-11.

Lopez de Silanes I, Fan J, Yang X, Zonderman A B, Potapova O. Pizer E S and Gorospe M. (2003). Role of the RNA-binding protein HuR in colon carcinogenesis. *Oncogene* 22: 7146-7154.

Maller J L. (1991). Mitotic control. *Curr Opin Cell Biol* 3: 269-275.

Marshman E, Booth C, Potten C S. The intestinal epithelial stem cell. Bioessays 2002; 24:91-8.

Millar J B and Russell P. (1992). The cdc25 M-phase inducer: an unconventional protein phosphatase. *Cell* 68: 407-410.

Mukhopadhyay D, Houchen C W, Kennedy S, Dieckgraefe B K and Anant S. (2003a). Coupled mRNA stabilization and translational silencing of cyclooxygenase-2 by a novel RNA binding protein, CUGBP2. *Mol. Cell* 11: 113-126.

Mukhopadhyay D, Jung J, Murmu N, Houchen C W, Dieckgraefe B K and Anant S. (2003b). CUGBP2 plays a critical role in apoptosis of breast cancer cells in response to genotoxic injury. *Ann. N.Y. Acad. Sci.* 1010: 504-509.

Munkarah A R, Morris R, Baumann P, Deppe G, Malone J, Diamond M P and Saed G M. (2002). Effects of prostaglandin E(2) on proliferation and apoptosis of epithelial ovarian cancer cells. *J Soc Gynecol Investig* 9: 168-173.

Myer V E, Fan X C and Steitz J A. (1997). Identification of HuR as a protein implicated in AUUUA-mediated mRNA decay. *Embo J.* 16: 2130-2139.

Nabors L B, Gillespie G Y, Harkins L and King P H. (2001). HuR, a RNA stability factor, is expressed in malignant brain tumors and binds to adenine- and uridine-rich elements within the 3' untranslated regions of cytokine and angiogenic factor mRNAs. *Cancer Res.* 61: 2154-2161.

Niculescu A B, 3rd, Chen X, Smeets M, Hengst L, Prives C, Reed S I. Effects of p21(Cip1/Waf1) at both the G1/S and the G2/M cell cycle transitions: pRb is a critical determinant in blocking DNA replication and in preventing endoreduplication. Mol Cell Biol 1998; 18:629-43.

Ning S and Knox S J. (1999). G2/M-phase arrest and death by apoptosis of HL60 cells irradiated with exponentially decreasing low-dose-rate gamma radiation. *Radiat Res* 151: 659-669.

O'Brien C A, Pollett A, Gallinger S, Dick J E. A human colon cancer cell capable of initiating tumour growth in immunodeficient mice. Nature 2007; 445:106-10.

Ohi R and Gould K L. (1999). Regulating the onset of mitosis. *Curr Opin Cell Biol* 11: 267-273.

Okano H, Imai T, Okabe M. Musashi: a translational regulator of cell fate. J Cell Sci 2002; 115:1355-9.

Okano H, Kawahara H, Toriya M, Nakao K, Shibata S, Imai T. Function of RNA-binding protein Musashi-1 in stem cells. Exp Cell Res 2005; 306:349-56.

Peng S S, Chen C Y, Xu N and Shyu A B. (1998). RNA stabilization by the AU-rich element binding protein, HuR, an ELAV protein. *Embo J.* 17: 3461-3470.

Pinol-Roma S. (1997). HnRNP proteins and the nuclear export of mRNA. *Semin Cell Dev Biol* 8: 57-63.

Potten C S, Booth C, Hargreaves D. The small intestine as a model for evaluating adult tissue stem cell drug targets. Cell Prolif 2003; 36:115-29.

Potten C S, Booth C, Tudor G L, Booth D, Brady G, Hurley P, Ashton G, Clarke R, Sakakibara S, Okano H. Identification of a putative intestinal stem cell and early lineage marker; musashi-1. Differentiation 2003; 71:28-41.

Ricci-Vitiani L, Lombardi D G, Pilozzi E, Biffoni M, Todaro M, Peschle C, De Maria R. Identification and expansion of human colon-cancer-initiating cells. Nature 2007; 445:111-5.

Riehl T E, George R J, Sturmoski M A, May R, Dieckgraefe B, Anant S, Houchen C W. Azoxymethane protects intestinal stem cells and reduces crypt epithelial mitosis through a COX-1-dependent mechanism. *Am J Physiol Gastrointest Liver Physiol* 2006; 291:G1062-70.

Ristimaki A, Narko K and Hla T. (1996). Down-regulation of cytokine-induced cyclo-oxygenase-2 transcript isoforms by dexamethasone: evidence for post-transcriptional regulation. *Biochem J* 318 (Pt 1): 325-331.

Sakakibara S, Imai T, Hamaguchi K, Okabe M, Aruga J, Nakajima K, Yasutomi D, Nagata T, Kurihara Y, Uesugi S, Miyata T, Ogawa M, Mikoshiba K, Okano H. Mouse-Musashi-1, a neural RNA-binding protein highly enriched in the mammalian CNS stem cell. *Dev Biol* 1996; 176:230-42.

Shao J, Lee S B, Guo H, Evers B M, Sheng H. Prostaglandin E2 stimulates the growth of colon cancer cells via induction of amphiregulin. *Cancer Res* 2003; 63:5218-23.

Shyu A B and Wilkinson M F. (2000). The double lives of shuttling mRNA binding proteins. *Cell* 102: 135-138.

Stark G R and Taylor W R. (2004). Analyzing the G2/M checkpoint. *Methods Mol Biol* 280: 51-82.

Sureban S M, Murmu N, Rodriguez P, May R, Maheshwari R, Dieckgraefe B K, Houchen C W and Anant S. (2007). Functional antagonism between RNA binding proteins HuR and CUGBP2 determines the fate of COX-2 mRNA translation. *Gastroenterology* 132: 1055-1065.

Sutherland L C, Rintala-Maki N D, White R D and Morin C D. (2005). RNA binding motif (RBM) proteins: a novel family of apoptosis modulators? *J. Cell. Biochem.* 94: 5-24.

Takei Y, Kadomatsu K, Yuzawa Y, Matsuo S, Muramatsu T. A small interfering RNA targeting vascular endothelial growth factor as cancer therapeutics. *Cancer Res* 2004; 64:3365-70.

Taylor W R and Stark G R. (2001). Regulation of the G2/M transition by p53. *Oncogene* 20: 1803-1815.

Tsao Y P, Huang S J, Chang J L, Hsieh J T, Pong R C, Chen S L. Adenovirus-mediated p21((WAF1/SDII/CIP1)) gene transfer induces apoptosis of human cervical cancer cell lines. *J Virol* 1999; 73:4983-90.

Ueno M, Katayama K, Yamauchi H, Nakayama H, Doi K. Cell cycle and cell death regulation of neural progenitor cells in the 5-azacytidine (5AzC)-treated developing fetal brain. *Exp Neurol* 2006; 198:154-66.

Wahl A F, Donaldson K L, Fairchild C, Lee F Y, Foster S A, Demers G W and Galloway D A. (1996). Loss of normal p53 function confers sensitization to Taxol by increasing G2/M arrest and apoptosis. *Nat Med* 2: 72-79.

Walworth N C. (2001). DNA damage: Chk1 and Cdc25, more than meets the eye. *Curr Opin Genet Dev* 11: 78-82.

Wang D, Mann J R and DuBois R N. (2005). The role of prostaglandins and other eicosanoids in the gastrointestinal tract. *Gastroenterology* 128: 1445-1461.

Wang D, Wang H, Shi Q, Katkuri S, Walhi W, Desvergne B, Das S K, Dey S K, DuBois R N. Prostaglandin E(2) promotes colorectal adenoma growth via transactivation of the nuclear peroxisome proliferator-activated receptor delta. *Cancer Cell* 2004; 6:285-95.

Whither RNAi? *Nat Cell Biol* 2003; 5:489-90.

Wu G, Yi J, Di F, Zou S and Li X. (2005). Celecoxib inhibits proliferation and induces apoptosis via cyclooxygenase-2 pathway in human pancreatic carcinoma cells. *J Huazhong Univ Sci Technolog Med Sci* 25: 42-44.

Yamashita H, Osaki M, Honjo S, Yoshida H, Teshima R and Ito H. (2003). A selective cyclooxygenase-2 inhibitor, NS-398, inhibits cell growth by cell cycle arrest in a human malignant fibrous histiocytoma cell line. *Anticancer Res* 23: 4671-4676.

Yokota N, Mainprize T G, Taylor M D, Kohata T, Loreto M, Ueda S, Dura W, Grajkowska W, Kuo J S, Rutka J T. Identification of differentially expressed and developmentally regulated genes in medulloblastoma using suppression subtraction hybridization. *Oncogene* 2004; 23:3444-53.

---

What is claimed is:

1. A short-interfering ribonucleic acid (siRNA) molecule effective at silencing RNA binding motif protein 3 (RBM3) expression, wherein said siRNA comprises a sense RNA strand and an antisense RNA strand, wherein the sense and antisense RNA strands form an RNA duplex, and wherein the sense RNA strand comprises a nucleotide sequence identical to a target sequence of about 15 to about 25 contiguous nucleotides in RBM3 mRNA, and wherein the sense RNA strand comprises SEQ ID NO:11.

2. A pharmaceutical composition comprising the siRNA of claim 1.

3. The pharmaceutical composition of claim 2, further comprising at least one additional chemotherapeutic agent.

4. The pharmaceutical composition of claim 2, further comprising a delivery agent.

5. The pharmaceutical composition of claim 4, wherein the delivery agent comprises a liposome.

6. A method of inhibiting expression of RNA binding motif protein 3 (RBM3) protein, comprising the steps of:
   providing a cell expressing RBM3;
   providing a short-interfering ribonucleic acid (siRNA) comprising a sense RNA strand and an antisense RNA strand, wherein the sense and antisense RNA strands form an RNA duplex, wherein the sense RNA strand comprises a nucleotide sequence identical to a target sequence of about 15 to about 25 contiguous nucleotides in RBM3 mRNA, and wherein the sense RNA strand comprises SEQ ID NO:11; and
   contacting the cell with the siRNA, thereby specifically inhibiting the expression of RBM3.

7. A method of inhibiting expression of RNA binding motif protein 3 (RBM3) protein in a subject, comprising the step of:
   administering to a subject an effective amount of pharmaceutical composition comprising a short-interfering ribonucleic acid (siRNA) comprising a sense RNA strand and an antisense RNA strand, wherein the sense and antisense RNA strands form an RNA duplex, wherein the sense RNA strand comprises a nucleotide sequence identical to a target sequence of about 15 to about 25 contiguous nucleotides in RBM3 mRNA, and wherein the sense RNA strand comprises SEQ ID NO:11, thereby specifically inhibiting the expression of RBM3.

8. The method of claim 7, wherein the pharmaceutical composition further comprises a delivery agent.

9. The method of claim 8, wherein the delivery agent comprises a liposome.

10. A method of inhibiting tumor growth, comprising the steps of:
    providing a short-interfering ribonucleic acid (siRNA) comprising a sense RNA strand and an antisense RNA strand, wherein the sense and antisense RNA strands form an RNA duplex, wherein the sense RNA strand comprises a nucleotide sequence identical to a target sequence of about 15 to about 25 contiguous nucleotides in RNA binding motif protein 3 (RBM3) mRNA, and wherein the sense RNA strand comprises SEQ ID NO:11; and
    contacting the tumor with the siRNA, thereby specifically inhibiting the expression of RBM3 in the tumor and thus inhibiting growth of the tumor.

11. A method of inhibiting tumor growth in a subject, comprising the steps of:
    providing a pharmaceutical composition comprising a short-interfering ribonucleic acid (siRNA), the siRNA comprising a sense RNA strand and an antisense RNA strand, wherein the sense and antisense RNA strands form an RNA duplex, wherein the sense RNA strand comprises a nucleotide sequence identical to a target sequence of about 15 to about 25 contiguous nucleotides in RNA binding motif protein 3 (RBM3) mRNA, and wherein the sense RNA strand comprises SEQ ID NO:11; and
    administering an effective amount of the pharmaceutical composition to the subject, thereby specifically inhibiting the expression of RBM3 in the tumor and thus inhibiting growth of the tumor.

* * * * *

UNITED STATES PATENT AND TRADEMARK OFFICE
CERTIFICATE OF CORRECTION

PATENT NO.        : 7,902,166 B2
APPLICATION NO.   : 12/386550
DATED             : March 8, 2011
INVENTOR(S)       : Houchen et al.

It is certified that error appears in the above-identified patent and that said Letters Patent is hereby corrected as shown below:

Column 32, line 2: Delete "(Mailer," and replace with -- (Maller, --
Column 38, line 66-67: Delete "Ferrenbachii" and replace with -- Ferrenbach --
Column 39, line 5: After "Butzow R" delete "X".
Column 39, line 10: After "Butzow R" delete "X".

Signed and Sealed this
Third Day of May, 2011

David J. Kappos
*Director of the United States Patent and Trademark Office*

SEQUENCE LISTING

```
<160> NUMBER OF SEQ ID NOS: 22

<210> SEQ ID NO 1
<211> LENGTH: 2950
<212> TYPE: RNA
<213> ORGANISM: Homo sapiens

<400> SEQUENCE: 1
gcgccgagcg ccgccgccgc cgccgccgcc gccgcuccgc ugcccgcgcc gcccgcggcu      60
cccgauggag acugacgcgc cccagcccgg ccucgccucc ccggacucgc cgcacgaccc     120
cugcaagaug uucaucgggg gacucaguug gcagacuacg caggaagggc ugcgcgaaua     180
cuucggccag uucggggagg ugaaggagug ucuggugaug cgggaccccc ugaccaagag     240
auccaggggu uucggcuucg ucacuuucau ggaccaggcg ggggguggaua aagugcuggc     300 gcaaucgcgg cacgagcucg acuccaaaac aauugacccu aaguggccu ucccucgcg      360 agcacagccc aagaugguga cucgaacgaa gaagaucuuu gugggggggc ugucggugaa     420
caccacggug gaggacguga agcaauauuu ugagcaguuu gggaaggugg acgacgccau     480
gcugauguuu gacaaaacca ccaaccggca ccgagggguuc ggguuuguca cguuugagag     540
ugaggacauc guggagaaag ugugugaaau ucauuuucau gaaaucaaca caaaaauggu     600
ggaauguaag aaagcucagc caaaggaggu gaugucgcca acgggcucag cccggggggag     660
```

-continued

```
gucucgaguc augcccuacg gaauggacgc cuucaugcug ggcaucggca ugcuggguua    720
cccagguuuc caagccacaa ccuacgccag ccggaguuau acaggccucg ccccuggcua    780
caccuaccag uucccgaauc uccguguaga gcggaccccu cucccgagcg ccccaguccu    840
ccccgagcuu acagccauuc cucucacugc cuacggacca auggcggcgg cagcggcggc    900
agcggcugug guucgaggga caggcucuca ccccuggacg auggcuccc cuccagguuc    960 gacucccagc cgcacagggg gcuuccuggg gaccaccagc cccggcccca uggccgagcu   1020
cuacggggcg gccaaccagg acucggggu cagcaguuac aucagcgccg ccagcccugc    1080
ccccagcacc ggcuucggcc acagucuugg gggcccuuug auugccacag ccuucaccaa    1140
uggguaccac ugaagcaggg gacgguggca ggagcgcccc agccugcagc ugacugagga    1200
ccacgaguga gccagcgagg gggcgggaga ccucagccgc agccgccgcc cccucccug    1260 cagcgacucg gacccgcuac ugccugcccc caaucccccg ggccggccc ugcccugcu     1320 gcccccaaca gcgucuggcu ccccuacuaa cguccccuc uucgcccuug ccccauccc     1380 cacccgcccc cucccggcc cugcuuuuau uuauuuugga uuagccgguu gccacccca    1440 gcccucuggu ccaucccucc cuccgugccg cgcccccua ggaccgcccc cucccaaaa    1500 ggcuuuugga uuugugcaua gcuggaguga aggcggaggg agccugcuac aggccgcagc    1560
ccaaccccug uuuuuuauuc agauuucccc uccuuuaccc uuucccuuuu uuuuuuuuu    1620 uuuuuuuua aagaaaccuu uuuuaaacua uuucuagguu ugugaaugug aagcccagg    1680 ccgcaggggg caagggccca ggugccccc accagcugag aacaaagugu cuaucgggu    1740 gugggcccu ggccgccucc cuccagcccu ggagaggagg gcagggcugc ggggaggcca    1800
ggccgagccc cuggaaccau cccguccugu aucauaugua aauacuguga ggugaugugc    1860
ccaccccucu cuaagacccc ucgggggcuga gggcucccc ccucccugu uucugucccc    1920 ucagacaccg uuacuguaag cuugcaggcc ucagcugugg ccacggcagg cccgcucucu    1980
caggcccuca gggucaaggc cuugguugga ccugcccacu ccaaaaaccc agugugggg    2040 caaagggcgu gggaagagca gggcuugccc agcgacacug cuggacagga auuaacucuc    2100
caaaggucuc cccugcuccc uaccagguu ggggcuucau gguuucugcu cagucugucc    2160
cccuuccccc ucgaccccg caaugagugg gcaccagggg acgcucuggc gagggcagac    2220 cccagggaa agcaaagggc gucucaggga acccccacau ucucacug aaguucccca    2280 ccaggaugac cccacagcca gagucccuug gcagccccuc accccagacc cccuucuaa    2340 ggaaaaagag agguucagag cguuggaccu ucaugaacag uggccuggcu ggcguggcag    2400
ggccaaggcc cacccacugc caucccccuu cuguguguccc cucucccccc aguuaugaggc    2460 ccagggccug agcucucuuc cccagcauug cccccacccg gaaacccac cuuuggagag    2520 uuaauugucu gugugaggug cuuaaccauu cagcccugag aacacaaagc aauaaucuuu    2580
guuacugaga ugcgcggcug uucguguuuu gggguuuuuu uuuuuuuaau guuccuaau    2640 aaaagagaag cugcauuuua uugguuuuua uuuuuuaauu ucuacacguu ugagcugagu    2700
ccugagacac uuagcuuccc ucccucau uccggaccc uucacccca cugggccaa    2760 ccaugggcuc aggacccugg aauuccguuu ucugauuugc uuugggauuu uuuuuuuuu    2820 uaagauguua cauggugu cgaagccagc aaguuaccau ccuccggugu cucucucuc    2880 cacaucugua acuucuuuuu ccagguuuua uuuucaguuu uaaauuccua auaaauuauu    2940
ugaaaacguu                                                          2950
```

```
<210> SEQ ID NO 2
<211> LENGTH: 17
<212> TYPE: RNA
<213> ORGANISM: Homo sapiens

<400> SEQUENCE: 2
cuuuuggauu ugugcau                                                    17

<210> SEQ ID NO 3
<211> LENGTH: 17
<212> TYPE: RNA
<213> ORGANISM: Homo sapiens

<400> SEQUENCE: 3
acaucgugga gaaagug                                                    17

<210> SEQ ID NO 4
<211> LENGTH: 21
<212> TYPE: DNA
<213> ORGANISM: Homo sapiens

<400> SEQUENCE: 4
ggtgatccac atctgctgga a                                               21

<210> SEQ ID NO 5
<211> LENGTH: 20
<212> TYPE: DNA
<213> ORGANISM: Homo sapiens

<400> SEQUENCE: 5
atcattgctc ctcctcaggg                                                 20

<210> SEQ ID NO 6
<211> LENGTH: 24
<212> TYPE: DNA
<213> ORGANISM: Homo sapiens

<400> SEQUENCE: 6
cagtttcgga cctatctctg aggt                                            24

<210> SEQ ID NO 7
<211> LENGTH: 23
<212> TYPE: DNA
<213> ORGANISM: Homo sapiens

<400> SEQUENCE: 7
aaggtgatga aaccaaaacc cct                                             23

<210> SEQ ID NO 8
<211> LENGTH: 20
<212> TYPE: DNA
<213> ORGANISM: Homo sapiens

<400> SEQUENCE: 8
tgagctggca gacctcacca                                                 20

<210> SEQ ID NO 9
<211> LENGTH: 20
<212> TYPE: DNA
<213> ORGANISM: Homo sapiens

<400> SEQUENCE: 9
aaaccgaagc ctctggagcg                                                 20
```

```
<210> SEQ ID NO 10
<211> LENGTH: 1588
<212> TYPE: RNA
<213> ORGANISM: Homo sapiens

<400> SEQUENCE: 10
gggaacguuc cgggacguuc ucgcuacgua cucuuuauca aucgucuucc ggcgcagccc      60
cgucccuguu uuuguguguc uccgagcuc gcuguucguc cggguuuuuu acguuuuaau     120
uuccaggacu ugaacugcca uguccucuga agaaggaaag cuuucgugg gagggcucaa     180 cuuuaacacc gacgagcagg cacuggaaga ccacucuagc aguuucggac cuaucucuga    240 ggugguucguu gucaaggacc gggagacuca gcgguccagg ggguuuggu ucaucaccuu    300 caccaaccca gagcaugcuu caguugccau gagagccaug aacggagagu cucuggaugg    360
ucgucagauc cguguggauc augcaggcaa gucugcucgg ggaaccagag gagguggcuu    420 ugggggcccau gggcgugguc gcagcuacuc uagagguggu ggggaccagg gcuauggag    480 uggcaggauau auugacaguc gaccuggagg guauggauau ggauauggac guuccagaga    540
cuauaauggc agaaaccagg gugguuauga ccgcuacuca ggaggaaauu acagagacaa    600
uuaugacaac ugaaaugaga caugcacaua auauagauac acaaggaaua auucugauc    660 caggaucguc cuccaaaug gcuguauuua uaaagguuuu uggagcugca ccgaagcauc     720 uuauuuauia guauucaaca cuuuuguuu uaaauugacc ugccaaggua gcugaagacc    780
uuuuagacag uuccaucuuu uuuuuaaau uuuucugcc uauuuaaaga caaauuaugg    840
gacguuugua gaaccugagu auuuucuuu uuaccaguuu uuuaguuuga gcucuuaggu    900
uuauuggagc uagcaauaau uugguucuggc aaguuuggcc agacugacuu caaaaaauua   960
auguguaucc agggacauuu uaaaaaaccug uacacagugu uuaguguggu uaggaagcaa  1020 uuuucccaaug uaccuauaag aaaugugcau caagccagcc ugaccaacau ggugaaaccc  1080
caucuguacu aaaacauaaaa aaauuagccu ggcauggugg uguacgccug uaaucccagu  1140
gacuugggag gcugaggcag gagaaucgcu ugaacccggg aggcggaggu ugcagugagc   1200
uaagaucgcg ccacuguacu ccagccuggg caacagcgag acuccaucuc aaaaaaaaag   1260
gaaaugugua ucaagaacau gauuauccag cgguauuuuc uaauucagau caucaaacug   1320
auuauauaga agaguuggcu uuaaaaauguu ugcaaauguc uuuuuuuuu uaauacugga   1380 agaaaaaaua uucguugug ucucauacag ugcuuaggau gucuuucaca gagcuuauua    1440
aaaagaugaa accugagaac aaacugcuuu auucuuacuc agcccauuuu gcaaauuaaa    1500 aguggggggca gaggugggcg gaucaccuga ggucaggagu cgagaccag ccuggccaac    1560 agggcaaaac cccaucucua cuaaaaau                                       1588

<210> SEQ ID NO 11
<211> LENGTH: 19
<212> TYPE: RNA
<213> ORGANISM: Homo sapiens

<400> SEQUENCE: 11
ggguauggau auggauaug                                                  19

<210> SEQ ID NO 12
<211> LENGTH: 24
<212> TYPE: DNA
<213> ORGANISM: Homo sapiens

<400> SEQUENCE: 12
cagtttcgga cctatctctg aggt                                            24
```

```
<210> SEQ ID NO 13
<211> LENGTH: 23
<212> TYPE: DNA
<213> ORGANISM: Homo sapiens

<400> SEQUENCE: 13
aaggtgatga aaccaaaacc cct                                              23

<210> SEQ ID NO 14
<211> LENGTH: 20
<212> TYPE: DNA
<213> ORGANISM: Homo sapiens

<400> SEQUENCE: 14
gtgaactacg tgaccgcgaa                                                  20

<210> SEQ ID NO 15
<211> LENGTH: 18
<212> TYPE: DNA
<213> ORGANISM: Homo sapiens

<400> SEQUENCE: 15
gactggagcc tcaagccg                                                    18

<210> SEQ ID NO 16
<211> LENGTH: 22
<212> TYPE: DNA
<213> ORGANISM: Homo sapiens

<400> SEQUENCE: 16
gaatcattca ccaggcaaat tg                                               22

<210> SEQ ID NO 17
<211> LENGTH: 20
<212> TYPE: DNA
<213> ORGANISM: Homo sapiens

<400> SEQUENCE: 17
tctgtactgc gggtggaaca                                                  20

<210> SEQ ID NO 18
<211> LENGTH: 21
<212> TYPE: DNA
<213> ORGANISM: Homo sapiens

<400> SEQUENCE: 18
ctcttggcag ccttcctgat t                                                21

<210> SEQ ID NO 19
<211> LENGTH: 27
<212> TYPE: DNA
<213> ORGANISM: Homo sapiens

<400> SEQUENCE: 19
tatgcactga gatctaagtt ctttagc                                          27

<210> SEQ ID NO 20
<211> LENGTH: 19
<212> TYPE: DNA
<213> ORGANISM: Homo sapiens

<400> SEQUENCE: 20
agcgcaagaa atcccggta                                                   19
```

```
<210> SEQ ID NO 21
<211> LENGTH: 19
<212> TYPE: DNA
<213> ORGANISM: Homo sapiens

<400> SEQUENCE: 21
tgctttctcc gctctgagc                                                19

<210> SEQ ID NO 22
<211> LENGTH: 15
<212> TYPE: PRT
<213> ORGANISM: Homo sapiens

<400> SEQUENCE: 22

Tyr Asp Arg Tyr Ser Gly Gly Asn Tyr Arg Asp Asn Tyr Asp Asn
1               5                   10                  15
```